US010100047B2

(12) United States Patent
He et al.

(10) Patent No.: US 10,100,047 B2
(45) Date of Patent: Oct. 16, 2018

(54) PIPERIDINE DERIVATIVES AS OREXIN RECEPTOR ANTAGONIST

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(72) Inventors: Haiying He, Shanghai (CN); Songliang Wu, Shanghai (CN); Yang Zhang, Shanghai (CN); Biao Ma, Shanghai (CN); Yuan Chen, Shanghai (CN); Yuhe Wang, Shanghai (CN); Shuhui Chen, Shanghai (CN); Qiang Lv, Shanghai (CN); Jiong Lan, Shanghai (CN); Xing Liu, Shanghai (CN)

(73) Assignees: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

( * ) Notice: Subject to any disclaimer, the term of this patent is extended or adjusted under 35 U.S.C. 154(b) by 0 days.

(21) Appl. No.: 15/123,014

(22) PCT Filed: Feb. 27, 2015

(86) PCT No.: PCT/CN2015/073330
§ 371 (c)(1),
(2) Date: Sep. 1, 2016

(87) PCT Pub. No.: WO2015/131773
PCT Pub. Date: Sep. 11, 2015

(65) Prior Publication Data
US 2017/0233385 A1    Aug. 17, 2017

(30) Foreign Application Priority Data

Mar. 6, 2014  (CN) .......................... 2014 1 0081220

(51) Int. Cl.
*C07D 451/02*    (2006.01)
(52) U.S. Cl.
CPC ................... *C07D 451/02* (2013.01)

(58) Field of Classification Search
CPC .................................................... C07D 451/02
See application file for complete search history.

(56) References Cited

U.S. PATENT DOCUMENTS

2011/0009401 A1    1/2011  Aissaoui et al.

FOREIGN PATENT DOCUMENTS

| EP | 2 261 210 A1 | 12/2010 |
| WO | 2004/101562 A2 | 11/2004 |
| WO | 2008/147518 A1 * | 12/2008 |
| WO | 2014/075392 A1 | 5/2014 |
| WO | 2014/159591 A1 | 10/2014 |
| WO | 2014/165070 A1 | 10/2014 |

OTHER PUBLICATIONS

English translation of International Search Report corresponding to PCT/CN2015/073330 dated Jun. 12, 2015; 3 pages.
Baxter, Carl A. et al., "The First Large-Scale Synthesis of MK-4305: A Dual Orexin Receptor Antagonist for the Treatment of Sleep Disorder," *Org. Process Res. Dev.* (Mar. 4, 2011); 15:367-375.
Ogier, Lionel et al., "Rearrangement of a Mesylate Tropane Intermediate in Nucleophilic Substitution Reactions, Synthesis of Aza-Bicyclo[3.2.1]octane and Aza-Bicyclo[3.2.2.]nonane Ethers, Imides, and Amines," *J. Org. Chem.* (2002; revised manuscript); 67(11):3637-3642.
Renzulli, Cecilia et al., "Disposition and Metabolism of [$^{14}$C]SB-649868, an Orexin 1 and 2 Receptor Antagonist, in Humans," *Drug Metabolism and Disposition* (2011; accepted Nov. 2, 2010); 39(2):215-227.
Runyon, Scott P. et al., "Synthesis, structural identification, and ligand binding of tropane ring analogs of paroxetine and an unexpected aza-bicyclo[3.2.2]nonane rearrangement product," *Bioorg. Med. Chem.* (accepted Jan. 24, 2005) 13:2439-2449.

* cited by examiner

*Primary Examiner* — Alexander R Pagano
*Assistant Examiner* — Ebenezer O Sackey
(74) *Attorney, Agent, or Firm* — Mintz Levin Cohn Ferris Glovsky and Popeo, PC

(57) ABSTRACT

The present invention discloses a series of piperidine derivatives as orexin receptor antagonists and compositions thereof, and relates to the application thereof in preparing medications for the treatment of insomnia, chronic obstructive pulmonary disease, obstructive sleep apnea, hypersomnia, anxiety, obsessive-compulsive disorder, panic attack, nicotine addiction, or binge eating disorder.

10 Claims, No Drawings

PIPERIDINE DERIVATIVES AS OREXIN RECEPTOR ANTAGONIST

FIELD OF THE INVENTION

The present invention relates to piperidine derivatives as orexin receptor antagonists and compositions thereof, and relates to their uses in preparing a medication for treatment of insomnia, chronic obstructive pulmonary disease, obstructive sleep apnea, hypersomnia, anxiety, obsessive-compulsive disorder, panic attack, nicotine addiction, or binge eating disorder.

BACKGROUND OF THE INVENTION

Orexin (or orexine) produced by the hypothalamus includes two neuropeptides: the orexin A (OX-A) (a peptide with 33 amino acids) and the orexin B (OX-B) (a peptide with 28 amino acids) (Sakurai T., et al., Cell, 1998, 92, 573-585). It is found that orexin can stimulate food consumption in rats, that is to say, in the center feedback mechanism of regulation of feeding behavior, the peptide has a physiological role as a medium (Sakurai T. et al., Cell, 1998, 92, 573-585). Orexin can regulate sleep and insomnia status, thereby potentially providing a new method for treatment of sleep in patients with insomnia or paroxysmal (Chemelli R. M. et al., Cell, 1999, 98, 437-451). Orexin also play a role in awakening, motivation, learning and memory (Harris, et al., Trends Neuroscl., 2006, 29 (10), 571-577). Two orexin receptors have been cloned and characterized in mammals, which belong to the G protein-coupled receptor superfamily (Sakurai T. et al., Cell, 1998, 92, 573-585): the orexin-1 receptor (0X or 0X1R) is selective for OX-A, and orexin-2 receptor (OX2 or OX2R) is capable of binding OX-A and OX-B. It is believed that the physiological role of orexin is assumed to be preformed with either or both of OXI receptor and OX2 (two subtypes of orexin receptor).

Orexin receptors can be found in brain of warm-blooded animals, and is involved in many diseases, e.g., depression; anxiety; addiction; obsessive compulsory disorder; affective neurosis; depressive neurosis; anxiety neurosis; dysthymic disorder; behavioral disorders; mood disorders; sexual dysfunction; psychosexual dysfunction; gender disorder; schizophrenia; manic depression; delirium; dementia; severe mental retardation and movement disorders, such as Huntington's disease and Tourette syndrome; eating disorders such as anorexia, bulimia, cachexia, and obesity; addictive feeding behavior; binge eating crash feeding behavior; cardiovascular disease; diabetes; appetite or taste disorders; emesis, vomiting, nausea; asthma; cancer; Parkinson's disease; Cushing's syndrome; basophil adenoma; prolactinoma; hyperprolactinemia; pituitary tumor or adenoma; under hypothalamic disease; inflammatory bowel disease; gastric dysfunction; gastric ulcer; obesity genital degradation; pituitary disorders; pituitary gland disorders; pituitary hypogonadism; pituitary hyperactivity; hypothalamic hypogonadism; Kallmann's comprehensive disease (anosmia, hyposmia); functional or psychogenic amenorrhea; hypopituitarism; hypothalamic hypothyroidism; hypothalamus-adrenal dysfunction; sudden hyperprolactinemia; hypothalamic disease growth hormone deficiency; sudden lack of growth; dwarfism; gigantism; acromegaly; disturbed biological and circadian rhythms; sleep disorders associated with diseases such as neurological disorders, neuropathic pain and restless leg syndrome; heart and lung diseases, acute and congestive heart failure; hypotension; hypertension; urinary retention; osteoporosis; angina; acute myocardial infarction; ischemic or hemorrhagic stroke; subarachnoid hemorrhage; ulcers; allergic reaction; benign prostatic hypertrophy; chronic renal failure; kidney disease; impaired glucose tolerance; migraine; hyperalgesia; pain; enhanced or exaggerated sensitivity to pain such as hyperalgesia, causalgia and allodynia; acute pain; burning pain; atypical facial pain; neuropathic pain; back pain; complex regional pain syndrome I and II; arthritic pain; sports injury pain; and infections (such as HIV) related pain, post-chemotherapy pain; post-stroke pain; post-operative pain; neuralgia; vomiting, nausea, vomiting; visceral pain related disorders, such as irritable bowel syndrome and angina; migraine; urinary bladder incontinence, for example, urge incontinence; tolerance to narcotics or anesthetics; sleep disorders; sleep apnea; insomnia; parasomnia; jet lag syndrome; and neurodegenerative disorders, including disease classification entities such as disinhibition-dementia-Parkinson's-muscular atrophy syndrome; epilepsy; seizure disorders and other general orexin system dysfunction related diseases.

Some orexin receptor antagonists are disclosed in the following patents: WO99/09024, WO 99/58533, WO 00/47576, WO 00/47577, WO 00/47580, WO 01/68609, WO01/85693, WO 01/96302, WO 2002/044172, WO 2002/051232, WO 2002/051838, WO2002/089800, WO 2002/090355, WO 2003/002559, WO 2003/002561, WO 2003/032991, WO2003/037847, WO 2003/041711, WO 2003/051368, WO 2003/051872, WO 2003/051873, WO2004/004733, WO 2004/026866, WO 2004/033418, WO 2004/041807, WO 2004/041816, WO2004/052876, WO 2004/083218, WO 2004/085403, WO 2004/096780, WO 2005/060959, WO2005/075458, WO2005/118548, WO 2006/067224, WO 2006/110626, WO 2006/127550, WO2007/019234, WO 2007/025069, WO 2007/061763, WO 2007/116374, WO 2007/122591, WO2007/126934, WO 2007/126935, WO2008/008517, WO 2008/008518, WO 2008/008551, WO2008/020405, WO 2008/026149, and WO2008/038251.

Further, on the basis of the above patents, WO2008147518 (or CN101679366 B) has disclosed a structure of formula B-I and MK6096:

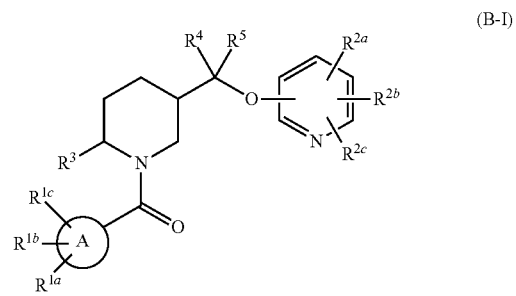

(B-I)

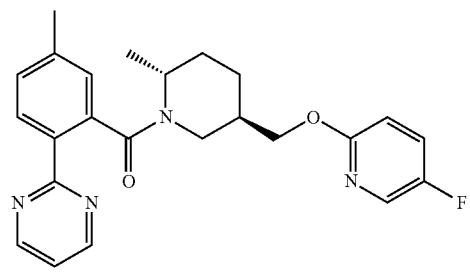

(MK6096)

SUMMARY OF THE INVENTION

The purpose of the present invention is to provide a compound of formula (I), or a pharmaceutically acceptable salt thereof,

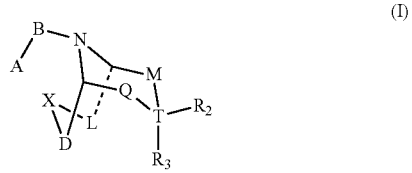

(I)

wherein:

A is selected from an optionally substituted 3-12 membered cyclohydrocarbyl or heterocyclohydrocarbyl or cyclic heterohydrocarbyl; wherein the cyclohydrocarbyl or heterocyclohydrocarbyl or cyclic heterohydrocarbyl is in form of single ring, bicyclic ring, spiro ring, condensed ring or fused ring, and the substituent is selected from the group consisting of F, Cl, Br, I, CN, =O, =S, OH, SH, $NH_2$, a halogen-substituted, hydroxy-substituted, amino-substituted or unsubstituted $C_{1-6}$ alkyl or heteroalkyl or alkyl hetero group or heteroalkyl hetero group, and a halogen-substituted, hydroxy-substituted, amino-substituted or unsubstituted $C_{3-8}$ cyclic group or heterocyclic group or cyclic hetero group or heterocyclic hetero group; wherein the hetero atom or heteroatom group is independently selected from $C_{1-6}$ alkyl substituted, $C_{3-8}$ cycloalkyl substituted or unsubstituted C(=O)NH, C(=O)O, $C_{1-6}$ alkyl substituted or $C_{3-8}$ cycloalkyl substituted or unsubstituted NH, O, S, $C_{1-6}$ alkyl substituted or $C_{3-8}$ cycloalkyl substituted or unsubstituted C=NH, C=O, C=S, S(=O) and/or $S(=O)_2$, wherein the number of substituent, heteroatom or heteroatom group is arbitrary as long as chemical stability is achievable;

B is selected from C(=O), S(=O) or $S(=O)_2$;

X is selected from optionally substituted $(CH_2)_{r1}(U)_{r2}(CH_2)_{r3}$, wherein the substituent is selected from the group consisting of F, Cl, Br, I, CN, =O, =S, OH, SH, $NH_2$, halogen-substituted, hydroxy-substituted, amino-substituted or unsubstituted $C_{1-6}$ alkyl or heteroalkyl or alkyl hetero group or heteroalkyl hetero group, halogen-substituted, hydroxy-substituted, amino-substituted or unsubstituted $C_{3-8}$ cyclic group or heterocyclic group or cyclic hetero group or heterocyclic hetero group, wherein the hetero atom or heteroatom group is independently selected from $C_{1-6}$ alkyl substituted, $C_{3-8}$ cycloalkyl substituted or unsubstituted C(=O)NH, C(=O)O, $C_{1-6}$ alkyl substituted or $C_{3-8}$ cycloalkyl substituted or unsubstituted NH, O, S, $C_{1-6}$ alkyl substituted or $C_{3-8}$ cycloalkyl substituted or unsubstituted C=NH, C=O, C=S, S(=O) and/or $S(=O)_2$, wherein the number of substituent, heteroatom or heteroatom group is arbitrary as long as chemical stability is achievable;

$r_1$ and $r_3$ are independently selected from 0, 1 or 2, $r_2$ is selected from 0 or 1, and when $r_1$, $r_2$ and $r_3$ are all 0, it means that X is a single bond of linkage;

U is selected from halogen-substituted, hydroxy-substituted, amino-substituted or unsubstituted $CH_2$, $C_{1-6}$ alkyl substituted or $C_{3-8}$ cycloalkyl substituted or unsubstituted C(=O)NH, C(=O)O, $C_{1-6}$ alkyl substituted or $C_{3-8}$ cycloalkyl substituted or unsubstituted NH, O, S, $C_{1-6}$ alkyl substituted or $C_{3-8}$ cycloalkyl substituted or unsubstituted C=NH, C=O, C=S, S(=O) and/or $S(=O)_2$, wherein the number of substituent is arbitrary as long as chemical stability is achievable;

D and L are independently selected from optionally substituted $CH_2$, wherein the substituent is selected from F, Cl, Br, I, CN, =O, =S, OH, SH, $NH_2$, halogen-substituted, hydroxy-substituted, amino-substituted or unsubstituted $C_{1-6}$ alkyl or heteroalkyl or alkyl hetero group or heteroalkyl hetero group, halogen-substituted, hydroxy-substituted, amino-substituted or unsubstituted $C_{3-8}$ cyclic group or heterocyclic group or cyclic hetero group or heterocyclic hetero group, wherein the hetero atom or heteroatom group is independently selected from $C_{1-6}$ alkyl substituted, $C_{3-8}$ cycloalkyl substituted or unsubstituted C(=O)NH, C(=O)O, $C_{1-6}$ alkyl substituted or $C_{3-8}$ cycloalkyl substituted or unsubstituted NH, O, S, $C_{1-6}$ alkyl substituted or $C_{3-8}$ cycloalkyl substituted or unsubstituted C=NH, C=O, C=S, S(=O) and/or $S(=O)_2$, wherein the number of substituent, heteroatom or heteroatom group is arbitrary as long as chemical stability is achievable;

T is selected from C or a single bond of linkage, and $R_2$ and $R_3$ are none when T is a single bond of linkage;

M is selected from $C(Y)(R_{1a})$ when Q is selected from $C(R_{1b})(R_{1c})$, or M is selected from $C(R_{1b})(R_{1c})$ when Q is selected from $C(Y)(R_{1a})$;

Y is selected from $-(CH_2)_{r4}(G)_{r5}(CH_2)_{r6}-Y_1$, wherein $Y_1$ is selected from —O-E or a structure of formula ($Y_2$),

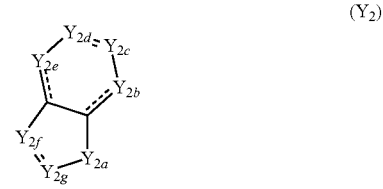

($Y_2$)

G is selected from halogen-substituted, hydroxy-substituted, amino-substituted or unsubstituted $CH_2$, $C_{1-6}$ alkyl substituted, $C_{3-8}$ cycloalkyl substituted or unsubstituted NH, O, S, S(=O), $S(=O)_2$, C(=O) or C(=S), wherein the number of substituent is arbitrary as long as chemical stability is achievable;

$r_4$ and $r_6$ are independently selected from 0, 1 or 2, $r_5$ is selected from 0 or 1, and when $r_4$, $r_5$ and $r_6$ are all 0, it means the corresponding structure is a single bond of linkage;

E is selected from optionally substituted 5-6 membered cyclohydrocarbyl or heterocyclic group, wherein the substituent is selected from F, Cl, Br, I, CN, =O, =S, OH, SH, $NH_2$, halogen-substituted, hydroxy-substituted, amino-substituted or unsubstituted $C_{1-6}$ alkyl or heteroalkyl or alkyl hetero group or heteroalkyl hetero group, halogen-substituted, hydroxy-substituted, amino-substituted or unsubstituted $C_{3-8}$ cyclic group or heterocyclic group or cyclic hetero group or heterocyclic hetero group, wherein the hetero atom or heteroatom group is independently selected from $C_{1-6}$ alkyl substituted, $C_{3-8}$ cycloalkyl substituted or unsubstituted C(=O)NH, C(=O)O, $C_{1-6}$ alkyl substituted or $C_{3-8}$ cycloalkyl substituted or unsubstituted NH, O, S, $C_{1-6}$ alkyl substituted or $C_{3-8}$ cycloalkyl substituted or unsubstituted C=NH, C=O, C=S, S(=O) and/or $S(=O)_2$, wherein the number of substituent, heteroatom or heteroatom group is arbitrary as long as chemical stability is achievable;

each of $Y_{2a}$, $Y_{2b}$, $Y_{2c}$, $Y_{2d}$, $Y_{2e}$, $Y_{2f}$ and $Y_{2g}$ is selected from optionally substituted $CH_2$, CH, NH, or is selected from N, O, S, S(=O), S(=O)$_2$, C(=O) or C(=S), and at least one of $Y_{2a}$, $Y_{2b}$, $Y_{2c}$, $Y_{2d}$, $Y_{2e}$, $Y_{2f}$, and $Y_{2g}$ is optionally substituted CH, CH$_2$ or NH, wherein the substituent is selected from F, Cl, Br, I, CN, =O, =S, OH, SH, NH$_2$, halogen-substituted, hydroxy-substituted, amino-substituted or unsubstituted C$_{1-6}$ alkyl or heteroalkyl or alkyl hetero group or heteroalkyl hetero group, halogen-substituted, hydroxy-substituted, amino-substituted or unsubstituted C$_{3-8}$ cyclic group or heterocyclic group or cyclic hetero group or heterocyclic hetero group, wherein the hetero atom or heteroatom group is independently selected from C$_{1-6}$ alkyl substituted, C$_{3-8}$ cycloalkyl substituted or unsubstituted C(=O)NH, C(=O)O, C$_{1-6}$ alkyl substituted or C$_{3-8}$ cycloalkyl substituted or unsubstituted NH, O, S, C$_{1-6}$ alkyl substituted or C$_{3-8}$ cycloalkyl substituted or unsubstituted C=NH, C=O, C=S, S(=O) and/or S(=O)$_2$, wherein the number of substituent, heteroatom or heteroatom group is arbitrary as long as chemical stability is achievable;

------ represents a single bond or a double bond;

each of $R_{1a}$, $R_{1b}$, $R_{1c}$, $R_2$, and $R_3$ is independently selected from H, F, Cl, Br, I, CN, =O, =S, OH, SH, NH$_2$, halogen-substituted, hydroxy-substituted, amino-substituted or unsubstituted C$_{1-6}$ alkyl or heteroalkyl or alkyl hetero group or heteroalkyl hetero group, halogen-substituted, hydroxy-substituted, amino-substituted or unsubstituted C$_{3-8}$ cyclic group or heterocyclic group or cyclic hetero group or heterocyclic hetero group, wherein the hetero atom or heteroatom group is independently selected from C$_{1-6}$ alkyl substituted, C$_{3-8}$ cycloalkyl substituted or unsubstituted C(=O)NH, C(=O)O, C$_{1-6}$ alkyl substituted or C$_{3-8}$ cycloalkyl substituted or unsubstituted NH, O, S, C$_{1-6}$ alkyl substituted or C$_{3-8}$ cycloalkyl substituted or unsubstituted C=NH, C=O, C=S, S(=O) and/or S(=O)$_2$, wherein the number of substituent, heteroatom or heteroatom group is arbitrary as long as chemical stability is achievable; or $R_2$ and $R_3$ are optionally connected to form a ring; and the compound or the pharmaceutically acceptable salt thereof comprises one or more chiral center.

Preferably, in the above compound or the pharmaceutically acceptable salt thereof, A is selected from a structure unit as shown in formula ($A_1$) or ($A_2$):

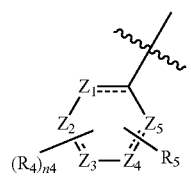

($A_1$)

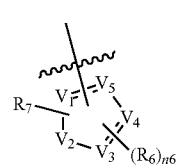

($A_2$)

wherein:

$Z_1$, $Z_2$, $Z_3$, $Z_4$, and $Z_5$ are independently selected from halogen-substituted, hydroxy-substituted, amino-substituted or unsubstituted CH or CH$_2$, or C$_{1-6}$ alkyl substituted or C$_{3-8}$ cycloalkyl substituted or unsubstituted C(=O)NH or NH, C=N, N, O, S, S(=O), S(=O)$_2$, C(=O)O, C(=O) or C(=S), wherein the number of substituent is arbitrary as long as chemical stability is achievable;

$V_1$, $V_2$, $V_3$, $V_4$, and $V_5$ are independently selected from halogen-substituted, hydroxy-substituted, amino-substituted or unsubstituted CH or CH$_2$, C$_{1-6}$ alkyl substituted or C$_{3-8}$ cycloalkyl substituted or unsubstituted C(=O)NH or NH, C=N, C, N, O, S, S(=O), S(=O)$_2$, C(=O)O, C(=O) or C(=S), and at least one of $V_1$ to $V_5$ is C or N, wherein the number of substituent is arbitrary as long as chemical stability is achievable;

------ represents a single bond or a double bond;

$R_4$ and $R_6$ are independently selected from H, F, Cl, Br, I, CN, =O, =S, OH, SH, NH$_2$, halogen-substituted, hydroxy-substituted, amino-substituted or unsubstituted C$_{1-6}$ alkyl or heteroalkyl or alkyl hetero group or heteroalkyl hetero group, halogen-substituted, hydroxy-substituted, amino-substituted or unsubstituted C$_{3-8}$ cyclic group or heterocyclic group or cyclic hetero group or heterocyclic hetero group, wherein the hetero atom or heteroatom group is independently selected from C$_{1-6}$ alkyl substituted, C$_{3-8}$ cycloalkyl substituted or unsubstituted C(=O)NH, C(=O)O, C$_{1-6}$ alkyl substituted or C$_{3-8}$ cycloalkyl substituted or unsubstituted NH, O, S, C$_{1-6}$ alkyl substituted or C$_{3-8}$ cycloalkyl substituted or unsubstituted C=NH, C=O, C=S, S(=O) and/or S(=O)$_2$, wherein the number of substituent, heteroatom or heteroatom group is arbitrary as long as chemical stability is achievable;

$R_5$ and $R_7$ are independently selected from optionally substituted 5-6 membered cyclohydrocarbyl or heterocyclic group, while the substituent is selected from F, Cl, Br, I, CN, =O, =S, OH, SH, NH$_2$, halogen-substituted, hydroxy-substituted, amino-substituted or unsubstituted C$_{1-6}$ alkyl or heteroalkyl or alkyl hetero group or heteroalkyl hetero group, halogen-substituted, hydroxy-substituted, amino-substituted or unsubstituted C$_{3-8}$ cyclic group or heterocyclic group or cyclic hetero group or heterocyclic hetero group, wherein the hetero atom or heteroatom group is independently selected from C$_{1-6}$ alkyl substituted, C$_{3-8}$ cycloalkyl substituted or unsubstituted C(=O)NH, C(=O)O, C$_{1-6}$ alkyl substituted or C$_{3-8}$ cycloalkyl substituted or unsubstituted NH, O, S, C$_{1-6}$ alkyl substituted or C$_{3-8}$ cycloalkyl substituted or unsubstituted C=NH, C=O, C=S, S(=O) and/or S(=O)$_2$, wherein the number of substituent, heteroatom or heteroatom group is arbitrary as long as chemical stability is achievable;

$n_4$ is selected from 0, 1, 2, 3, 4; and $n_6$ is selected from 0, 1, 2, 3.

Preferably, in the above compound or the pharmaceutically acceptable salt thereof, the structure unit

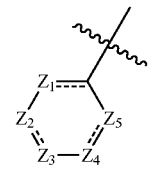

is selected from phenyl or pyridyl;

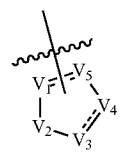

is selected from furyl, thienyl or thiazolyl.

Preferably, in the above compound or the pharmaceutically acceptable salt thereof, formula (A$_2$) is selected from a structure of formula (A$_{21}$):

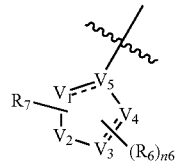

(A$_{21}$)

wherein V$_1$, V$_2$, V$_3$, V$_4$, V$_5$, R$_6$, R$_7$ and n$_6$ are defined as in formula (A$_2$).

Preferably, in the above compound or the pharmaceutically acceptable salt thereof, A is selected from a structure unit of formula (A$_{22}$):

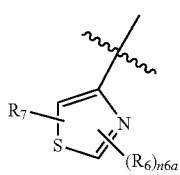

(A$_{22}$)

wherein R$_6$ and R$_7$ are defined as in formula (A$_2$); and n$_{6a}$ is selected from 0, 1 or 2.

Preferably, in the above-mentioned compound or the pharmaceutically acceptable salt thereof, the 5-6 membered cyclohydrocarbyl or heterocyclic group are independently selected from phenyl, pyridyl, furyl, thienyl, thiazolyl, pyrimidinyl, pyrazolyl, 1,2,3-triazolyl or 1,2,5-triazolyl.

Preferably, in the above compound or the pharmaceutically acceptable salt thereof, A is selected from:

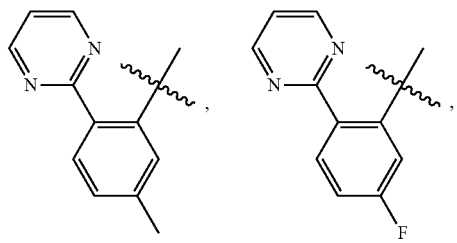

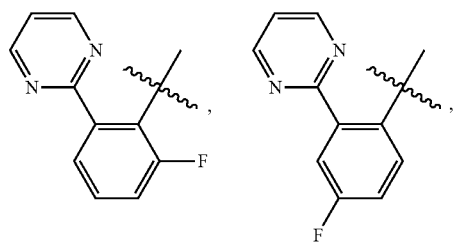

-continued

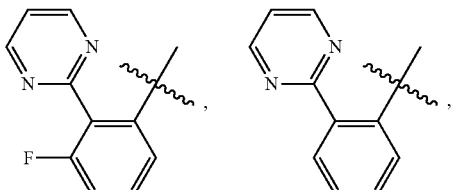

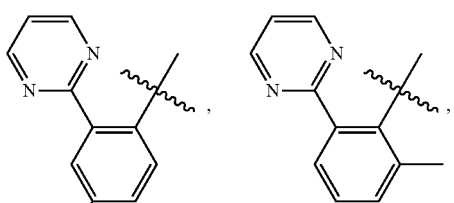

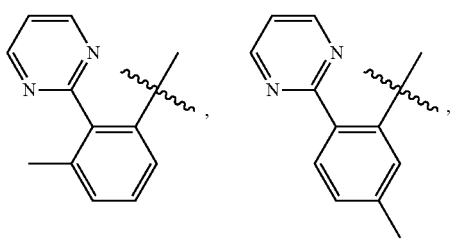

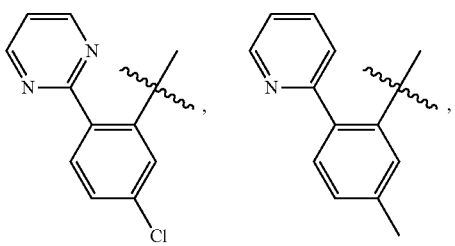

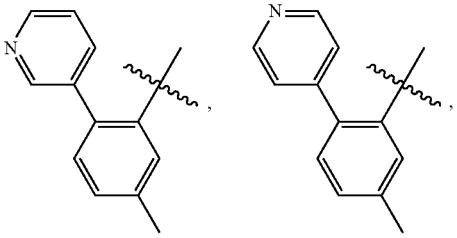

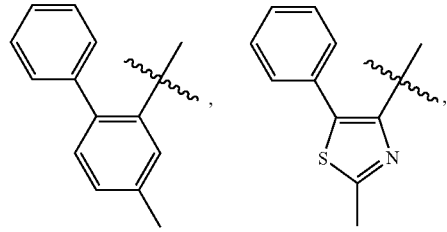

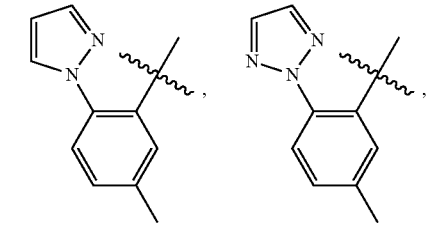

-continued

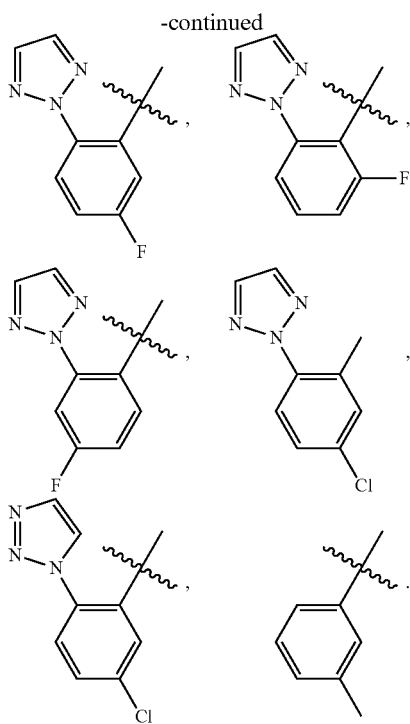

Preferably, in the above compound or the pharmaceutically acceptable salt thereof, formula ($Y_2$) is selected from a structure of formula ($Y_{21}$):

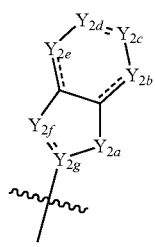

wherein $Y_{2a}$, $Y_{2b}$, $Y_{2c}$, $Y_{2d}$, $Y_{2e}$, $Y_{2f}$ and $Y_{2g}$ are defined as in formula (I).

Preferably, in the above compound or the pharmaceutically acceptable salt thereof, formula ($Y_{21}$) is selected from a structure of formula ($Y_{22}$) which is optionally substituted:

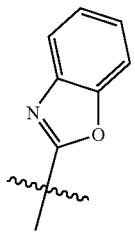

wherein the substituent is selected from F, Cl, Br, I, CN, =O, =S, OH, SH, $NH_2$, halogen-substituted, hydroxy-substituted, amino-substituted or unsubstituted $C_{1-6}$ alkyl or heteroalkyl or alkyl hetero group or heteroalkyl hetero group, halogen-substituted, hydroxy-substituted, amino-substituted or unsubstituted $C_{3-8}$ cyclic group or heterocyclic group or cyclic hetero group or heterocyclic hetero group, wherein the hetero atom or heteroatom group is independently selected from $C_{1-6}$ alkyl substituted, $C_{3-8}$ cycloalkyl substituted or unsubstituted C(=O)NH, C(=O)O, $C_{1-6}$ alkyl substituted or $C_{3-8}$ cycloalkyl substituted or unsubstituted NH, O, S, $C_{1-6}$ alkyl substituted or $C_{3-8}$ cycloalkyl substituted or unsubstituted C=NH, C=O, C=S, S(=O) and/or S(=O)$_2$, wherein the number of substituent, heteroatom or heteroatom group is arbitrary as long as chemical stability is achievable.

Preferably, in the above compound or the pharmaceutically acceptable salt thereof, Y is selected from optionally substituted

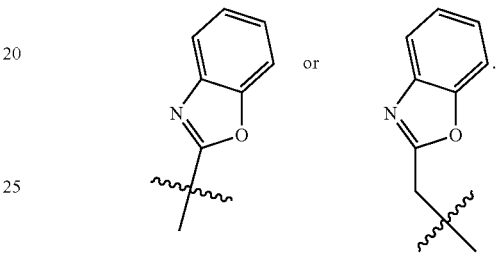

Preferably, in the above compound or the pharmaceutically acceptable salt thereof, Y is selected from —$CH_2$—O-E or —O-E, wherein E is defined as in formula (I).

Preferably, in the above compound or the pharmaceutically acceptable salt thereof, E is selected from a structure unit of formula ($E_a$):

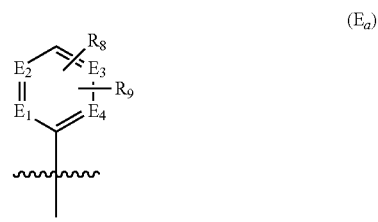

wherein:

$E_1$, $E_2$, $E_3$, and $E_4$ are independently selected from halogen-substituted, hydroxy-substituted, amino-substituted or unsubstituted CH, N; and $R_8$ and $R_9$ are independently selected from H, F, Cl, Br, I, CN, =O, =S, OH, SH, $NH_2$, halogen-substituted, hydroxy-substituted, amino-substituted or unsubstituted $C_{1-6}$ alkyl or heteroalkyl or alkyl hetero group or heteroalkyl hetero group, halogen-substituted, hydroxy-substituted, amino-substituted or unsubstituted $C_{3-8}$ cyclic group or heterocyclic group or cyclic hetero group or heterocyclic hetero group, wherein the hetero atom or heteroatom group is independently selected from $C_{1-6}$ alkyl substituted, $C_{3-8}$ cycloalkyl substituted or unsubstituted C(=O)NH, C(=O)O, $C_{1-6}$ alkyl substituted or $C_{3-8}$ cycloalkyl substituted or unsubstituted NH, O, S, $C_{1-6}$ alkyl substituted or $C_{3-8}$ cycloalkyl substituted or unsubstituted C=NH, C=O, C=S, S(=O) and/or S(=O)$_2$, wherein the number of substituent, heteroatom or heteroatom group is arbitrary as long as chemical stability is achievable.

Preferably, in the above compound or the pharmaceutically acceptable salt thereof, the structure unit

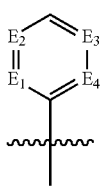

is defined into phenyl or pyridyl, or is replaced with thienyl or furyl.

Preferably, in the above compound or the pharmaceutically acceptable salt thereof, Y is selected from:

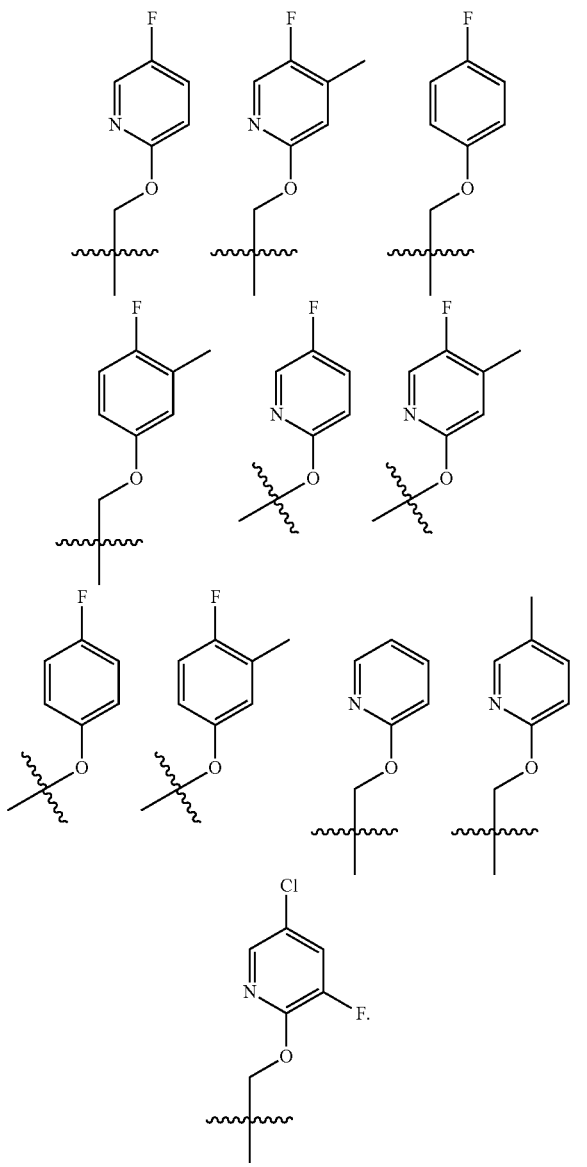

Preferably, in the above compound or the pharmaceutically acceptable salt thereof, U, X, and G are independently selected from NH or N($C_{1-6}$ alkyl).

Preferably, in the above compound or the pharmaceutically acceptable salt thereof, $R_{1a}$, $R_{1b}$, and $R_{1c}$ are independently selected from H, methyl, or fluoro.

Preferably, in the above compound or the pharmaceutically acceptable salt thereof, $R_2$ and $R_3$ are independently selected from H, methyl, fluoro or cyclopropyl.

Preferably, in the above compound or the pharmaceutically acceptable salt thereof, $R_2$ and $R_3$ together form 3-8 membered cycloalkyl.

Preferably, in the above compound or the pharmaceutically acceptable salt thereof, $R_2$ and $R_3$ together form cyclopropyl.

Preferably, in the above compound or the pharmaceutically acceptable salt thereof, the $C_{1-6}$ alkyl is selected from methyl, ethyl, propyl, butyl, pentyl, and hexyl, wherein propyl, butyl, pentyl, and hexyl are optionally cyclized or partially cyclized.

Preferably, the above compound or the pharmaceutically acceptable salt thereof has any of the following structures:

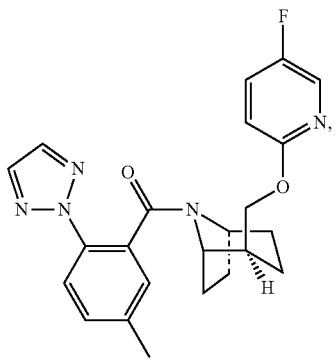

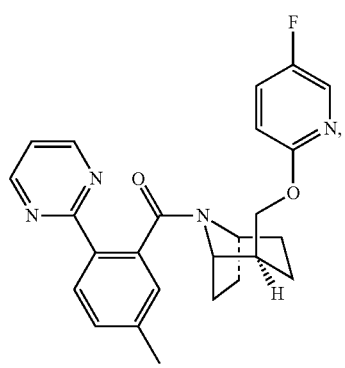

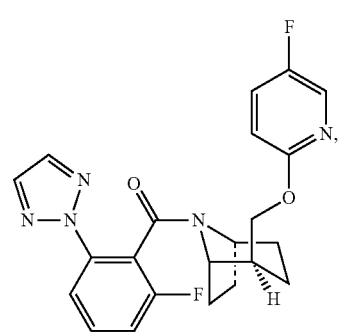

-continued
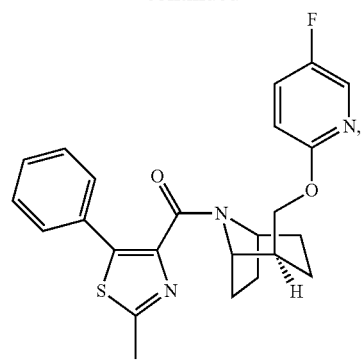
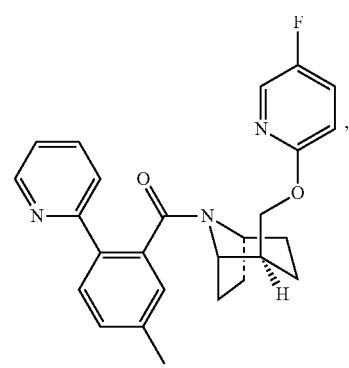
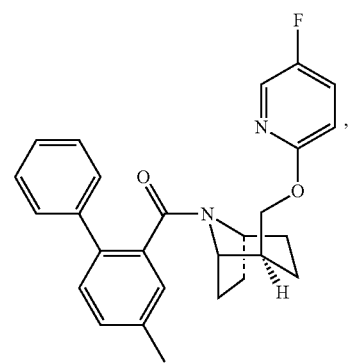
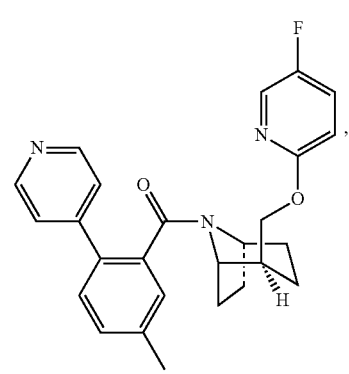
-continued
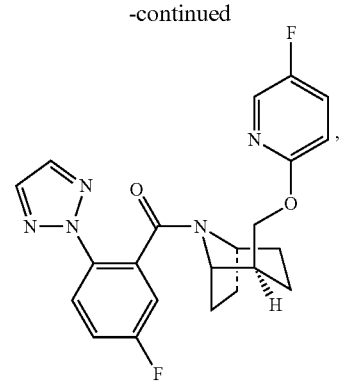
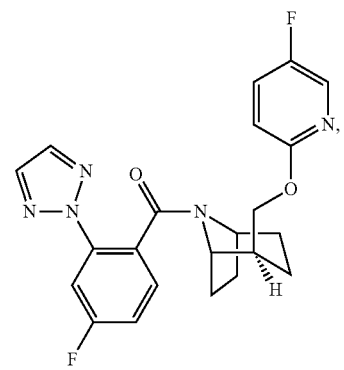
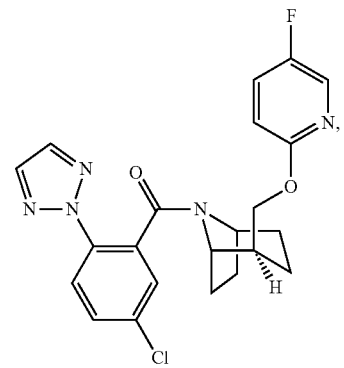
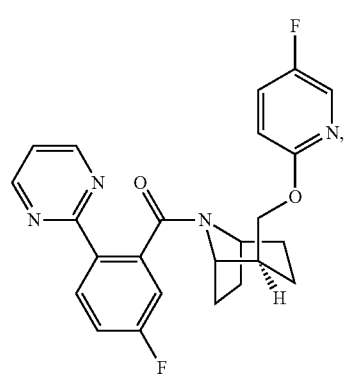

-continued

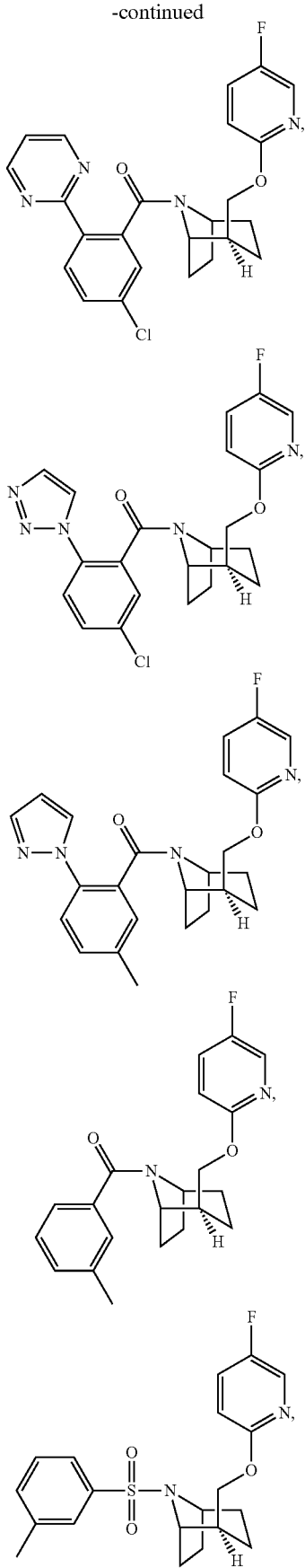

-continued

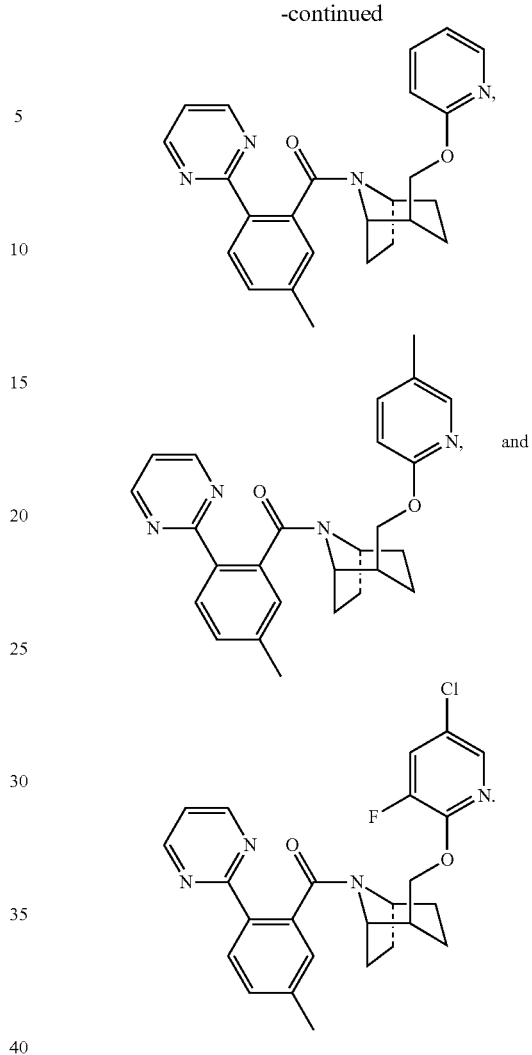

and

Another object of the present invention is to provide a pharmaceutical composition comprising a therapeutically effective amount of the above compound or a pharmaceutically acceptable salt thereof, and a pharmaceutically acceptable carrier.

Another object of the present invention is to provide a use of the above compound or the pharmaceutically acceptable salt thereof in preparing a medicament for treatment of insomnia, chronic obstructive pulmonary disease, obstructive sleep apnea, hypersomnia, anxiety, obsessive-compulsive disorder, panic attack, nicotine addiction, or binge eating disorder.

The term "pharmaceutically acceptable salt" refers to a salt of the compound of the present invention, which is prepared by a compound having the specific substituents provided in the present invention with a relatively nontoxic acid or base. When the compound of the present invention contains relatively acidic functional groups, base addition salts may be obtained by using a sufficient amount of base to contact with the neutral form of such compound in pure solution or suitable inert solvents. Pharmaceutically acceptable base addition salt comprises sodium, potassium, calcium, ammonium, organic amine, magnesium salt or the like. When the compound of the present invention contains relatively basic functional groups, acid addition salt may be obtained by using a sufficient amount of acid to contact with the neutral form of such compound in pure solution or suitable inert solvents. Examples of pharmaceutically acceptable acid addition salt comprises inorganic acid salts, wherein the inorganic acid comprises e.g., hydrochloric acid, hydrobromic acid, nitric acid, carbonate, bicarbonate, phosphate, hydrogen phosphate, dihydrogen phosphate, sulfate, bisulfate, hydroiodic, phosphorous and the like; and organic acid salts, wherein the organic acid comprises e.g., acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluene sulfonic acid, citric acid, tartaric acid and methanesulfonic acid, and the like. Further, it includes salt of amino acids (such as arginine, etc.), and salt of organic acids such as glucuronic acid, etc. (see Berge et al., "Pharmaceutical Salts", Journal of Pharmaceutical Science 66: 1-19 (1977)). Certain compounds of the present invention contain both basic and acidic functional groups, so they can be converted into either base or acid addition salts.

Preferably, the compound is contacted with a base or an acid in conventional manner, and the parent compound is isolated, thereby regenerating a neutral form of compound. The difference of the form of the parent compound and its various forms of salt is certain physical properties, for example, the different solubility in polar solvents.

As used herein, "pharmaceutically acceptable salt" is a derivative of the compound of the present invention, wherein the parent compound is modified by salt formation with an acid or with a base. Examples of pharmaceutically acceptable salts include, but are not limited to: inorganic or organic acid salt of basic groups such as amines, alkali metal or organic salts of acid radicals such as carboxylic acid. The pharmaceutically acceptable salts include conventional non-toxic salts or quaternary ammonium salts of the parent compound, such as salts formed with non-toxic inorganic or organic acid. Conventional non-toxic salts include, but are not limited to those derived from inorganic acids and organic acids, said inorganic or organic acid selected from 2-acetoxybenzoic acid, 2-oxyethylsulfonic acid, acetic acid, ascorbic acid, benzenesulfonic acid, benzoic acid, bicarbonate, carbonate, citric acid, edetic acid, ethanedisulfonic acid, ethanesulfonic acid, fumaric acid, glucoheptonate, gluconic acid, glutamic acid, glycolic acid, hydrobromic acid, hydrochloric acid, hydrogen iodide, hydroxyl, hydroxylnaphthalene, isethionic acid, lactic acid, lactose, lauryl acid, maleic acid, malic acid, mandelic acid, loprazolam, nitric acid, oxalic acid, pamoic acid, pantothenic acid, phenylacetic acid, phosphoric acid, polygalacturonic acid, propionic acid, salicylic acid, stearic acid, ethylene acetic acid, succinic acid, sulfamic acid, sulfanilic acid, sulfuric acid, tannin, tartaric acid and p-toluene sulfonic acid.

The pharmaceutically acceptable salts of the present invention may be synthesized by using a parent compound containing acid radical or basic group with a conventional chemical method. In general, the preparation method of such salts includes: in water or organic solvent or the mixture thereof, the compound in free acid or base form reacts with a stoichiometric amount of appropriate base or acid. Generally, non-aqueous mediums such as ether, ethyl acetate, ethanol, isopropanol, or acetonitrile are preferred.

In addition to salt form, the compound of the present invention can be provided in prodrug form. A prodrug of the compound described herein can readily undergo chemical changes under physiological conditions to convert into the compound of the present invention. Additionally, prodrugs can be converted by chemical or biochemical methods in in vivo environment into the compound of invention.

Certain compounds of the present invention may be in non-solvation form or solvation form, including hydrated form. Generally, the solvation form and non-solvation form are comparative, and are both within the scope of the present invention. Certain compounds of the present invention may exist in polycrystal or amorphous form.

Certain compounds of the present invention may have asymmetric carbon atoms (optical centers) or double bonds. Racemates, diastereomers, geometric isomers and individual isomers are within the scope of the present invention.

Unless otherwise specified, the term "substituted" refers to any one or more hydrogen atom on particular atoms is (are) substituted by a substituent, including deuterium and variants of hydrogen, as long as the particular atom is of normal valence and the compound is stable after substitution. When a substituent is ketone group (i.e., =O), it means that two hydrogen atoms are replaced. Ketone group substitution does not occur on the aromatic group. The term "optionally substituted" means that it may be substituted, or may be unsubstituted. Unless otherwise specified, the type and number of substituents may be arbitrary as long as it is chemically achievable.

Unless otherwise specified, when any variable (e.g., R) occurs more than once in the composition or structure of the compound, its definition in each case are independent. Thus, for example, if a group is substituted with 0-2 of R, then the group may optionally be substituted with up to two R, and R in each case can be independent. In addition, the combination of substituents and/or the variants thereof is allowed only if such combination results in a stable compound.

When one of the variables is selected from a single bond, it means that the two groups connected are directly connected. For example, when L represents a single bond, A-L-Z means that the structure is actually A-Z.

Unless otherwise specified, when a bond of a group or a substituent can be cross-connected to two atoms on a ring, the group or substituent can be bonded to any atom of the ring. If the atom in the exemplified group or substituent connected to the general chemical structure is not specified when a particular compound is not mentioned, the group or substituent may be bonded via any atom. A combination of groups or substituents and/or the variants thereof is allowed only if such combination results in a stable compound. For example, structure unit

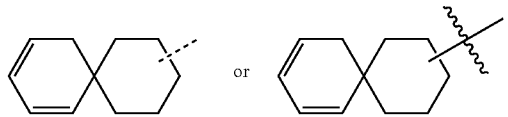

represent that the substitution can be happened in any position of the cyclohexyl or cyclohexadiene. Unless otherwise specified, the term "hydrocarbyl" or the specific concept (such as alkyl, alkenyl, alkynyl, phenyl, etc.) by itself or as a part of another substituent represents a straight, branched or cyclic hydrocarbon radical or combinations thereof, may be fully saturated, mono- or poly-unsaturated, may be mono-, di- or poly-substituted, and may include divalent or multivalent radicals, and has certain number of carbon atoms (for example, C1-C10 indicates 1 to 10 carbons). The hydrocarbon groups include aliphatic hydrocarbon groups and aromatic hydrocarbon groups. The aliphatic hydrocarbon groups include linear and cyclic groups, and include but are not limited to alkyl group, alkenyl group, and alkynyl group; the aromatic hydrocarbon groups include but are not limited to 6-12 membered aromatic hydrocarbon groups, such as benzene, naphthalene and the like. In some embodiments, the term "alkyl" represents linear, branched or cyclic radicals or the combinations thereof, which may be fully saturated, mono- or poly-unsaturated and can include di- or multivalent radicals. Examples of saturated hydrocarbon radicals include, but are not limited to, methyl, ethyl, n-propyl, isopropyl, n-butyl, isobutyl, sec-butyl, isobutyl, cyclohexyl, (cyclohexyl) methyl, cyclopropylmethyl, and homologs or isomers of n-pentyl, n-hexyl, n-heptyl, n-octyl radicals. Unsaturated alkyl groups have one or more double or triple bonds, examples of which include but are not limited to, ethenyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless otherwise specified, the hetero hydrocarbon group, heterocyclic group, hydrocarbon hetero group, cyclic hetero group, hetero hydrocarbon hetero group, heterocyclic hetero group mean that there is hetero atom or hetero atom group on a particular group, wherein the hetero atom or hetero atom group includes but is not limited to N, NH, substituted or protected NH, O, S, S (=O), S(=O)$_2$. The hetero hydrocarbon group or heterocyclic group connects with the rest of the molecule via a carbon atom, that is to say, the hetero atom can be located at any interior position of the group but not at the position attached to the remainder of the molecule; the hydrocarbon hetero group or cyclic hetero group connects to the rest of the molecule via a heteroatom, that is to say, the heteroatom is located in the position attached to the remainder of the molecule; and the hetero hydrocarbon hetero group or heterocyclic hetero group connects to the rest of the molecule via a heteroatom, and the hetero atom may be located at any interior position of the group including the position attached to the rest of the molecule.

Unless otherwise specified, the term "heterohydrocarbyl", or the specific concepts thereof (e.g. heteroalkyl, heteroalkenyl, heteroalkynyl, heteroaryl, etc.) by itself or in combination with other terms indicates a stable straight chain, branched chain or cyclic hydrocarbon radical, or the combinations thereof and comprises a certain number of carbon atoms and at least one hetero atoms. In some embodiments, the term "heterohydrocarbyl", or the specific concepts thereof (e.g. heteroalkyl, heteroalkenyl, heteroalkynyl, heteroaryl, etc.) by itself or in combination with other terms indicates a stable straight chain, branched chain, or the combinations thereof and comprises a certain number of carbon atoms and at least one hetero atoms. In one exemplary embodiment, a heteroatom is selected from B, O, N and S, wherein the nitrogen and sulfur atoms are optionally oxidized and the nitrogen atom is optionally quaternized. Heteroatoms B, O, N and S may be located on any interior position of heterohydrocarbyl (except the positions on which the hydrocarbon group attached to the remainder of the molecule). Embodiments comprise but are not limited to —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. Up to two heteroatoms may be consecutive, such as —CH$_2$—NH—OCH$_3$.

Unless otherwise specified, the terms "alkoxy", "alkylamino" and "alkylthio" (or thioalkoxy) are conventionally used terms which refer to an alkyl connected to the rest part of molecules via an oxygen atom, an amino group or a sulfur atom.

Unless otherwise specified, the terms "cycloalkyl", "heterocycloalkyl", "cyclic hydrocarbon hetero group" or a specific concept thereof (such as aryl, heteroaryl, aryl hetero, cycloalkyl, heterocycloalkyl, cycloalkyl hetero, cycloalkenyl, heterocycloalkenyl, cycloalkenyl hetero group, cycloalkynyl, heterocycloalkynyl, cycloalkynyl hetero group, etc.) by itself or in combination with other terms represent, respectively, a cyclized "hydrocarbon group", "heterohydrocarbyl" or "hydrocarbon hetero group". Examples of cycloalkyl include, but are not limited to, cyclopentyl, cyclohexyl, 1-cyclohexenyl, 3-cyclohexenyl, cycloheptyl and the like. Non-limiting examples of heterocyclic group include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuranindole-3-yl, tetrahydrothien-2-yl, tetrahydrothien-3-yl, 1-piperazinyl and 2-piperazinyl.

Unless otherwise specified, the term "halogen element" or "halo" by itself or as a part of another substituent denotes fluorine, chlorine, bromine or iodine atom. Furthermore, the term "haloalkyl" means to include monohaloalkyl and polyhaloalkyl. For example, the term "halo ($C_1$-$C_4$) alkyl" is intended to include, but not limited to, trifluoromethyl, 2,2,2-trifluoroethyl, 4-chlorobutyl and 3-bromopropyl and the like.

Unless otherwise specified, the term "aryl" means polyunsaturated aromatic hydrocarbon substituents, which may be mono-, di- or polysubstituted, it may be in single ring or multiple ring form (preferably 1-3 rings), fused together or linked covalently. The term "heteroaryl" refers to an aryl group (or ring) with one to four heteroatoms. In one exemplary embodiment, a heteroatom is selected from B, N, O and S, wherein the nitrogen and sulfur atoms are optionally oxidized and the nitrogen atom is optionally quaternized. The heteroaryl may connect to the other parts of molecular via heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituents for any of the above aryl and heteroaryl ring are selected from any of acceptable substituents described herein.

Unless otherwise specified, for simplicity, when used in combination with other terms (e.g. aryloxy group, arylthio group, arylalkyl group), the aryl group includes aryl or heteroaryl ring as defined above. Thus, the term "aralkyl" means to include those atomic groups in which aryl group is attached to an alkyl (e.g. benzyl, phenethyl, pyridylmethyl, etc.), and to include those groups in which the carbon atom (e.g., methylene group) has been replaced with e.g., oxygen, e.g., phenoxymethyl, 2-pyridyloxymethyl-3-(1-naphthyloxy)propyl, and the like.

Unless otherwise specified, "ring" represents a substituted or unsubstituted cycloalkyl, a substituted or unsubstituted heterocyclic alkyl, a substituted or unsubstituted aryl group or a substituted or unsubstituted heteroaryl. The ring includes a condensed ring. The number of ring atoms is usually defined as the member number in a ring, for example, "5 to 7-membered ring" means 5 to 7 atoms are arranged in a cycle. Unless otherwise specified, the ring optionally contains 1 to 3 hetero atoms. Therefore, "5 to 7-membered ring" includes for example, phenyl pyridine and piperidinyl; on the other hand, the term "5 to 7-membered heterocycloalkyl ring" include pyridyl and piperidyl, but excluding phenyl. The term "ring" also includes ring systems containing at least one ring, wherein each "ring" independently meets the above definition.

Unless otherwise specified, as used herein, the term "heteroatom" includes atoms other than carbon (C) and hydrogen (H), for example, including oxygen (O), nitrogen (N), sulfur (S), silicon (Si), germanium (Ge), aluminum (Al) and boron (B) and the like.

Unless otherwise specified, the term "leaving group" refers to a functional group or atom which can be substituted by another functional group or atom through substitution reaction (such as nucleophilic substitution reaction). For example, representative leaving groups include triflate; chlorine, bromine and iodine; sulphonate groups, such as mesylate, tosylate, brosylate, p-toluenesulfonic acid esters and the like; acyloxy groups, such as acetoxy, trifluoroacetoxy and the like.

Unless otherwise specified, the term "protecting group" includes, but is not limited to "amino protecting group", "hydroxy protecting group" or "mercapto-protecting group". The term "amino protecting group" means a protecting group suitable for blocking the amino nitrogen side-reactions. Representative amino protecting groups include, but are not limited to: formyl; acyl groups such as alkanoyl (e.g. acetyl, trichloroacetyl or trifluoroacetyl group); alkoxycarbonyl, such as tert-butoxycarbonyl (Boc); arylmethoxycarbonyl group such as benzyloxycarbonyl (Cbz) and 9-fluorenyl methoxycarbonyl (Fmoc); arylmethyl group such as benzyl (Bn), trityl (Tr), 1,1-di-(4'-methoxyphenyl) methyl; silyl groups such as trimethylsilyl group (TMS) and tert-butyldimethylsilyl (TBS) and the like. The term "hydroxy protecting group" means a protecting group suitable for blocking the hydroxy side-reactions. Representative hydroxy protecting groups include, but are not limited to: alkyl such as methyl, ethyl and t-butyl; acyl, e.g. alkanoyl group (e.g. acetyl); arylmethyl group such as benzyl (Bn), p-toluenesulfonic methoxybenzyl (PMB), 9-fluorenyl methyl (Fm), and diphenylmethyl (benzhydryl, DPM); silyl groups such as trimethylsilyl group (TMS) and tert-butyl dimethyl silyl (TBS) and the like.

Unless otherwise indicated, haloalkyl groups include, but are not limited to: trifluoromethyl, trichloromethyl, pentafluoroethyl, and pentachloroethyl. "Alkoxy" represents an alkyl group attached via an oxygen bridge and having the above specified carbon atom number. $C_{1-6}$ alkyoxy includes $C_1$, $C_2$, $C_3$, $C_4$, $C_5$ and $C_6$ alkyoxy. Examples of alkoxy include, but are not limited to: methoxy, ethoxy, n-propoxy, isopropoxy, n-butoxy, sec-butoxy, tert-butoxy, n-pentyloxy and S-pentoxy. "Cycloalkyl" includes saturated ring groups, such as cyclopropyl, cyclobutyl or cyclopentyl. 3-7 cycloalkyl includes $C_3$, $C_4$, $C_5$, $C_6$, $C_7$ and $C_6$ cycloalkyl. "Alkenyl" includes hydrocarbon chain in straight or branched chain configuration, where there are one or more carbon-carbon double bonds on stable sites of the chain, such as vinyl and propenyl.

Unless otherwise specified, the term "halogen" or "halo" refers to fluorine, chlorine, bromine and iodine.

Unless otherwise specified, the term "heterocycle" or "heterocyclic group" means a stable monocyclic ring or bicyclic ring or bicyclic heterocyclic ring which may be saturated, partially unsaturated or unsaturated (or aromatic), and comprises carbon atoms and 1, 2, 3 or 4 ring heteroatoms independently selected from N, O and S, wherein said heterocyclic ring may optionally fused to a benzene ring to form a bicyclic.

Unless otherwise specified, examples of the heterocyclic compounds include, but are not limited to: acridinyl, azocinoyl, benzimidazolyl, benzofuranyl, benzomercaptofuryl, benzomercaptobenzyl, benzoxazolyl, benzooxazolinyl, benzothiazolyl, benzotriazolyl, benzotetrazolyl, benzo-isoxazolyl, benzo-isothiazole, benzo-imidazolyl, carbazolyl, 4aH-carbazolyl, carbolinyl, chromanyl, chromene, cinnolinyl tetrahydroquinolinyl, 2H, 6H-1,5,2-dithiazinyl, dihydrofuranyl [2, 3-b] tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatino group, isobenzofuran, pyranyl, isoindolyl, isoindolinyl, isoindolyl, indolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isoxazolyl, oxindole, pyrimidinyl, phenanthridinyl, phenanthrolinyl, phenazinyl, phenothiazinyl, benzoxanthinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridinoxazolyl, pyridinoimidazole, pyridinothiazole, pyridine, pyrimidinyl, pyrrolidinyl, pyrrolinyl, 2H-pyrrolyl, pyrrolyl, pyrazolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazolyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thienoxazolyl, thienothiazolyl, thienoimidazolyl, thienyl, triazinyl, 1,2,3-triazolyl, 1,2,4-triazolyl, 1,2,5-triazolyl, 1,3,4-triazolyl, and xanthenyl. It further includes fused and spiro ring compounds. Unless otherwise specified, the compounds of the present invention may be prepared by various synthetic methods well known to those skilled in the art, including the specific embodiments enumerated below, embodiments in conjunction with other methods of chemical synthesis, and the equivalents familiar for the skilled in the art. The preferred embodiments include but are not limited to the examples of the present invention.

Unless otherwise specified, the structure of the compound is determined by nuclear magnetic resonance (NMR) and/or liquid mass spectrometry (LCMS). NMR chemical shift (δ) are provided in $10^{-6}$ (ppm) unit. NMR is measured by Bruker AVANCE-400 NMR instrument, measuring solvent comprises deuterated dimethylsulfoxide (DMSO-$d_6$), deuterated chloroform (CDCl$_3$), or deuterated methanol (CD$_3$OD), and the internal standard is tetramethylsilane (TMS).

Unless otherwise specified, the determination of absolute configuration is conducted by conventional method single crystal X-Ray diffraction measurement. For example, in the determination of absolute configuration of compounds 1-16, equipment used was Bruker APEX-II CCD, temperature was 296K, radiation wavelength was 1.54178, radiation type was Cu-Ka, and the test results were shown in Figur 1.

Unless otherwise specified, the liquid chromatogram of liquid mass spectrometry LCMS was conducted by using Agilent 1200 (Xtimate C18 2.1*30 mm column), and mass spectrometry was conducted by using Agilent 6110 (Ion source: ESI).

Unless otherwise specified, the HPLC determination was conducted by using Shimadzu LC10AD high pressure liquid chromatography (Xtimate C18 2.1*30 mm column).

Unless otherwise stated, the plates used in thin layer chromatography was Yantai Huanghai HSGF254 silica gel plates or Qingdao GF254 silica gel plates and silica gel plates used in thin layer chromatography (TLC) were 0.15 mm-0.2 mm. The plates used in thin layer chromatography separation and purification were 0.4 mm-0.5 mm.

Unless otherwise stated, column chromatography on silica gel generally uses Yantai Huanghai 200-300 mesh silica gel as a carrier.

Unless otherwise specified, the known starting materials of the present invention may be synthesized by methods known in the art, or may be purchased from ABCR GmbH & Co. KG, Acros Organics, Aldrich Chemical Company, TCI, Alfa, Accela ChemBio Inc, Ouhechem Inc. and other companies.

Unless otherwise specified, when there is no specific instruction in the embodiments, the reactions can be carried out both in argon atmosphere or nitrogen atmosphere. Argon or nitrogen atmosphere means that the reaction flask is connected to an argon or nitrogen balloon in 1 L volume.

Unless otherwise specified, hydrogen atmosphere means that the reaction flask is connected to a hydrogen balloon in 1 L volume.

Unless otherwise specified, the pressured hydrogenation uses Parr 3916EKX type hydrogenation apparatus and QingLan QL-500 type hydrogen generator or HC2-SS-type hydrogenation instrument. The hydrogenation reaction is usually evacuated, filled with hydrogen, and repeated for three times.

Unless otherwise specified, the microwave reaction uses a CEM Discover-S 908860 microwave or Biotage Initiator 60 microwave reactor.

Unless otherwise specified, when there is no specific instruction in the embodiments, the solution refers to aqueous solution.

Unless otherwise specified, when there is no specific instruction in the embodiments, the reaction temperature is room temperature, which is 20° C. to 30° C.

Unless otherwise specified, the monitoring of the reaction process is conducted by thin layer chromatography (TLC), the developing agent systems used in the reactions of are: A: methylene chloride and methanol system, B: n-hexane and ethyl acetate, C: petroleum ether and ethyl acetate system, D: acetone, wherein the volume ratio of the solvent is adjusted according to the different polarity of the compound.

Unless otherwise specified, the eluent systems used in column chromatography and the developing agent systems in thin layer chromatography column chromatography used in the purification of compounds include: A: methylene chloride and methanol system, B: petroleum ether and ethyl acetate system, C: methylene chloride and acetone system, wherein the volume ratio of the solvent is adjusted according to the different polarity of the compound, and a small amount of basic or acidic agent such as triethylamine or acetic acid can be used for conditioning.

Unless otherwise specified, the equipment used in HPLC separation is Shimadzu LC-8A Prep.; the separation column is Phenomenex Luna C18 250*50 mm, 10 μm; mobile phase is respectively A: Water (0.2% FA), B: $CH_3CN$; wherein the mobile phase gradient (0-100% B) is determined according to the different polarity of the compound; isolating time is 25 min; flowing rate is 90 mL/min; and Detection wavelength is: 220/254 nm.

The present invention will be further illustrated below with reference to the specific examples which are not to limit the scope of the invention.

Unless otherwise specified, the solvents used in the present invention are commercially available, and can be used without further purification.

Unless otherwise specified, the present invention adopts the following abbreviations: aq represents water; HATU represents O-(7-azabenzotriazol-1-yl)-N, N, N',N'-tetramethylurea hexafluorophosphate; EDC represents N-(3-dimethylaminopropyl)-N'-ethylcarbodiimide hydrochloride; m-CPBA represents 3-chloroperoxybenzoic acid; eq represents equivalents or equal amount; CDI represents carbonyl diimidazole; DCM represents dichloromethane; PE represents petroleum ether; DIAD represents diisopropyl azodicarboxylate; DMF represents N, N-dimethylformamide; DMSO represents dimethylsulfoxide; EtOAc represents ethyl acetate; EtOH represents ethanol; MeOH represents methanol; CBz represents benzyloxycarbonyl, which is an amine protecting group; BOC represents t-butyl carbonyl group, which is an amine protecting group; HOAc represents acetic acid; $NaCNBH_3$ represents sodium cyanoborohydride; RT represents room temperature; O/N represents overnight; THF represents tetrahydrofuran; $Boc_2O$ represents tert-butyl dicarbonate; TFA represents trifluoroacetic acid; DIPEA represents diisopropylethylamine; $SOCl_2$ represents chloride sulfone; $CS_2$ represents carbon disulfide; TsOH represents p-toluenesulfonic acid; NFSI represents N-fluoro-N-(phenylsulfonyl) benzenesulfonamide; NCS represents 1-chloropyrrolidine-2,5-dione; n-$Bu_4NF$ represents tetrabutylammonium fluoride; iPrOH represents 2-propanol; mp represents melting point.

Unless otherwise specified, the compounds are named by human or ChemDraw® software, and vendor directory names are used for the commercially available compounds.

When compared to the existing technology, the compounds of the present invention have high efficiency and low toxicity, and show significant, even unexpected progress in the activity, half-life, solubility, pharmacokinetic and other aspects, so that they are very suitable for pharmaceutical uses.

EMBODIMENTS FOR CARRYING OUT THE INVENTION

The present invention will be further illustrated below with reference to the specific examples, but these examples are not to make any disadvantage limitation to the invention. This invention has been described in detail herein, and the embodiments for carrying out the invention are disclosed. It would be obvious for those skilled in the art can to make various changes and modifications to the embodiments for carrying out the present invention without departing from the spirit and scope of the present invention.

Examples 1 and 2
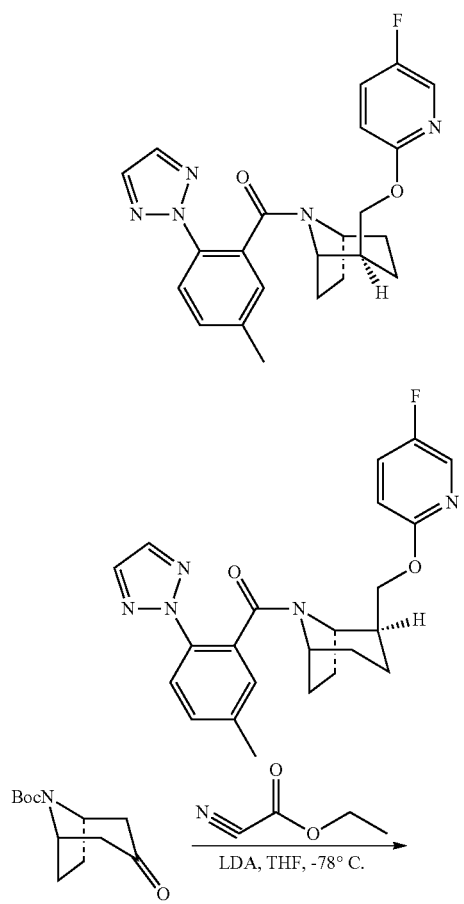
1-16
2-1
1-1
1-3
(Cis/trans isomeric mixture)
1-4
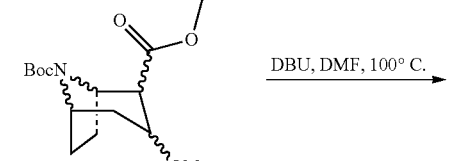
1-5
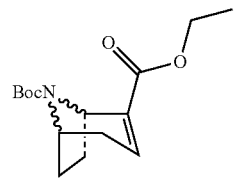
1-6
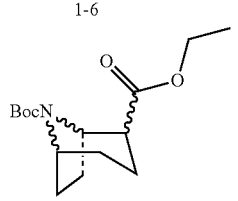
1-7
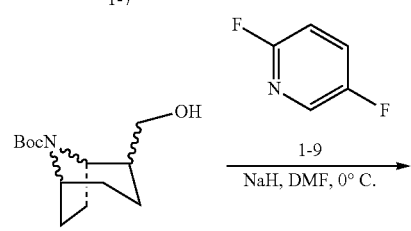
1-8
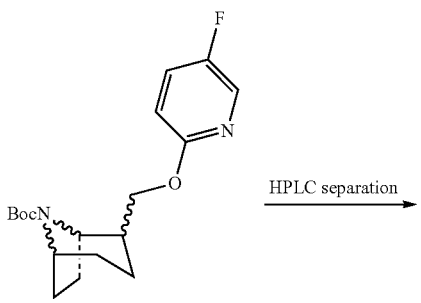
1-10
(Cis/trans isomeric mixture)
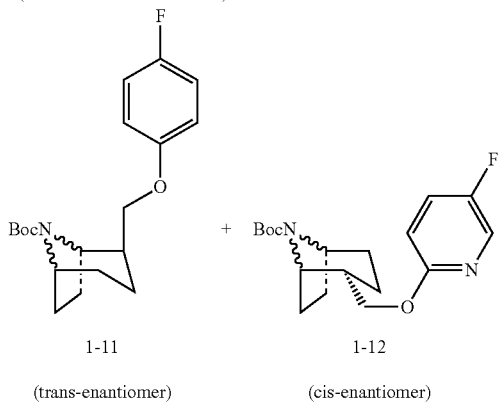
1-11 (trans-enantiomer)   1-12 (cis-enantiomer)

27
-continued

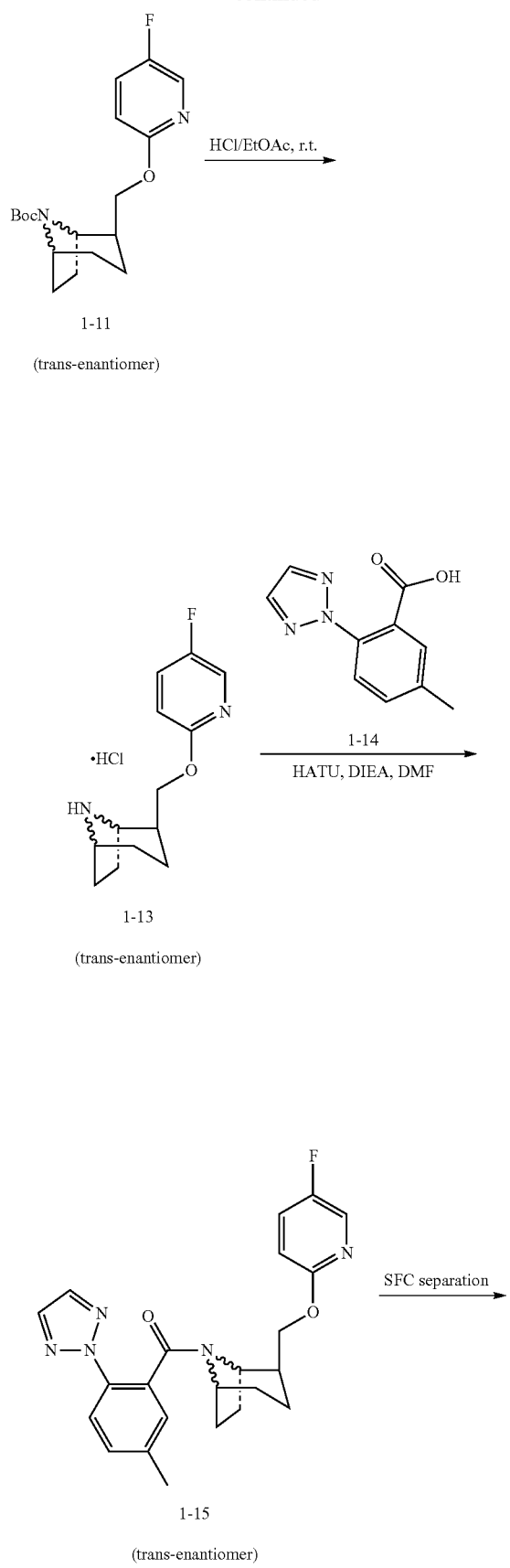

1-11
(trans-enantiomer)

1-13
(trans-enantiomer)

1-15
(trans-enantiomer)

28
-continued

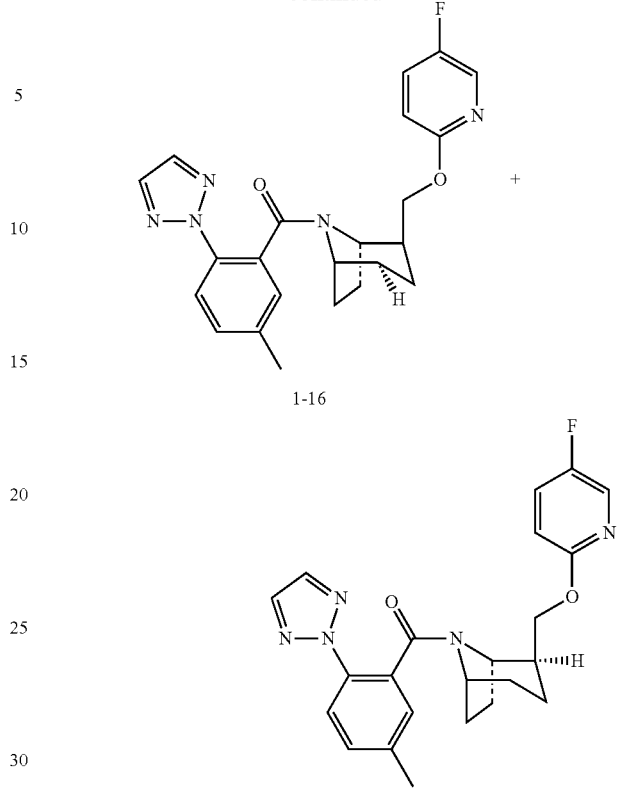

1-16

2-1

A wavy bond indicates that the bond may be upward or downward, and is not influenced by other groups (It has the same meaning hereinafter).

Step 1 (Synthesis of 1-3)

Compound 1-1 (10.0 g, 44.4 mmol) was dissolved in 55 mL tetrahydrofuran, LDA (24.4 mL, 0.0488 mol) was slowly added dropwise under −78° C., and the mixture was stirred for 1 h under −78° C. Keeping the temperature at −78° C., compound 1-2 was added into the reaction dropwise, and after the addition, the temperature was slowly raised to room temperature, and the reaction was stirred overnight under room temperature. The reaction mixture was poured into aqueous ammonium chloride solution (50 mL), and concentrated under reduced pressure to give a crude product. 50 mL of saturated aqueous sodium chloride solution was added, and extracted with ethyl acetate (100 mL×3). The combined organic phase was washed with water (100 mL×2), saturated NaCl solution (100 mL×2) successively, and dried over anhydrous $Na_2SO_4$, filtered, and purified by column chromatography (petroleum ether:ethyl acetate=50:1) to give the product 1-3 as a yellow liquid, yield: 80%. (Solid was precipitated after cooled and placed.)

LC/MS: 198.0 (M-Boc+H$^+$)

Step 2 (Synthesis of 1-4)

Compound 1-3 (1.5 g, 5.05 mmol) was dissolved in 15 mL methanol, and $NaBH_4$ (192 mg, 5.05 mmol) was added. The reaction mixture was stirred under room temperature for 12 hours. 20 mL of water was added into the reaction mixture to quench, and the mixture was concentrated and extracted with ethyl acetate (20 mL×3). The combined organic phase was washed with water (100 mL×2), saturated NaCl solution (100 mL×2) successively, and dried over anhydrous $Na_2SO_4$, filtered, and the filtrate was concentrated under vacuum to give the product 1-4, which was used in next step without purification.

Step 3 (Synthesis of 1-5)

The crude compound 1-4 (1.4 g) was dissolved in 40 mL dichloromethane. Triethylamine (1.01 g, 10 mmol) and methanesulfonyl chloride (1.12 g, 9.86 mmol) were added under 0° C. After stirred for 30 minutes, the mixture was warmed to room temperature and stirred under room temperature for 10 hours. The reaction mixture was poured into water and extracted with dichloromethane (100 mL×3). The combined organic phase was washed with water (100 mL×2), saturated NaCl solution (100 mL×2) successively, and dried over anhydrous $Na_2SO_4$, filtered, and the filtrate was concentrated under vacuum to give the product 1-5, which was used in next step without purification.

Step 4 (Synthesis of $_{1-6}$)

The crude compound 1-5 (about 600 mg) was dissolved in 10 mL DMF, and DBU (4 g, 16 mmol) was added. The mixture was heated to 100° C. and stirred for 16 hours. The reaction mixture was cooled to room temperature. After adding 50 mL of water, the mixture was extracted with ethyl acetate (20 mL×2). The combined organic phase was washed with water (20 mL×2) and saturated NaCl solution (20 mL×2) successively, and dried over anhydrous $Na_2SO_4$, filtered, and purified by column chromatography (petroleum ether:ethyl acetate=50:1) to give 280 mg of the product 1-6 (yellow liquid. Solid was precipitated after cooled and placed. The total yield of the three steps: 30%).
LC/MS: 182.0 (M-Boc+H$^+$), 226.0 (M−56+H$^+$), 304.0 (M+Na$^+$)
$^1$H NMR (400 MHz, CDCl$_3$) δ 6.75 (s, 1H), 4.34-4.32 (m, 1H), 4.10-4.02 (m, 2H), 2.96-2.90 (m, 1H), 2.08-2.02 (m, 2H), 1.97-1.91 (m, 2H), 1.63-1.55 (m, 2H), 1.45 (s, 9H), 1.42-1.28 (m, 3H).

Step 5 (Synthesis of 1-7)

Compound 1-6 (300 mg, 1.06 mmol) was dissolved in 20 mL methanol, and wet Pd(OH)$_2$ (50 mg, 5%) was added and stirred under hydrogen for 16 hours. The reaction mixture was filtered and the filtrate was concentrated under vacuum to give the product 1-7, which was used in next step without purification.

Step 6 (Synthesis of 1-8)

The compound 1-7 (300 mg, 1.06 mmol) was dissolved in 30 mL tetrahydrofuran. Under 0° C., LAH (80 mg, 2 mmol) was added in several batches with small amount for each batch. After addition, the ice bath was removed and mixture was warmed to room temperature, and the reaction was conducted under room temperature for 4 hours. Into the reaction mixture were successively added 0.08 mL water, 0.08 mL 15% aqueous sodium hydroxide and 0.24 mL water. A small amount of magnesium sulfate was added. The mixture was filtered after being stirred for 10 minutes, and the filtrate was dried under rotation to obtain the product 1-8, which was used in next step without purification.
LC/MS: 237.0 (M-Boc+H$^+$), 337.1 (M+H$^+$)

Step 7 (Synthesis of 1-10)

The compound 1-8 (280 mg, 1.16 mmol) was dissolved in 14 mL DMF. Under 0° C., NaH (139 mg, 3.48 mmol) was added in several batches with small amount for each batch. The mixture was stirred under the same temperature for 30 minutes, and the compound 1-9 was slowly added. After addition, the reaction was conducted under room temperature for 10 hours. The reaction mixture was poured into 30 mL water and 10 mL saturated NaCl solution was added. The mixture was extracted with ethyl acetate (10 mL×3). The combined organic phase was washed with water (10 mL×2), saturated NaCl solution (10 mL×2) successively, and dried over anhydrous $Na_2SO_4$, filtered, and concentrated to obtain a crude product. The crude product was purified by column chromatography (petroleum ether:ethyl acetate=50:1) to give product 1-10 (150 mg, and the total yield of the three steps: 42%).

Step 8 (Synthesis of 1-11)

Compound 1-10 (300 mg) was separated by preparative HPLC to obtain the racemic product 1-11 (120 mg, 80%), while the racemate product 1-12 (100 mg, 67%) was obtained at the same time.

Step 9 (Synthesis of 1-13)

Compound 1-11 (120 mg) was dissolved in 4 mL of ethyl acetate, and hydrogenchloride in ethyl acetate solution (4 mL, 4M) was added dropwise under ice bath cooling. The mixture was stirred for 2 hours, concentrated under reduced pressure to give product 1-13 (hydrochloride form), and the product was used in the next step without purification.

Step 10 (Synthesis of 1-15)

Compound 1-13 (120 mg, 0.32 mmol), compound 1-14 (77 mg, 0.38 mmol), HATU (182 mg, 0.48 mmol) and DIEA (124 mg, 0.96 mmol) were dissolved in 5 mL of DMF, and mixture was stirred under room temperature for 3 hours. The reaction mixture was poured into aqueous saline and extracted with ethyl acetate (10 mL×3). The organic phase was combined and washed with water (10 mL×2) and saturated NaCl solution (10 mL×2), and dried under rotation to give the product 1-15 (28 mg, white solid, yield: 16%).
$^1$H NMR (400 MHz, MeOD) δ 8.01 (s, 1H), 7.93-7.88 (m, 2H), 7.75-7.73 (m, 1H), 7.52-7.45 (m, 2H), 7.41-7.36 (m, 1H), 6.86 (s, br, 0.5H), 6.4$_{1-6}$.38 (m, 0.5H), 4.75-4.66 (m, 1H), 4.48-4.33 (m, 1H), 4.14-4.04 (m, 1H), 3.77-3.72 (m, 1H), 2.45-2.42 (m, 1H), 2.30-225 (m, 1H), 1.94 (s, 3H), 1.87-1.83 (m, 4H), 1.67-1.46 (m, 3H).

Step 11 (Synthesis of 1-16 and 2-1)

Racemic compound 1-15 (28 mg) was separated via SFC separation (separation method: Instrument Model: MG II preparative SFC; separation column: phenomenex Lux C2, 250×30 mm I.D.; mobile phase: A: CO$_2$, B: ethanol (0.1% aqueous ammonia); density: B 40%; flow rate: 50 mL/min; back flow pressure: 100 bar; column temperature: 38° C.; UV detection wavelength: 220 nm) to give optically pure compound 1-16 (10 mg, white solid, yield: 71%) and the optically pure compound 2-1 (10 mg, white solid, yield:

71%). The absolute configuration of compound 1-16 was confirmed by single crystal X-ray spectra.

Examples 3 and 4

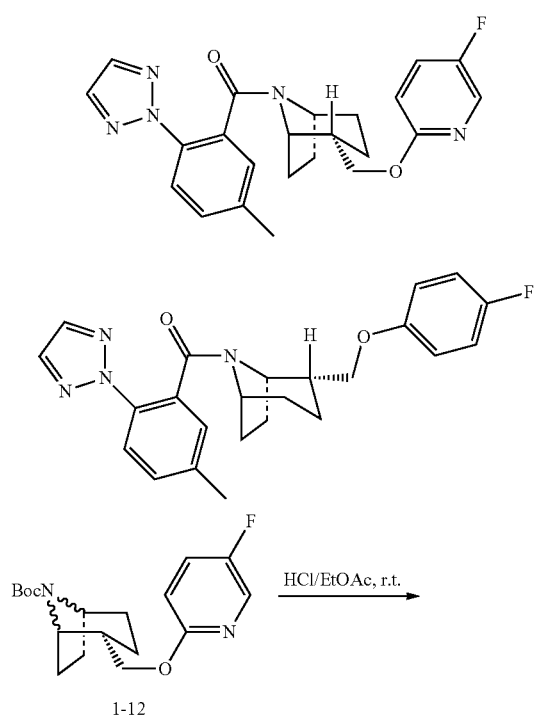

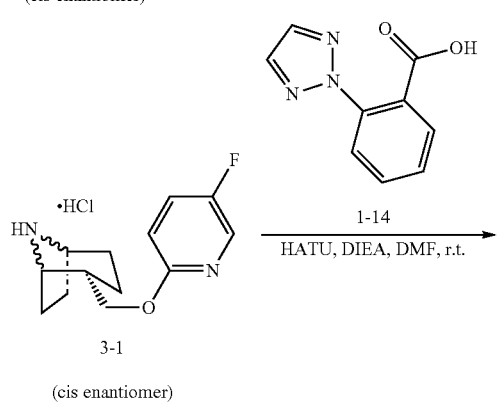

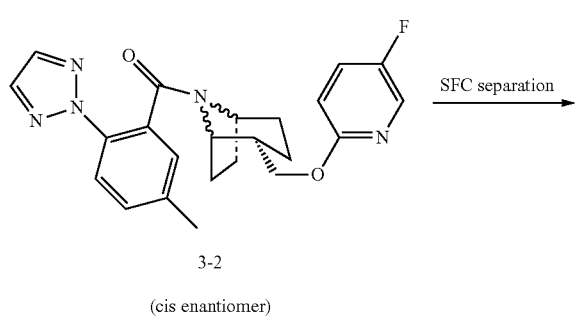

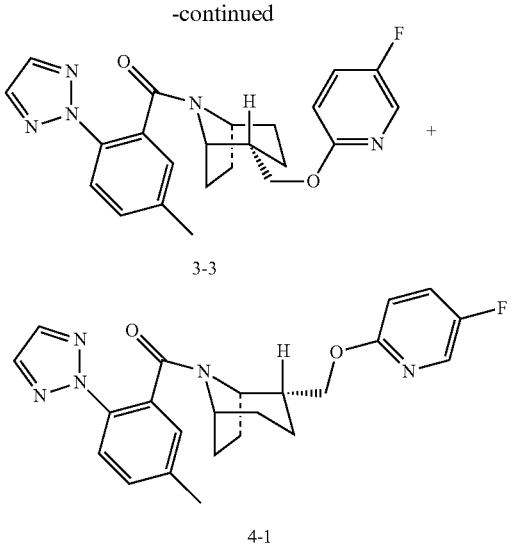

Step 1 (Synthesis of 3-1)

Compound 1-12 (100 mg) was dissolved in 4 mL of ethyl acetate, and hydrogen chloride in ethyl acetate (4 mL, 4M) was added dropwise under ice bath cooling. The mixture was stirred for 2 hours, concentrated under reduced pressure to give the product 3-1 (hydrochloride form) which was used in next step without purification.

Step 2 (Synthesis of 3-2)

Compound 3-1 (100 mg, 0.26 mmol), compound 1-14 (58 mg, 0.28 mmol), HATU (150 mg, 0.39 mmol) and DIEA (124 mg, 0.96 mmol) were dissolved in 5 mL of DMF, and the mixture was stirred under room temperature for 3 hours. The reaction mixture was poured into aqueous saline and extracted with ethyl acetate (10 mL×3). The organic phase was combined and washed with water (10 mL×2) and saturated NaCl solution (10 mL×2), dried, filtered and concentrated to give a crude product. The crude product was separated by preparative HPLC to obtain the compound 3-2 (30 mg, white solid, yield: 20%).

$^1$H NMR (400 MHz, MeOD) δ=8.14 (br. s., 1H), 8.00-7.61 (m, 4H), 7.49 (br. s., 0.5H), 7.33 (dd, J=8.0, 17.8 Hz, 1H), 7.12 (br. s., 1H), 6.56 (br. s., 0.5H), 5.00-4.83 (m, 1H), 4.48 (br. s., 3H), 3.88-3.62 (m, 1H), 2.45-2.34 (m, 3H), 2.05-1.56 (m, 5H), 1.42-1.35 (m, 3H)

Step 3 (Synthesis of 3-3 and 4-1)

Racemic compound 3-2 (30 mg) was separated via SFC separation (separation method: Instrument Model: MG II preparative SFC; separation column: ChiralPak IC, 250×30 mm I.D.; mobile phase: A: CO$_2$, B: ethanol (0.1% aqueous ammonia); density: B 50%; flow rate: 45 mL/min; back flow pressure: 100 bar; column temperature: 38° C.; detection wavelength: 220 nm) to give optically pure compound 3-3 (12 mg, white solid, yield: 80%) and optically pure compound 4-1 (12 mg, white solid, yield: 80%).

(3-3 and 4-1 were a pair of enantiomers, and the relative structures were hypothetical structures, and the absolute structure was yet unconfirmed).

Examples 5 and 6

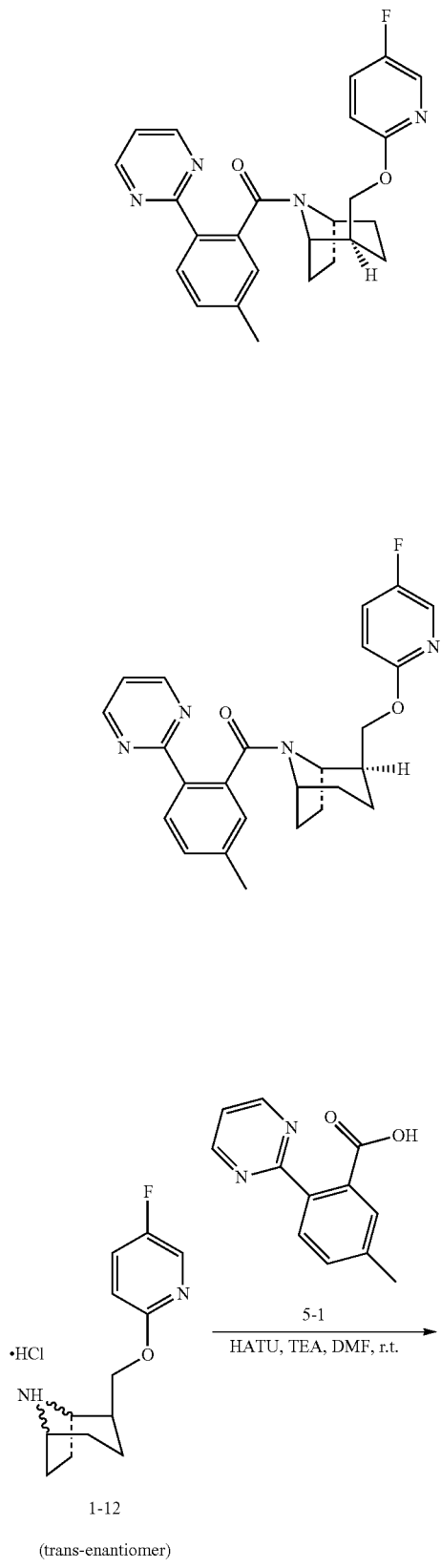

1-12
(trans-enantiomer)

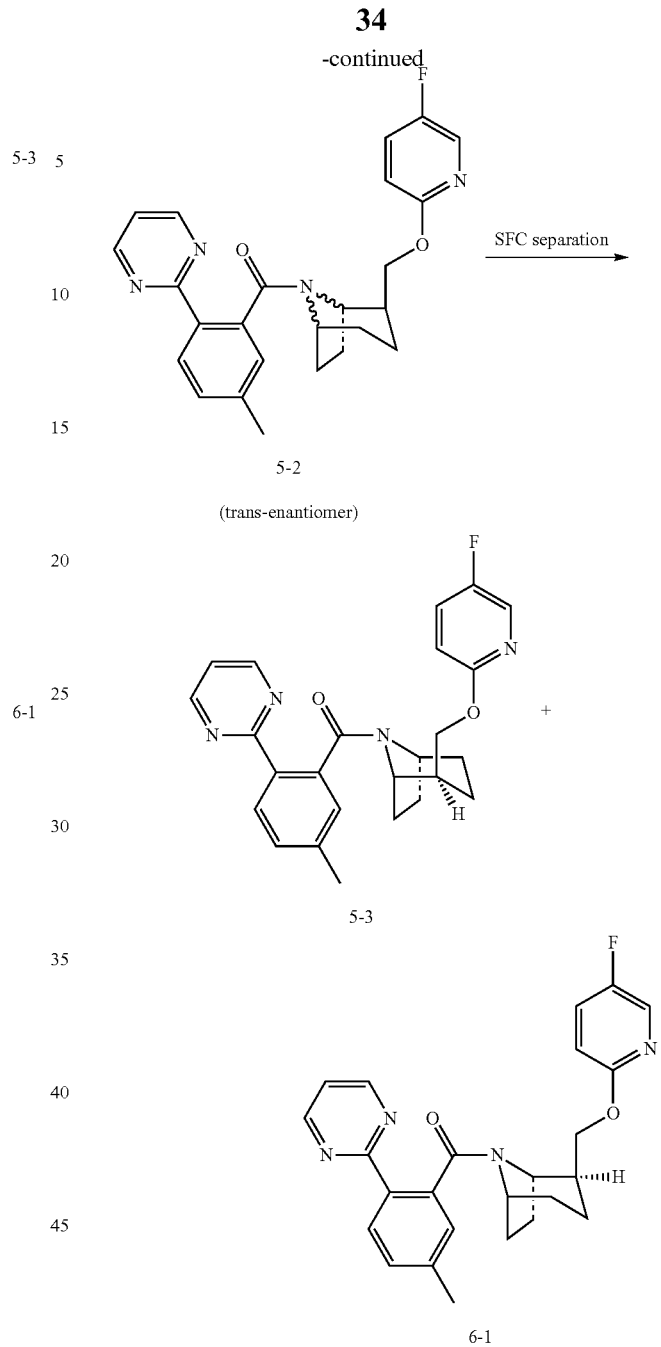

5-2
(trans-enantiomer)

Step 1 (Synthesis of 5-2)

Compound 1-12 (120 mg, 0.32 mmol), compound 5-1 (77 mg, 0.38 mmol), HATU (182 mg, 0.48 mmol) and DIEA (124 mg, 0.96 mmol) were dissolved in 5 mL of DMF, and the mixture was stirred under room temperature for 3 hours. The reaction mixture was poured into aqueous saline and extracted with ethyl acetate (10 mL×3). The organic phase was combined and washed with water (10 mL×2) and saturated NaCl solution (10 mL×2), dried with anhydrous Na$_2$SO$_4$, filtered, the crude product was purified with preparative HPLC to give product 5-2 (24 mg, white solid, yield: 14%).

$^1$H NMR (400 MHz, METHANOL-d$_4$)=8.83 (br. s., 2H), 8.17-8.01 (m, 2H), 7.49-7.33 (m, 3H), 6.86 (dd, J=3.5, 9.0

Hz, 1H), 6.41 (br. s., 1H), 4.63 (br. s., 1H), 4.43 (br. s., 1H), 4.11 (br. s, 1H), 3.79 (br. s., 1H), 2.52-2.48 (m, 2H), 2.35-2.11 (m, 1H), 2.01-1.95 (m, 3H), 1.90-1.67 (m, 3H), 1.63-1.43 (m, 1H), 1.29-1.20 (m, 2H)

Step 2 (Synthesis of 3-3 and 6-1)

Racemic compound 5-2 (24 mg) was separated via SFC separation (separation method: Instrument Model: MG II preparative SFC; separation column: ChiralPak IC, 250×30 mm I.D.; mobile phase: A: CO₂, B: ethanol (0.1% aqueous ammonia); density: B 45%; flow rate: 40 mL/min; back flow pressure: 100 bar; column temperature: 38° C.; detection wavelength: 220 nm) to give optically pure compound 5-3 (8 mg, white solid) and compound 6-1 (8 mg, white solid). The total yield of two compounds was 67%.

Examples 7 and 8

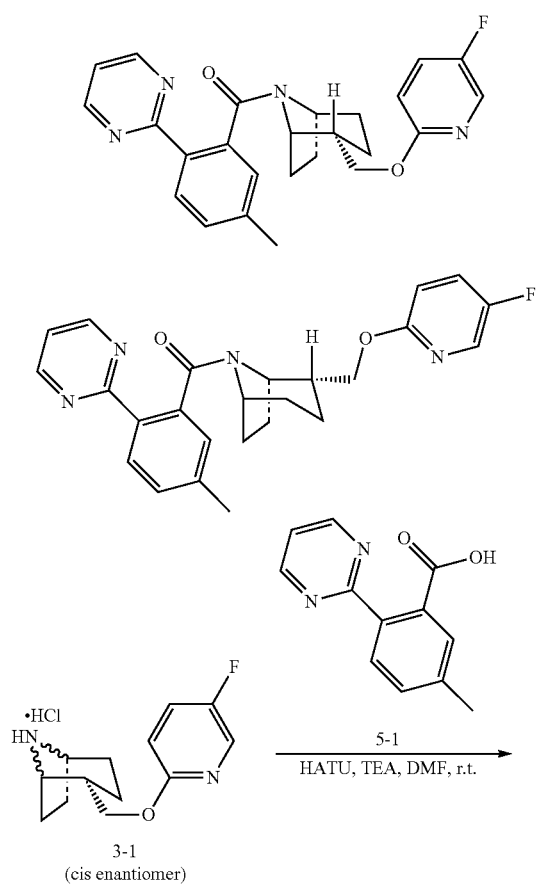

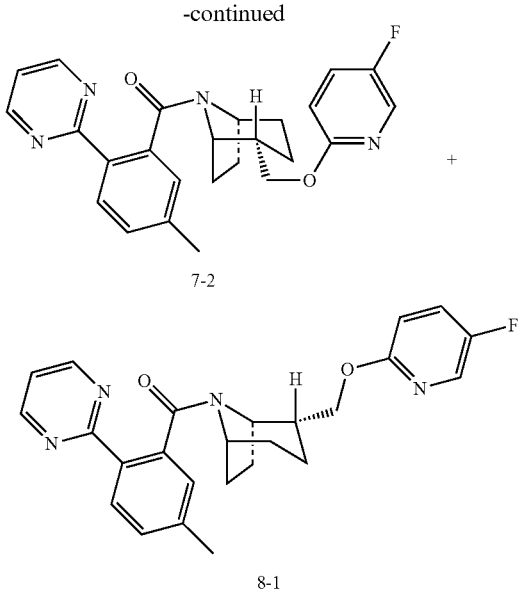

Step 1 (Synthesis of 7-1)

Compound 3-1 (100 mg, 0.26 mmol), compound 5-1 (58 mg, 0.28 mmol), HATU (150 mg, 0.39 mmol) and DIEA (124 mg, 0.96 mmol) were dissolved in 5 mL of DMF, and the mixture was stirred under room temperature for 3 hours. The reaction mixture was poured into aqueous saline and extracted with ethyl acetate (10 mL×3). The organic phase was combined and washed with water (10 mL×2) and saturated NaCl solution (10 mL×2), dried, filtered and concentrated to give a crude product. The crude product was separated by preparative HPLC to obtain compound 7-1 (30 mg, white solid, yield: 20%).

¹H NMR (400 MHz, MeOD) δ=8.78 (dd, J=4.9, 9.7 Hz, 2H), 8.17 (d, J=8.2 Hz, 0.5H), 8.11 (d, J=7.9 Hz, 0.5H), 8.01 (d, J=3.1 Hz, 0.5H), 7.75 (br. s., 0.5H), 7.57-7.50 (m, 0.5H), 7.43 (d, J=8.2 Hz, 0.5H), 7.38-7.31 (m, 2H), 7.26 (s, 0.4H), 7.13 (s, 0.6H), 6.86 (dd, J=3.5, 9.0 Hz, 0.5H), 6.36 (dd, J=3.5, 9.0 Hz, 0.5H), 4.77-4.72 (m, 0.5H), 4.21-4.11 (m, 1.5H), 3.78 (br. s., 1H), 2.52 (br. s., 1H), 2.46 (s, 1.5H), 2.35 (s, 1.5H), 2.09-1.95 (m, 2H), 1.91-1.37 (m, 7H)

Step 7 (Synthesis of 3-2 and 8-1)

Racemic compound 7-1 (30 mg) was separated via SFC separation (separation method: Instrument Model: MG II preparative SFC; separation column: ChiralPak AS, 250×30 mm I.D.; mobile phase: A: CO₂, B: ethanol (0.1% aqueous ammonia); density: B 15%; flow rate: 60 mL/min; back flow pressure: 100 bar; column temperature: 38° C.; detection wavelength: 220 nm) to give optically pure compound 7-2 (12 mg, white solid, yield: 80%) and optically pure compound 8-1 (12 mg, white solid, yield: 80%).

(7-2 and 8-1 were a pair of enantiomers, and the relative structures were hypothetical structures, and the absolute structure was yet unconfirmed).

Example 9

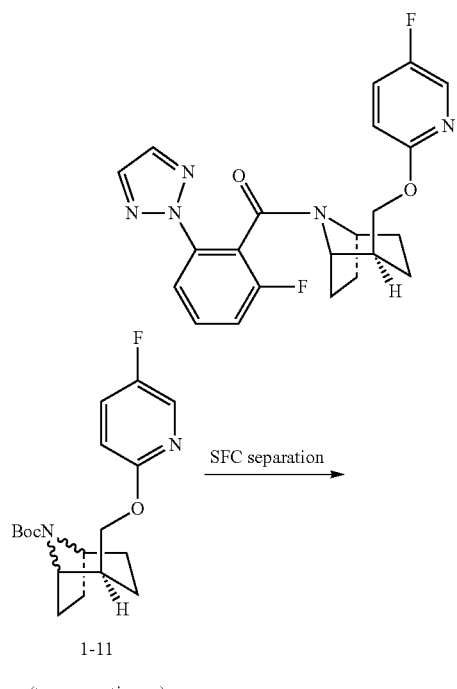

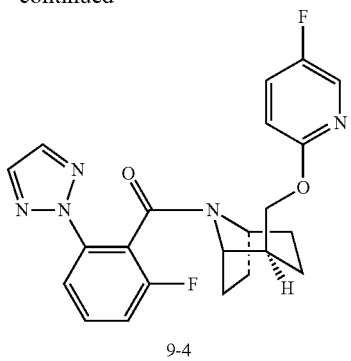

Step 1 (Synthesis of 9-1)

Racemic compound 1-11 (280 mg) was separated via SFC separation (separation method: Instrument Model: MG II preparative SFC (SFC-1); separation column: ChiralPak AS, 250×30 mm I.D.; mobile phase: A: $CO_2$, B: ethanol (0.1% aqueous ammonia); density: B 25%; flow rate: 60 mL/min; back flow pressure: 100 bar; column temperature: 38° C.; detection wavelength: 220 nm) to give optically pure product 9-1 (100 mg, white solid, yield: 71%).

Step 2 (Synthesis of 9-2)

Compound 9-1 (120 mg) was dissolved in 4 mL of ethyl acetate, and hydrogen chloride in ethyl acetate (4 mL, 4M) was added dropwise under ice bath cooling. The mixture was stirred for 2 hours, concentrated under reduced pressure to give product 9-2 (hydrochloride form), which was used in next step without purification.

Step 3 (Synthesis of 9-4)

Compound 9-2 (120 mg, 0.32 mmol), compound 9-3 (77 mg, 0.38 mmol), HATU (182 mg, 0.48 mmol) and DIEA (124 mg, 0.96 mmol) were dissolved in 5 mL of DMF, and the mixture was stirred under room temperature for 3 hours. The reaction mixture was poured into aqueous saline and extracted with ethyl acetate (10 mL×3). The organic phase was combined and washed with water (10 mL×2) and saturated NaCl solution (10 mL×2), dried with anhydrous $Na_2SO_4$, filtered, and concentrated to obtain a crude product. The crude product was purified with preparative HPLC to give product 9-4 (22 mg, white solid, yield: 21%).

$^1$H NMR (400 MHz, MeOD) δ=8.20-7.98 (m, 3H), 7.85-7.72 (m, 1H), 7.71-7.50 (m, 2H), 7.48-7.17 (m, 1H), 7.03-6.75 (m, 1H), 4.87-4.66 (m, 1H), 4.54-4.36 (m, 1H), 4.31-4.05 (m, 1H), 3.86-3.55 (m, 1H), 2.14 (br. s., 1H), 2.08-1.95 (m, 1H), 1.88 (td, J=7.2, 19.8 Hz, 2H), 1.77 (dd, J=11.3, 18.1 Hz, 2H), 1.68-1.54 (m, 1H), 1.53-1.32 (m, 2H)

Example 10

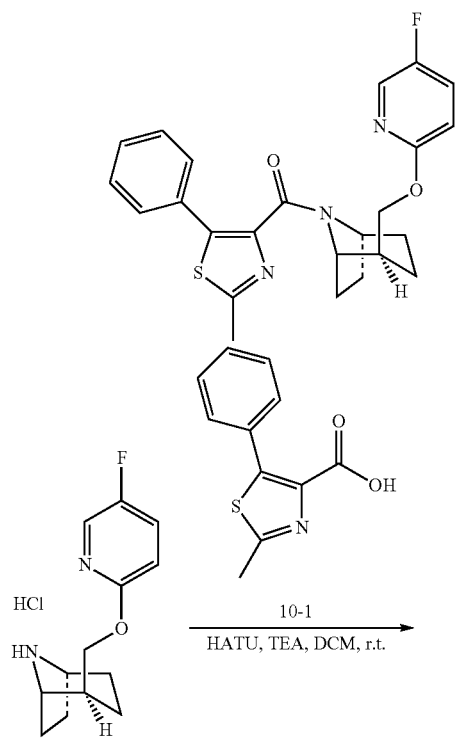

Step 1 (Synthesis of 10-2)

Compound 9-2 (120 mg, 0.32 mmol), compound 10-1 (77 mg, 0.38 mmol), HATU (182 mg, 0.48 mmol) and DIEA (124 mg, 0.96 mmol) were dissolved in 5 mL of DMF, and the mixture was stirred under room temperature for 3 hours. The reaction mixture was poured into aqueous saline and extracted with ethyl acetate (10 mL×3). The organic phase was combined and washed with water (10 mL×2) and saturated NaCl solution (10 mL×2), dried with anhydrous $Na_2SO_4$, filtered, and concentrated to obtain a crude product. The crude product was purified with preparative HPLC to give product 10-2 (41 mg, white solid, yield: 42%).

$^1$H NMR (400 MHz, $CHCl_3$-d)=8.11-7.90 (m, 1H), 7.81-7.56 (m, 2H), 7.49-7.38 (m, 2H), 7.35 (d, J=8.8 Hz, 1H), 6.77 (br. s., 1H), 6.42 (d, J=6.0 Hz, 1H), 4.97 (br. s., 0.3H), 4.82 (br. s., 0.7H), 4.40 (br. s., 0.5H), 4.14 (br. s., 1H), 4.06 (br. s., 0.6H), 4.00 (d, J=10.3 Hz, 0.5H), 3.74 (br. s., 0.4H), 2.76 (br. s., 1H), 2.12 (br. s., 0.5H), 2.06-1.86 (m, 2.5H), 1.85-1.67 (m, 2H), 1.62 (br. s., 1H), 1.65-1.56 (m, 2H), 1.45 (br. s., 1H), 1.12 (br. s., 1H), 0.67 (d, J=6.3 Hz, 1H)

Example 11

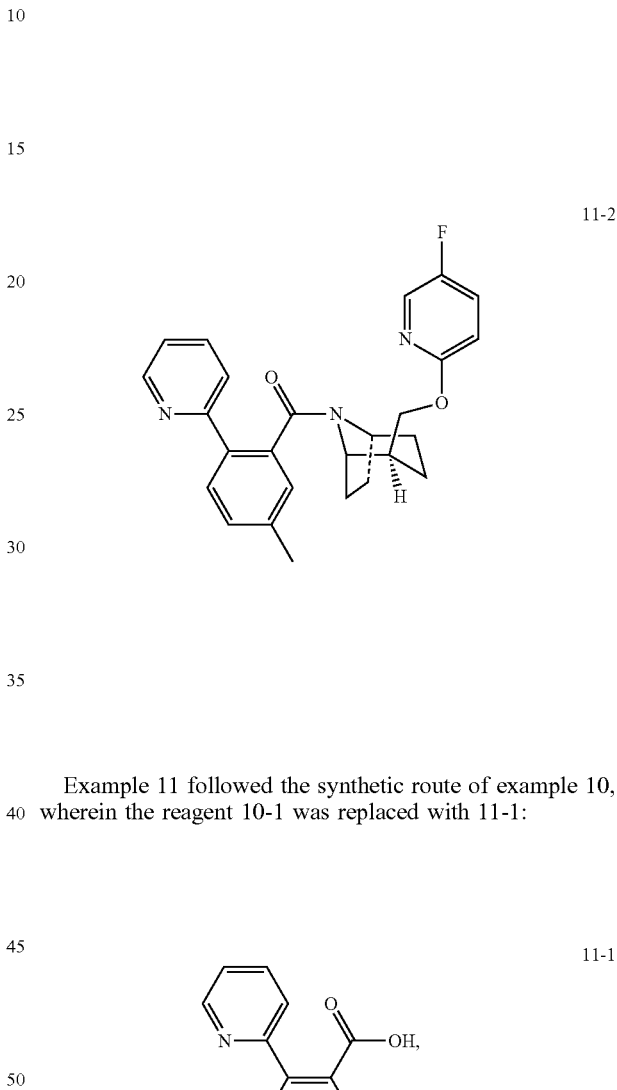

Example 11 followed the synthetic route of example 10, wherein the reagent 10-1 was replaced with 11-1:

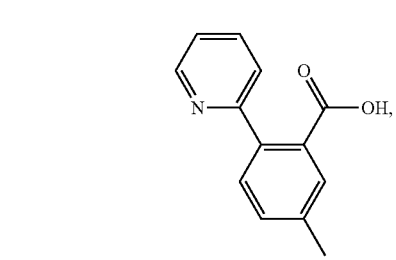

and the product 11-2 was obtained by preparative HPLC purification (24 mg, white solid, yield: 25%).

$^1$H NMR (400 MHz, $CHCl_3$-d)=8.55 (br. s., 1H), 8.42 (br. s., 0.5H), 8.03-7.85 (m, 1H), 7.80-7.63 (m, 2H), 7.57 (d, J=7.5 Hz, 1H), 7.41 (d, J=8.0 Hz, 1H), 7.34-7.28 (m, 1.5H), 7.23 (d, J=5.0 Hz, 1H), 6.84-6.63 (m, 1H), 4.50 (t, J=9.5 Hz, 1H), 4.32 (dd, J=5.8, 10.8 Hz, 1H), 3.89 (br. s., 2H), 2.40 (s, 3H), 2.20-1.93 (m, 4H), 1.84 (dt, J=7.3, 13.4 Hz, 1H), 1.72 (d, J=8.5 Hz, 2H), 1.52 (d, J=11.5 Hz, 1H), 1.48-1.35 (m, 1H)

Example 12

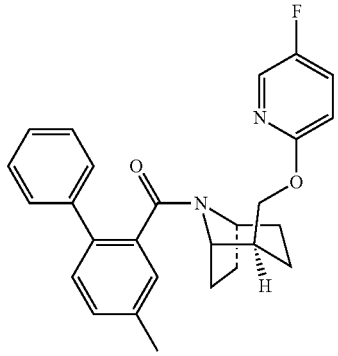

12-2

Example 12 followed the synthetic route of example 10, wherein the reagent 10-1 was replaced with 12-1:

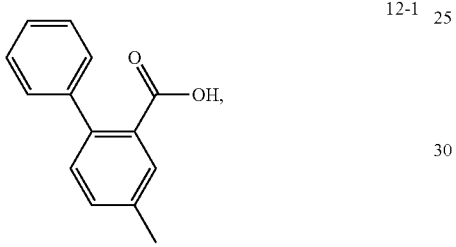

12-1 and the product 12-2 was obtained by preparative HPLC purification (8 mg, white solid, yield: 9%).

$^1$H NMR (400 MHz, CHCl$_3$-d)=7.96 (d, J=2.5 Hz, 1H), 7.57-7.43 (m, 2H), 7.42-7.30 (m, 3H), 7.30-7.23 (m, 2.5H), 7.20 (s, 1H), 7.09 (d, J=8.0 Hz, 1H), 6.26 (dd, J=3.5, 9.0 Hz, 0.5H), 4.94-4.71 (m, 1H), 4.09-3.97 (m, 1H), 3.96-3.79 (m, 1H), 3.61 (d, J=7.0 Hz, 1H), 2.40 (s, 1H), 1.99-1.89 (m, 2.5H), 1.86-1.59 (m, 2.5H), 1.57-1.24 (m, 4H), 1.23-1.09 (m, 1H), 0.99-0.87 (m, 1H)

Example 13

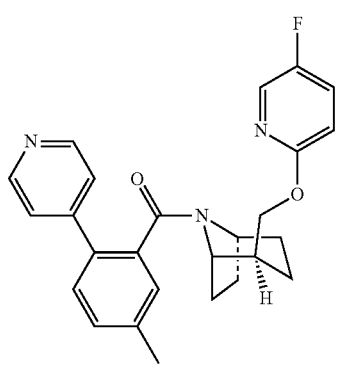

13-2

Example 13 followed the synthetic route of example 10, wherein the reagent 10-1 was replaced with 13-1:

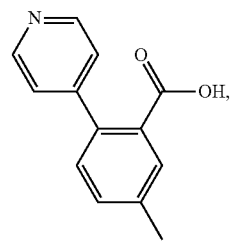

13-1 and the product 13-2 was obtained by preparative HPLC purification (37 mg, white solid, yield: 32%).

$^1$H NMR (400 MHz, CHCl$_3$-d)=8.64 (br. s., 2H), 8.13-7.85 (m, 1H), 7.85-7.53 (m, 2H), 7.40-7.33 (m, 1.5H), 7.40-7.29 (m, 0.5H), 7.24 (br. s., 1H), 7.17 (d, J=7.5 Hz, 1H), 6.76 (dd, J=3.5, 9.0 Hz, 0.5H), 6.27 (dd, J=3.5, 9.0 Hz, 0.5H), 4.95-4.74 (m, 1H), 4.12-3.87 (m, 2H), 3.64-3.44 (m, 1H), 2.44 (s, 1H), 2.11 (d, J=6.5 Hz, 1H), 2.07-1.88 (m, 2H), 1.88-1.72 (m, 2H), 1.72-1.63 (m, 1H), 1.62-1.42 (m, 3H), 1.41-1.29 (m, 1H), 1.29-0.98 (m, 1H)

Example 14

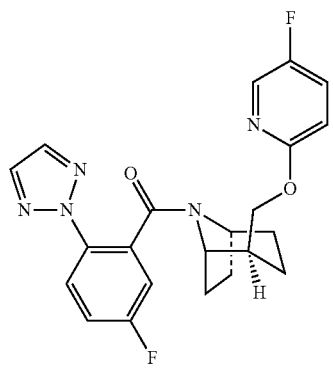

14-2

Example 14 followed the synthetic route of example 10, wherein the reagent 10-1 was replaced with 14-1:

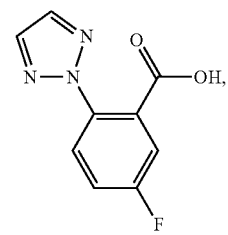

14-1 and the product 14-2 was obtained by preparative HPLC purification (19 mg, pale yellow solid, yield: 20%).

$^1$H NMR (400 MHz, CHCl$_3$-d)=8.04-7.90 (m, 1H), 7.89-7.63 (m, 2H), 7.34-7.26 (m, 1H), 7.23 (d, J=8.0 Hz, 1.5H), 7.15-6.93 (m, 1.5H), 6.80-6.76 (m, 0.5H), 6.32-6.30 (m, 0.5H), 4.99-4.90 (m, 1H), 4.49-4.35 (m, 1H), 4.19-4.03 (m, 1H) 3.87-3.68 (m, 1H), 2.01-1.86 (m, 6H), 1.70-1.38 (m, 2.5H), 1.36-1.05 (m, 0.5H)

Example 15

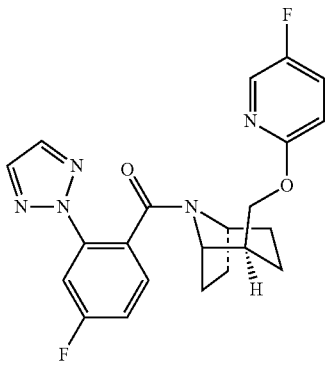
15-2

Example 15 followed the synthetic route of example 10, wherein the reagent 10-1 was replaced with 15-1:

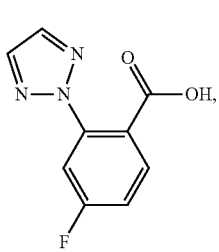
15-1 and the product 15-2 was obtained by preparative HPLC purification (17 mg, pale yellow solid, yield: 18%).

$^1$H NMR (400 MHz, CHCl$_3$-d)=8.01 (br. s., 1H), 7.94-7.70 (m, 2H), 7.64 (d, J=8.0 Hz, 1H), 7.42-7.23 (m, 2H), 6.77 (d, J=6.3 Hz, 1H), 6.59-6.24 (m, 1H), 4.99 (d, J=17.1 Hz, 1H), 4.52-4.32 (m, 1H), 4.25-4.04 (m, 1H), 3.92-3.44 (m, 1H), 2.53-2.10 (m, 1H), 2.09-1.76 (m, 4H), 1.68 (br. s., 1H), 1.61-1.38 (m, 2H), 1.37-0.62 (m, 1H)

Example 16

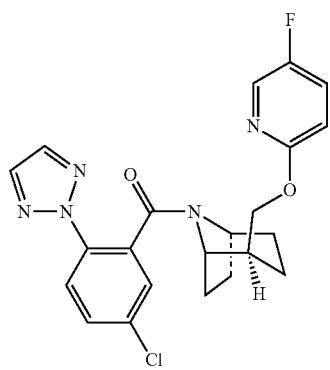
16-2

Example 16 followed the synthetic route of example 10, wherein the reagent 10-1 was replaced with 16-1:

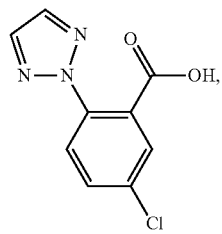
16-1 and the product 16-2 was obtained by preparative HPLC purification (6.5 mg, white solid, yield: 1.5%).

$^1$H NMR (400 MHz, CHCl$_3$-d)=8.30-7.72 (m, 2H), 7.71-7.52 (m, 1H), 7.52-7.37 (m, 1H), 7.35-7.14 (m, 3H), 6.78-6.38 (m, 1H), 4.94-4.66 (m, 1H), 4.53-4.21 (m, 1H), 4.08 (br. s., 1H), 3.83-3.58 (m, 1H), 2.53-2.40 (m, 0.5H), 1.90-1.82 (m, 1.5H), 1.81-1.45 (m, 5.5H), 1.27 (br. s., 0.5H), 1.0-0.91 (m, 1H)

Example 17

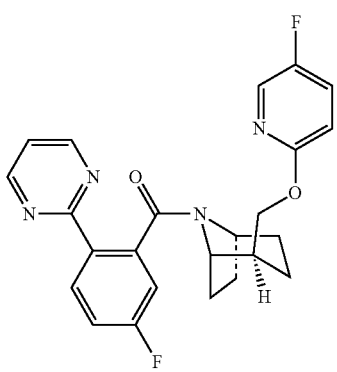
17-2

Example 17 followed the synthetic route of example 10, wherein the reagent 10-1 was replaced with 17-1:

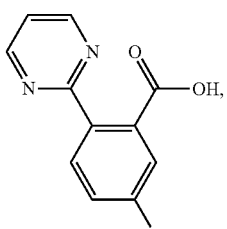
17-1 and the product 17-2 was obtained by preparative HPLC purification (4.3 mg, white solid, yield: 3.5%).

$^1$H NMR (400 MHz, CHCl$_3$-d)=8.76 (d, J=4.5 Hz, 1.5H), 8.39-8.12 (m, 1H), 7.96 (br. s., 1H), 7.34 (t, J=6.7 Hz, 0.5H), 7.30-7.26 (m, 1H), 7.19 (br. s., 1H), 7.16-6.84 (m, 2H), 6.74 (d, J=5.8 Hz, 0.5H), 6.29 (br. s., 0.5H), 5.08-4.83 (m, 1H), 4.48-4.15 (m, 1.5H), 4.14-4.04 (m, 0.5H), 3.89 (br. s., 0.5H), 3.78-3.63 (m, 0.5H), 2.27-2.06 (m, 2H), 2.03-1.93 (m, 1H), 1.92-1.81 (m, 1.5H), 1.79-1.59 (m, 2H), 1.57-1.41 (m, 1.5H), 1.25 (br. s., 1H)

Example 18

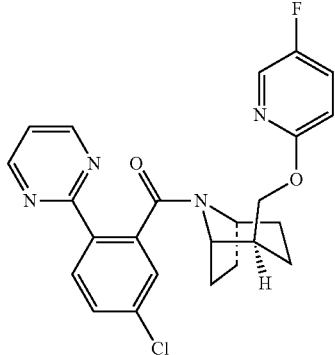

Example 18 followed the synthetic route of example 10, wherein the reagent 10-1 was replaced with 18-1:

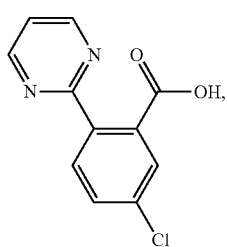

and the product 18-2 was obtained by preparative HPLC purification (4.3 mg, white solid, yield: 9.5%).

$^1$H NMR (400 MHz, CHCl$_3$-d)=8.94-8.74 (m, 1H), 8.65 (br. s., 1H), 8.39-8.26 (m, 1.5H), 7.70-7.42 (m, 0.5H), 7.36-7.25 (m, 1H), 7.14 (br. s., 1H), 6.92-6.8 (m, 0.5H), 6.79 (d, J=19.3 Hz, 1H), 5.98 (br. s., 0.5H), 5.15-4.97 (m, 1H), 4.70-4.38 (m, 1H), 4.26-4.07 (m, 1.6H), 3.80 (br. s., 0.4H), 2.52-2.32 (m, 1H), 2.29-2.18 (m, 2H), 2.11-1.92 (m, 1H), 1.91-1.81 (m, 2H), 1.62-1.35 (m, 3H)

Example 19

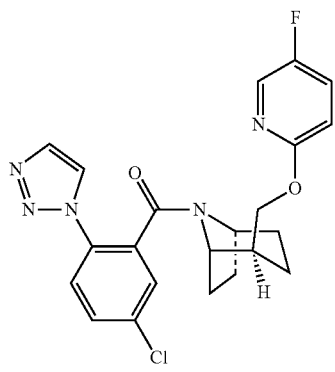

Example 19 followed the synthetic route of example 10, wherein the reagent 10-1 was replaced with 19-1:

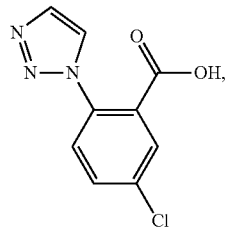

and the product 19-2 was obtained by preparative HPLC purification (29 mg, white solid, yield: 7%).

$^1$H NMR (400 MHz, CHCl$_3$-d)=8.28-7.90 (m, 1H), 7.85-7.69 (m, 1H), 7.64-7.47 (m, 1.5H), 7.46-7.38 (m, 1H), 7.36-7.28 (m, 1H), 7.25-7.21 (m, 1.5H), 6.76 (dd, J=3.3, 9.0 Hz, 0.5H), 6.36 (dd, J=3.4, 8.9 Hz, 0.5H), 4.85-4.69 (m, 1H), 4.57-4.20 (m, 1H), 4.06 (d, J=4.5 Hz, 1H), 3.77-3.57 (m, 1H), 2.24-1.99 (m, 1H), 1.97-1.78 (m, 2.5H), 1.76-1.52 (m, 4H), 1.46 (d, J=8.0 Hz, 1.5H)

Example 20

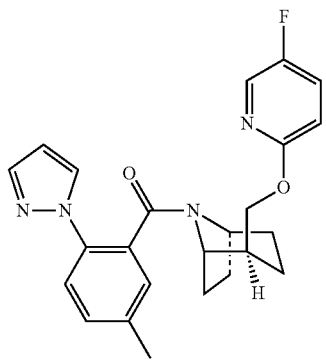

Example 20 followed the synthetic route of example 10, wherein the reagent 10-1 was replaced with 20-1:

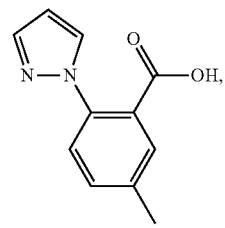

and the product 20-2 was obtained by preparative HPLC purification (51 mg, white solid, yield: 55%).

$^1$H NMR (400 MHz, CHCl$_3$-d)=8.08-7.93 (m, 1H), 7.87-7.60 (m, 2H), 7.56-7.42 (m, 1H), 7.34-7.24 (m, 2H), 7.22-7.16 (m, 1H), 6.79 (d, J=5.3 Hz, 0.4H), 6.42-6.27 (m, 1.6H), 4.97-4.73 (m, 1H), 4.50-3.91 (m, 2H), 3.77 (d, J=6.0 Hz, 0.6H), 3.58 (br. s., 0.4H), 2.43 (br. s., 1H), 2.26-2.03 (m, 1H), 2.00-1.88 (m, 3H), 1.85-1.65 (m, 3H), 1.59 (d, J=6.0 Hz, 2H), 1.51-1.37 (m, 2H)

Example 21

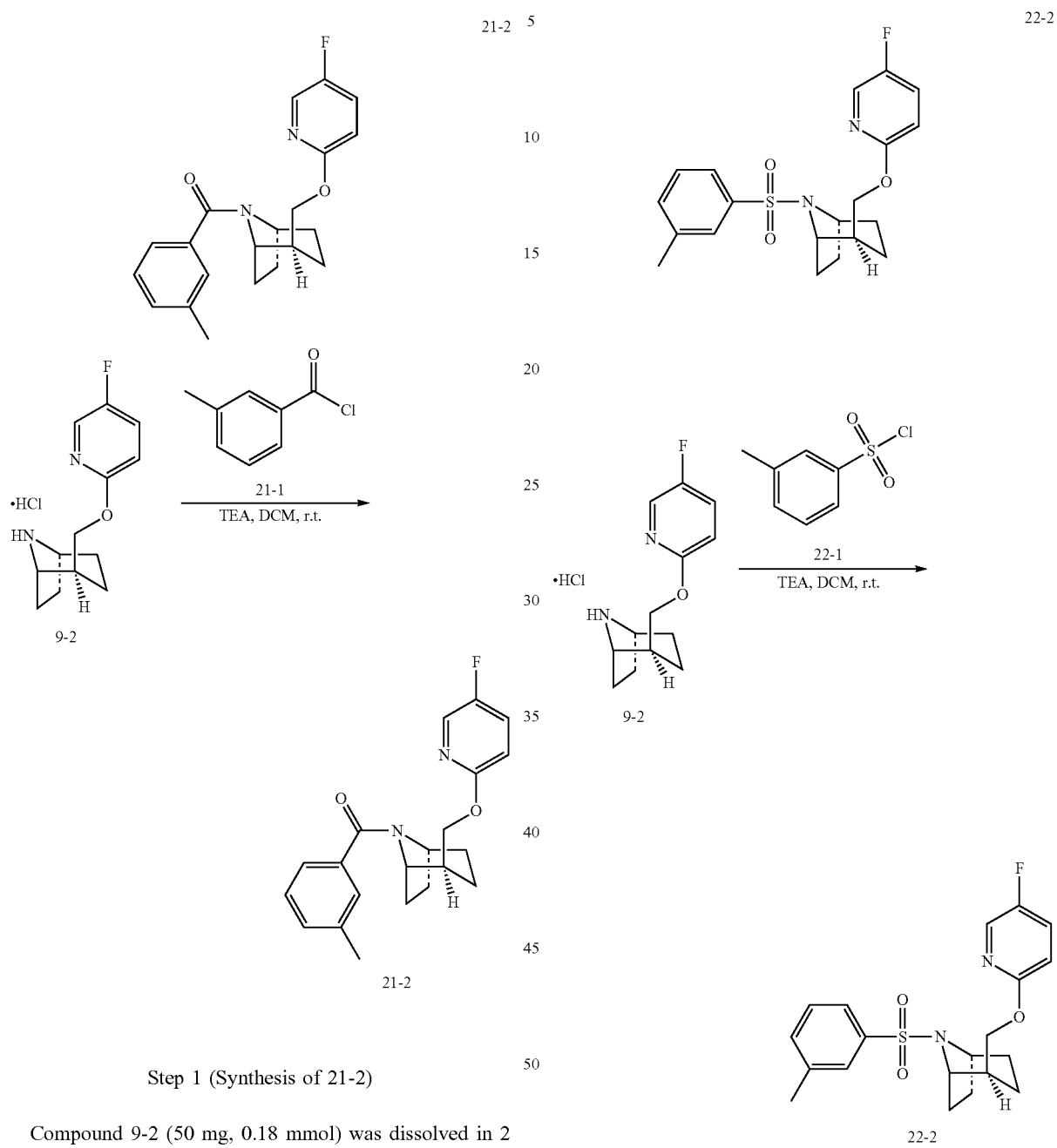

Step 1 (Synthesis of 21-2)

Compound 9-2 (50 mg, 0.18 mmol) was dissolved in 2 mL dichloromethane. Then triethylamine (56 mg, 0.55 mmol) and compound 21-1 (48 mg, 0.28 mmol) were added and the mixture was stirred under room temperature for 2 hours. The reaction mixture was spin dried to remove solvent so as to obtain a crude product. The crude product was purified by preparative HPLC to obtain product 21-2 (31 mg, yellow solid, yield: 9%).

$^1$H NMR (400 MHz, CHCl$_3$-d)=7.96 (br. s., 1H), 7.50-7.18 (m, 3H), 7.16-6.94 (m, 2H), 6.78-6.19 (m, 1H), 5.14-4.80 (m, 1H), 4.69-4.23 (m, 1.5H), 4.20-3.86 (m, 1.5H), 2.39 (br. s., 1H), 2.28-2.09 (m, 3H), 2.09-1.92 (m, 3H), 1.85 (br. s., 1H), 1.75 (br. s., 1H), 1.64 (s, 1H), 1.52 (br. s., 1H), 1.44-1.08 (m, 1H)

Example 22

Compound 9-2 (50 mg, 0.18 mmol) was dissolved in 2 mL dichloromethane. Triethylamine (56 mg, 0.55 mmol) and compound 22-1 (53 mg, 0.28 mmol) were added. After stirred under room temperature for 2 hours, the reaction mixture was spin dried to remove the solvent so as to obtain a crude product. The crude product was purified by preparative HPLC to obtain compound 22-2 (60 mg, white solid, yield: 87%).

$^1$H NMR (400 MHz, CHCl$_3$-d)=7.96 (d, J=2.8 Hz, 1H), 7.78-7.54 (m, 2H), 7.34-7.19 (m, 3H), 6.63 (dd, J=3.4, 8.9 Hz, 1H), 4.48-4.24 (m, 3H), 4.21-4.07 (m, 1H), 2.35 (s, 3H), 2.03 (d, J=6.0 Hz, 1H), 1.97-1.69 (m, 4H), 1.68-1.60 (m, 2.6H), 1.54-1.45 (m, 1.5H)

Example 23

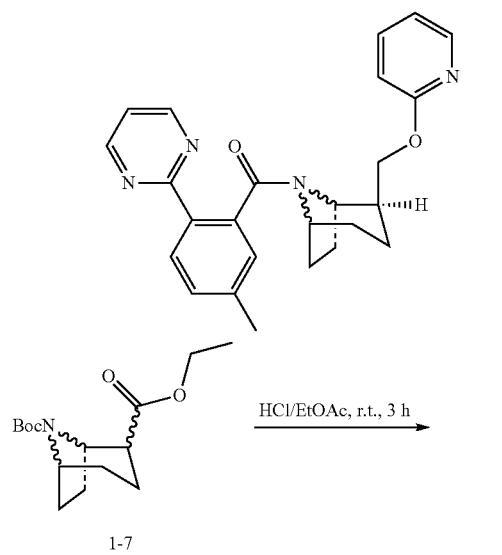

1-7
(cis/trans isomeric mixture)

HCl/EtOAc, r.t., 3 h →

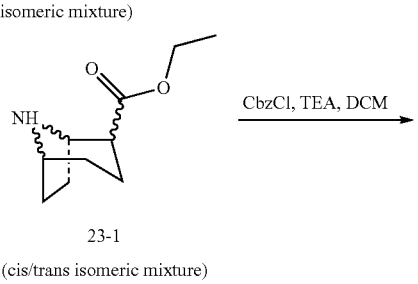

23-1
(cis/trans isomeric mixture)

CbzCl, TEA, DCM →

23-2
(cis/trans isomeric mixture)

HPLC →

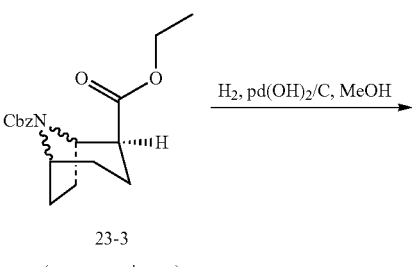

23-3
(trans-enantiomer)

H₂, pd(OH)₂/C, MeOH →

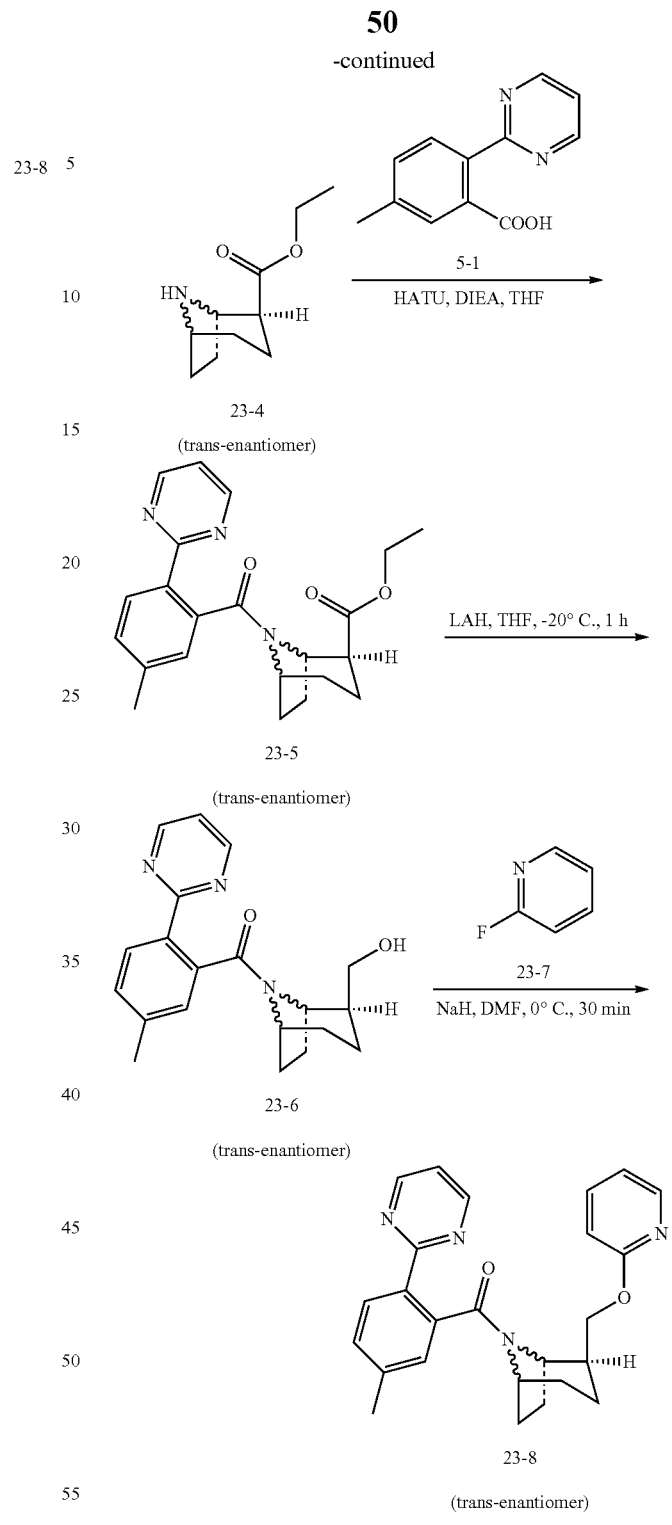

Step 23 (Synthesis of 1-1)

Compound 1-7 (48 g) was dissolved in 50 mL of ethyl acetate, and hydrogen chloride in ethyl acetate (150 mL, 4M) was added dropwise under ice bath cooling. The mixture was stirred for 2 hours, concentrated under reduced pressure to give product 23-1 (hydrochloride form), which was used in next step without purification.

Step 2 (Synthesis of 23-2)

Compound 23-1 (33 g, 150 mmol) was dissolved in 300 mL dichloromethane. TEA (62.7 mL, 450 mmol) and CbzCl (21.3 mL, 150 mmol) were added successively in a condition of ice-bath. After half an hour, the reaction mixture was warmed to room temperature and stirred overnight. The reaction mixture was cooled to room temperature and extracted with ethyl acetate (300 mL×3). The combined organic phase was washed with water (100 mL×2), saturated NaCl solution (100 mL×2) successively, and dried over anhydrous $Na_2SO_4$, filtered, and purified by column chromatography (petroleum ether:ethyl acetate=50:1) to give the product 23-2 (35 g, yellow liquid. Solid was precipitated after cooled and placed. Yield: 74%).

Step 3 (Synthesis of 23-3)

Compound 23-2 (35 g) was separated by preparative HPLC to obtain the product 23-3 (22 g, 62.8%).

Step 4 (Synthesis of 23-4)

Compound 23-3 (5 g, 15.75 mmol) was dissolved in 100 mL methanol, and wet $Pd(OH)_2$ (500 mg, 5%) was added. The mixture was stirred under hydrogen for 16 hours. The reaction mixture was filtered and the filtrate was concentrated to give the product 23-4 (2.7 g, 94%) (colorless oil), which was used in next step without purification.

Step 5 (Synthesis of 23-5)

Compound 23-4 (8 g, 43.7 mmol), compound 5-1 (11.2 g, 52.4 mmol), HATU (24.9 g, 65.6 mmol) and DIEA (16.9 g, 131.1 mmol) were dissolved in 200 mL of THF, and the mixture was stirred under room temperature for 16 hours. The reaction mixture was poured into aqueous saline and extracted with ethyl acetate (100 mL×3). The organic phase was combined and washed with water (50 mL×2) and saturated NaCl solution (50 mL×2), dried with anhydrous $Na_2SO_4$, filtered, and the filtrate was concentrated under reduced pressure to obtain a crude product. The crude product was purified with column (petroleum ether:ethyl acetate=1:2) to give product 23-5 (13 g, white solid, yield: 78%).

Step 6 (Synthesis of 23-6)

Compound 23-5 (950 mg, 2.5 mmol) was solved in 25 mL THF, and LAH (100 mg, 2.5 mmol) was added in iced ethanol bath. The reaction mixture was stirred under the present temperature for 1 hour. 20 mL of anhydrous THF was added for dilution. 0.1 mL of water, 0.1 mL of 15% sodium hydroxide solution and 0.3 mL of water were added dropwise successively to quench the reaction. Then the mixture was dried over anhydrous $Na_2SO_4$, filtered, and the filtrate was concentrated under reduced pressure to give product 23-6 (800 mg, yellow solid, yield: 96%), which was used directly in next step without purification.

Step 7 (Synthesis of 23-8)

Compound 23-6 (80 mg, 0.237 mmol) was solved in 5 mL DMF, and NaH (38 mg, 60%, 0.984 mmol) was added in a condition of iced bath. Compound 23-7 (46 mg, 0.474 mmol) was added into the reaction mixture after stirred under the present temperature for 0.5 hour. The reaction mixture was stirred under room temperature for 16 hour, poured into saline solution and extracted with dichloromethane (20 mL×3). The combined organic phase was washed with water (10 mL×2), saturated NaCl solution (10 mL×2) successively, and dried over anhydrous $Na_2SO_4$, filtered, and the filtrate was concentrated under reduced pressure, and purified with preparation TLC plate to give the product 23-8 (23.24 mg, white solid, yield: 23.7%).

$^1$H NMR (400 MHz, $CHCl_3$-d)=8.75 (br. s., 2H), 8.22-8.06 (m, 2H), 7.58-7.46 (m, 1H), 7.28 (d, J=8.0 Hz, 1H), 7.23-7.05 (m, 2H), 6.88-6.76 (m, 1H), 6.34 (br. s., 1H), 5.01 (d, J=6.5 Hz, 1H), 4.65-4.37 (m, 1H), 4.16 (d, J=6.3 Hz, 1H), 3.94-3.75 (m, 1H), 2.41 (s, 1H), 2.21 (d, J=7.0 Hz, 1H), 1.96-1.77 (m, 5H), 1.54-1.45 (m, 2H), 1.33-0.77 (m, 3H)

Example 24

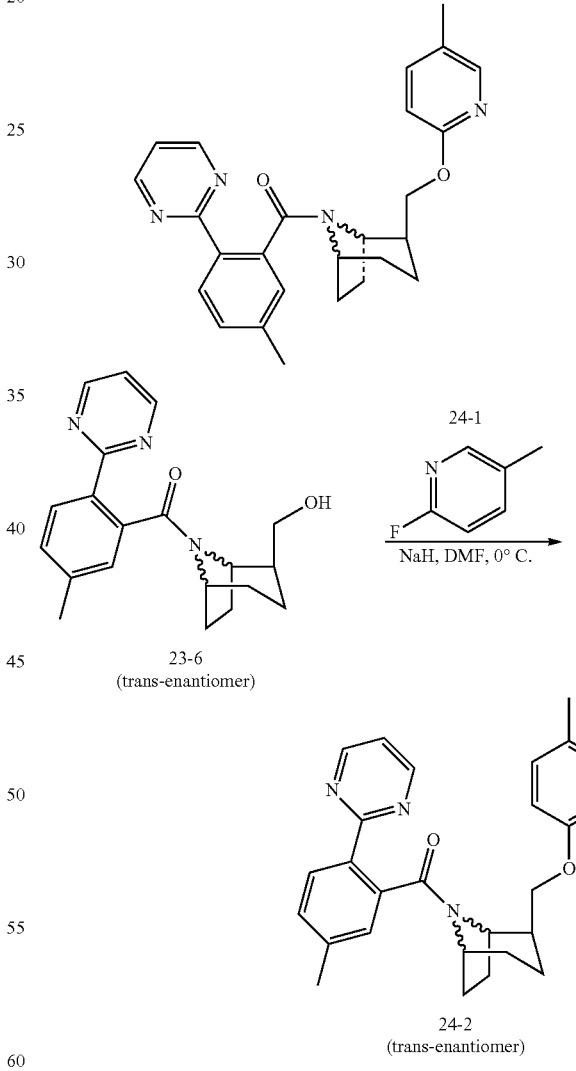

Step 1 (Synthesis of 24-2)

Compound 23-6 (80 mg, 0.237 mmol) was solved in 5 mL DMF, and NaH (38 mg, 60%, 0.984 mmol) was added in a condition of iced bath. Compound 24-1 (53 mg, 0.474 mmol) was added into the reaction mixture after it was stirred under the present temperature for 0.5 hour. The reaction mixture was stirred under room temperature for 16 hour, poured into saline solution and extracted with ethyl acetate (20 mL×3). The combined organic phase was washed with water (10 mL×2), saturated NaCl solution (10 mL×2) successively, and dried over anhydrous $Na_2SO_4$, filtered, and the filtrate was concentrated under reduced pressure to provide a crude product, which was further purified with preparation TLC plate to give the product 24-2 (17.6 mg, white solid, yield: 19%).

$^1$H NMR (400 MHz, $CHCl_3$-d)=8.75 (br. s., 2H), 8.20-8.07 (m, 1H), 7.98-7.88 (m, 1H), 7.41-7.28 (m, 1H), 7.23-7.08 (m, 3H), 6.71-6.25 (m, 1H), 5.01 (d, J=6.3 Hz, 1H), 4.64-4.30 (m, 1H), 4.12 (d, J=6.8 Hz, 1H), 3.92-3.75 (m, 1H), 2.41 (s, 1.5H), 2.29-2.16 (m, 4H), 2.01-1.75 (m, 6H), 1.56-1.44 (m, 1.5H), 1.30-1.21 (m, 1.5H), 0.98 (d, J=6.8 Hz, 0.5H)

Example 25

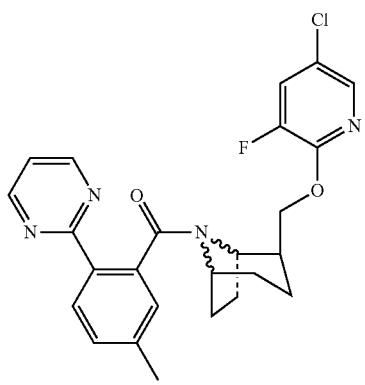

25-2

Step 1 (Synthesis of 25-2)

Example 25 followed the synthetic route of example 24, wherein the reagent 24-1 was replaced with 25-1:

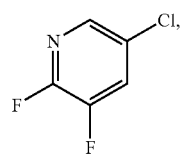

25-1 and the product 25-2 was obtained by TLC plate purification (33.72 mg, white solid, yield: 22%).

$^1$H NMR (400 MHz, $CHCl_3$-d)=8.74 (br. s., 2H), 8.16 (dd, J=7.7, 18.2 Hz, 1H), 7.89 (br. s., 1H), 7.37-7.25 (m, 2H), 7.24-7.12 (m, 2H), 5.01 (br. s., 1H), 4.84-4.36 (m, 1H), 4.21 (br. s., 1H), 3.80 (d, J=19.8 Hz, 1H), 2.42 (br. s., 2H), 2.09 (br. s., 2H), 1.86-1.8 (m, 3H), 1.68-1.60 (m, 1H), 1.60-1.43 (m, 2H), 1.35-1.13 (m, 2H),

Example 26

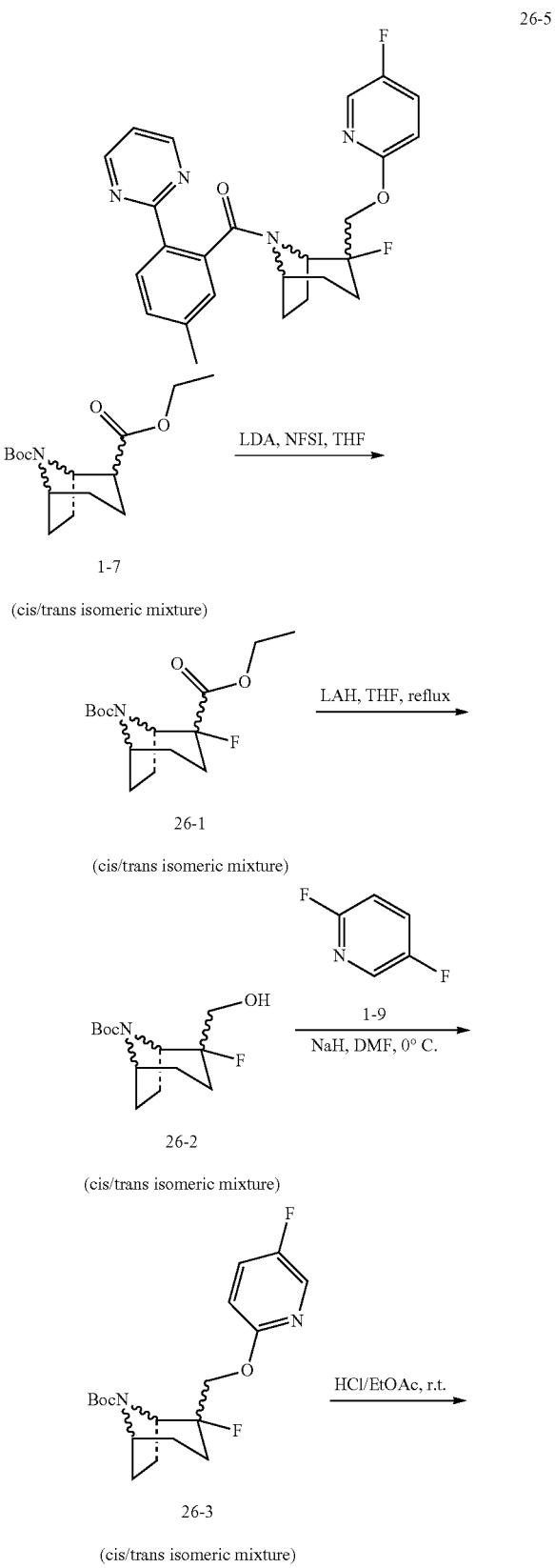

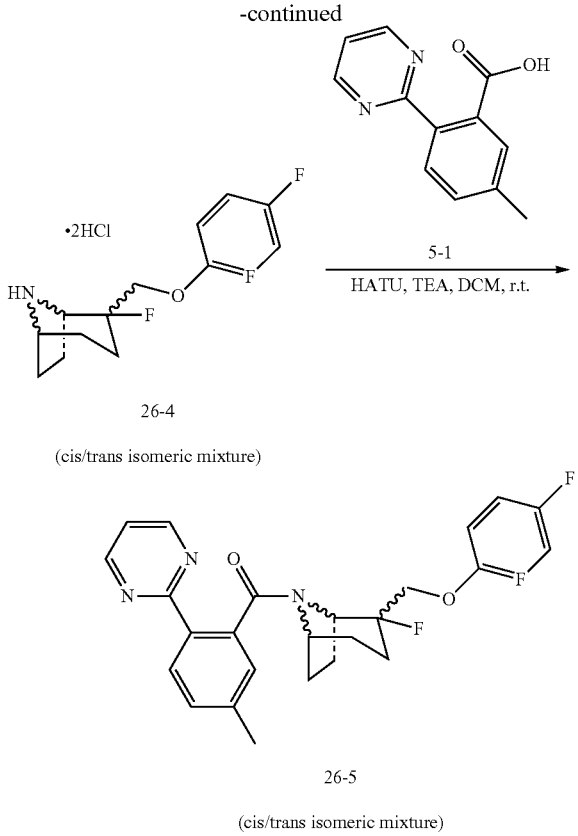

26-4

(cis/trans isomeric mixture)

26-5

(cis/trans isomeric mixture)

Step 26 (Synthesis of 26-1)

Compound 1-7 (4.0 g, 14.13 mmol) was dissolved in 30 mL tetrahydrofuran, and LDA (14.4 mL, 28.26 mmol) was slowly added dropwise under 0° C. The mixture was stirred at 0° C. for 1 h.

While the temperature was kept at 0° C., compound NFSI (5.3 g, 16.96 mmol) was added into the reaction. After the addition was completed, the temperature was slowly raised to room temperature, and the reaction mixture was stirred overnight at room temperature. The reaction mixture was poured into aqueous ammonium chloride solution (30 mL), and concentrated under reduced pressure. The crude product was added into 20 mL of saturated aqueous NaCl solution, and extracted with ethyl acetate (40 mL×3). The combined organic phase was washed with water (40 mL×2), saturated NaCl solution (40 mL×2) successively, and dried over anhydrous $Na_2SO_4$, filtered, and purified by column chromatography (petroleum ether:ethyl acetate=60:1-20:1) to give the product 26-1 (1.5 g, yellow oily liquid, yield: 40%).

LC/MS: 245.9 (M−56+H$^+$), 323.9 (M+Na$^+$)

Step 2 (Synthesis of 26-2)

The compound 26-1 (1.8 g, 6.0 mmol) was dissolved in 30 mL tetrahydrofuran. Under 0° C., LAH (500 mg, 13.15 mmol) was added in several batches with small amount for each batch. After addition was completed, the mixture was warmed to room temperature, and the reaction was conducted under room temperature overnight. 0.5 mL water, 0.5 mL 15% aqueous sodium hydroxide and 1.5 mL water were successively added into the reaction mixture. A small amount of magnesium sulfate was added. The mixture was filtered after being stirred for 10 minutes, and the filtrate was dried under rotation to obtain product 26-2, which was used in next step without purification.

Step 3 (Synthesis of 26-3)

The compound 26-2 (1.5 g, 5.88 mmol) was dissolved in 20 mL DMF. Under 0° C., NaH (800 mg, 20.0 mmol) was added in several batches with small amount for each batch. The mixture was stirred under the same temperature for 30 minutes, and the compound 1-9 (676 mg, 5.88 mmol) was added. After the addition, the reaction was conducted under room temperature for 10 hours. The reaction mixture was poured into 30 mL water. 10 mL saturated NaCl solution was added. The mixture was extracted with ethyl acetate (30 mL×3). The combined organic phase was washed with water (30 mL×2), saturated NaCl solution (30 mL×2) successively, and dried over anhydrous $Na_2SO_4$, filtered, and purified by column chromatography (petroleum ether:ethyl acetate=50:1) to give product 26-3 (500 mg. Yield of three steps: 25%).

LC/MS: 254.9 (M−56+H$^+$), 254.9 (M-Boc+H$^+$), 354.9 (M+H$^+$)

Step 4 (Synthesis of 26-4)

Compound 26-3 (150 mg) was dissolved in 4 mL of ethyl acetate, and hydrogen chloride in ethyl acetate (4 mL, 4M) was added dropwise under ice bath cooling. The mixture was stirred for 2 hours, concentrated under reduced pressure to give product 26-4 (hydrochloride form), which was used in next step without purification.

Step 5 (Synthesis of 26-5)

Compound 26-4 (120 mg, 0.37 mmol), compound 5-1 (94 mg, 0.38 mmol), HATU (209 mg, 0.55 mmol) and DIEA (143 mg, 0.96 mmol) were dissolved in 5 mL of DMF, and the mixture was stirred under room temperature for 3 hours. The reaction mixture was poured into aqueous saline and extracted with ethyl acetate (10 mL×3). The organic phase was combined and washed with water (10 mL×2) and saturated NaCl solution (10 mL×2), dried with anhydrous $Na_2SO_4$, filtered, and concentrated to obtain a crude product, which was purified with preparative HPLC to give product 26-5 (14 mg, yield: 7.8%).

$^1$H NMR (400 MHz, METHANOL-d4)=8.91-8.78 (m, 2H), 8.21-8.00 (m, 2H), 7.59-7.40 (m, 2H), 7.38-7.17 (m, 2H), 6.92 (dd, J=3.8, 9.3 Hz, 1H), 5.17-5.01 (m, 1H), 4.81-4.58 (m, 2H), 4.34 (br. s., 1H), 2.64-2.36 (m, 3H), 2.29-2.09 (m, 2H), 2.01-1.67 (m, 6H)

Example 27

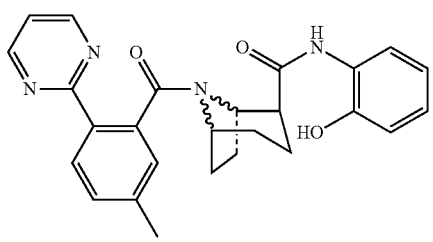

27-3

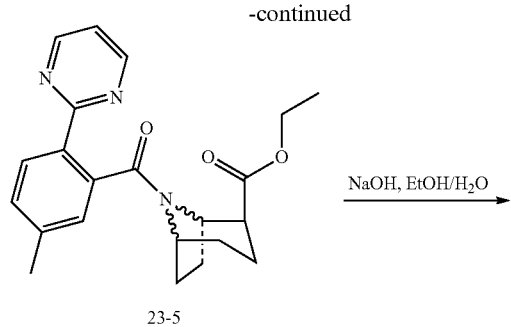

23-5

(trans-enantiomer)

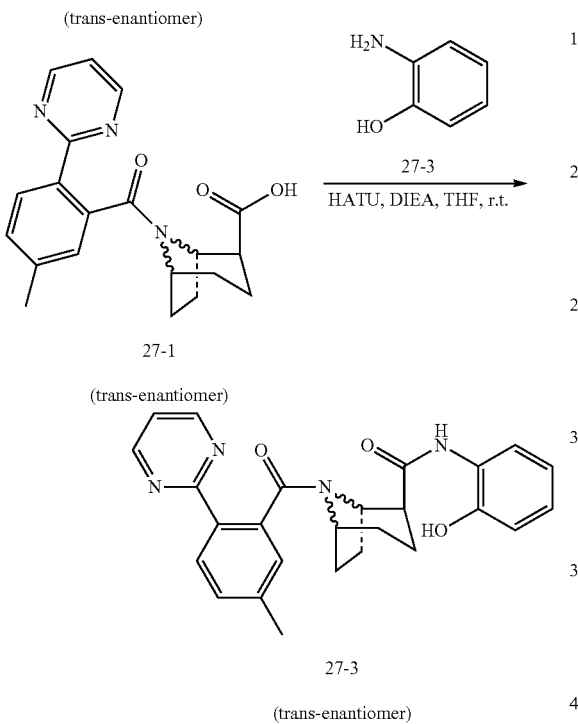

27-1

(trans-enantiomer)

27-3

(trans-enantiomer)

Step 1 (Synthesis of 27-1)

Compound 23-5 (190 mg) was dissolved in 10 mL THF, and 10 mL of 0.48% LiOH aqueous solution was added. The mixture was heated at reflux for 3 hours. The diluted hydrochloric acid was added dropwise until weak acidity. The mixture was extracted with ethyl acetate, and the organic phase was concentrated under reduced pressure to give product 27-1 (160 mg, 94%), which was used in next step directly without purification.

Step 2 (Synthesis of 27-3)

Compound 27-1 (105.4 mg, 0.3 mmol), compound 23-2 (65.5 mg, 0.6 mmol), HATU (171 mg, 0.45 mmol) and DIEA (0.157 mL, 0.9 mmol) were dissolved in 5 mL of THF, and the mixture was stirred under room temperature for 16 hours. The reaction mixture was poured into aqueous saline and extracted with ethyl acetate (10 mL×3). The organic phase was combined and washed with water (5 mL×2) and saturated NaCl solution (5 mL×2), dried with anhydrous Na$_2$SO$_4$, filtered, and the filtrate was concentrated under reduced pressure and purified with preparation TLC plate to give 100 mg of product 27-3 (100 mg, faint yellow solid).

$^1$H NMR (400 MHz, CHCl$_3$-d)=10.63 (br. s., 0.5H), 9.23 (br. s., 1H), 8.76 (br. s., 0.5H), 8.38 (br. s., 1H), 8.20 (br. s., 1H), 7.35 (d, J=8.0 Hz, 1.5H), 7.14-6.92 (m, 5H), 6.76-6.54 (m, 1.5H), 5.36-5.22 (m, 1H), 3.99 (br. s., 0.5H), 3.83 (br. s., 0.5H), 2.80 (s, 5H), 2.46-2.42 (m, 3H), 2.23 (d, J=7.5 Hz, 1H), 2.11-1.96 (m, 3H)

Example 28

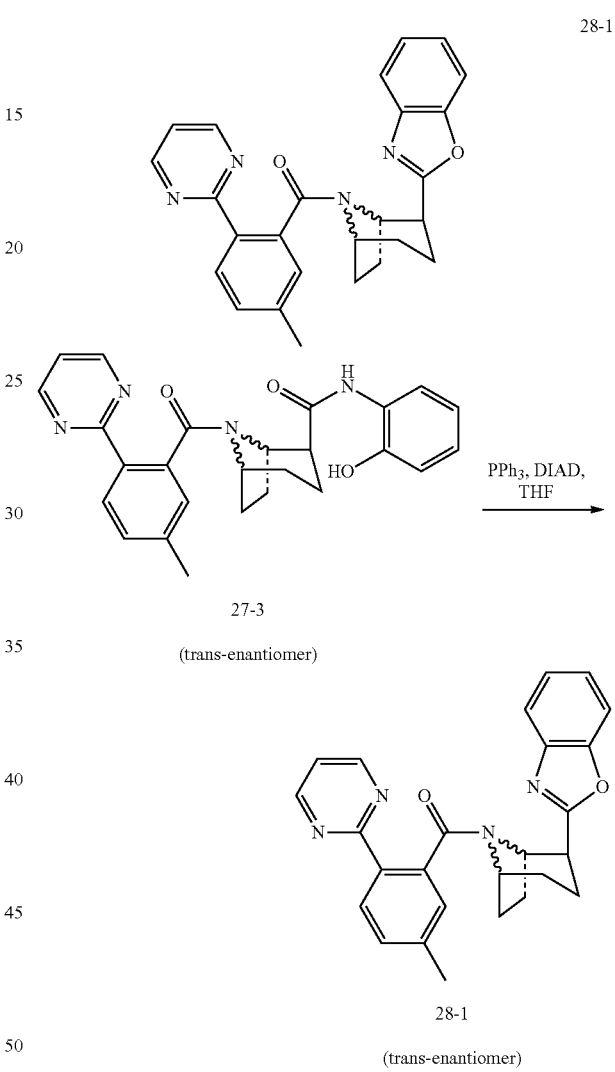

28-1

(trans-enantiomer)

Step 28 (Synthesis of 28-1)

Compound 27-3 (88 mg, 0.2 mmol) and triphenylphosphine (52.4 mg, 0.2 mmol) were dissolved in 25 mL of THF. Under nitrogen protection, 2 mL DIAD (40.4 mg, 0.2 mmol) in THF was added by syringe. The reaction mixture was heated at reflux for 3 hour, poured into saline solution and extracted with ethyl acetate (10 mL×3). The combined organic phase was washed with water (10 mL×2), saturated NaCl solution (10 mL×2) successively, and dried over anhydrous Na$_2$SO$_4$, filtered, and the filtrate was concentrated to obtain a crude product which was purified with preparation TLC plate to give product 28-1 (11.7 mg, white solid, yield: 13.37%).

¹H NMR (400 MHz, CHCl₃-d)=10.51 (br. s., 0.4H), 10.03 (br. s., 0.1H), 9.15 (s, 1H), 8.74 (br. s., 1H), 8.39 (br. s., 1H), 8.26-8.10 (m, 1H), 7.41-7.30 (m, 1.5H), 7.05 (br. s., 1.5H), 6.92 (d, J=8.5 Hz, 1.5H), 6.74 (br. s., 1H), 5.24 (br. s., 1H), 4.99-4.81 (m, 2H), 4.01 (br. s., 0.6H), 3.78 (br. s., 0.4H), 2.78 (br. s., 1H), 2.43 (br. s., 4H), 2.25 (br. s., 1H), 2.11-1.93 (m, 3H), 1.81 (br. s., 1H)

Example 29

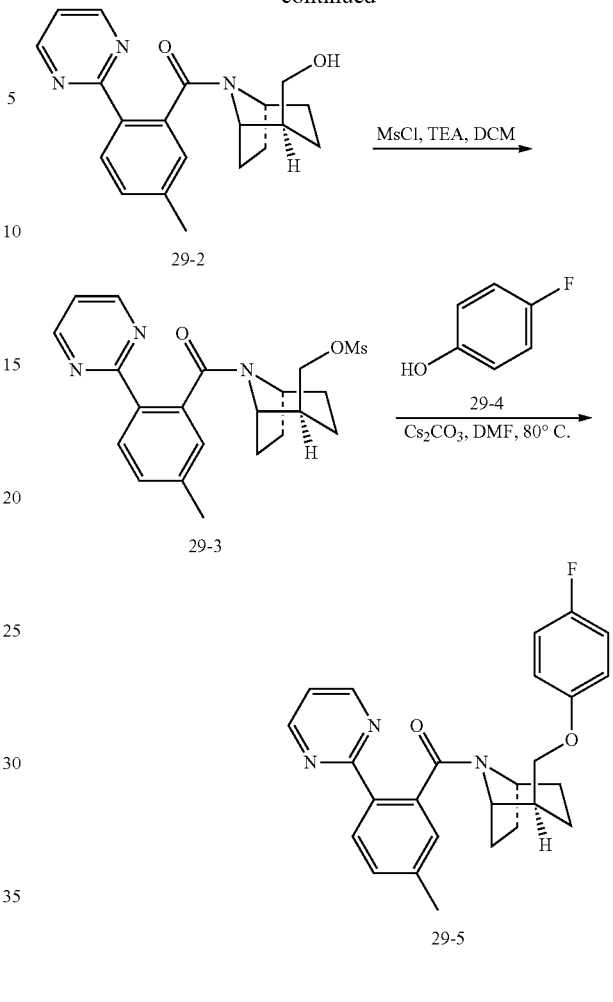

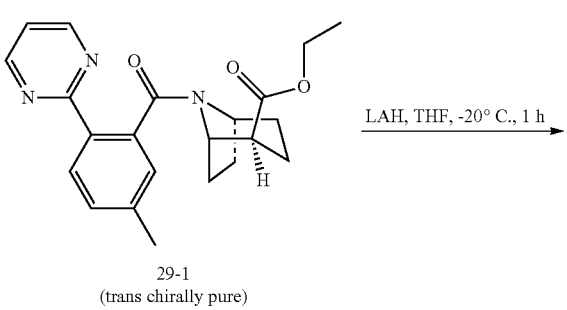

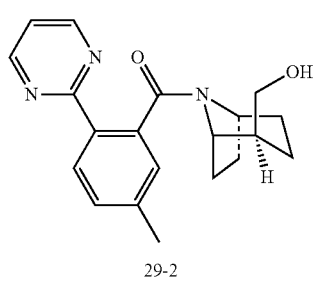

Step 29 (Synthesis of 29-1)

Compound 23-5 (5 g) was separated via SFC separation (separation method: Instrument Model: MG II preparative SFC (SFC-1); separation column: ChiralPak OD, 250×30 mm I.D.; mobile phase: A: CO₂, B: ethanol (0.1% aqueous ammonia); density: B 30%; flow rate: 55 mL/min; back flow pressure: 100 bar; column temperature: 38° C.; detection wavelength: 220 nm) to give a chirally pure product 29-1 (2 g, white solid, yield: 80%).

Step 2 (Synthesis of 29-2)

Compound 29-1 (1.3 g, 3.426 mmol) was solved in 25 mL THF, and LAH (100 mg, 2.5 mmol) was added slowly under iced ethanol bath. The reaction mixture was stirred under the present temperature for 1 hour. 20 mL of anhydrous THF was added for dilution. 0.1 mL of water, 0.1 mL of 15% sodium hydroxide solution and 0.3 mL of water were added dropwise successively to quench the reaction. The mixture was then dried over anhydrous Na₂SO₄, filtered, and the filtrate was concentrated under reduced pressure to give product 29-2 (1.1 g, yellow solid, yield: 96%), which was used directly in next step without purification.

Step 3 (Synthesis of 29-3)

Compound 29-2 (200 mg, 0.6 mmol) was dissolved in 10 mL DCM, and triethylamine (152 mg, 1.5 mmol) and MsCl (103 mg, 0.9 mmol) were added successively. The reaction mixture was stirred under room temperature for 2 hours, poured into saline solution and extracted with dichloromethane (10 mL×3). The combined organic phase was washed with water (10 mL×2), saturated NaCl solution (10 mL×2) successively, and dried over anhydrous Na$_2$SO$_4$, filtered, and the filtrate was concentrated under vacuum to give the product 29-3 (244 mg, yield: 98%), which was used in next step without purification.

Step 4 (Synthesis of 29-5)

Compound 29-3 (98 mg, 0.237 mmol) and compound 29-4 (53 mg, 0.474 mmol) were dissolved in 5 mL DMF, and cesium carbonate (196 mg, 0.6 mmol) was added under room temperature. The reaction mixture was stirred under 80° C. for 16 hour, poured into saline solution and extracted with ethyl acetate (20 mL×3). The combined organic phase was washed with water (10 mL×2), saturated NaCl solution (10 mL×2) successively, and dried over anhydrous Na$_2$SO$_4$, filtered, and the filtrate was concentrated under reduced pressure, and purified with preparative HPLC to give product 29-5 (5.45 mg, white solid, yield: 5.3%).

$^1$H NMR (400 MHz, CHCl$_3$-d)=8.76 (d, J=4.3 Hz, 1H), 8.70 (br. s., 1H), 8.16 (d, J=8.0 Hz, 0.5H), 8.10 (d, J=8.0 Hz, 0.5H), 7.31 (d, J=8.0 Hz, 0.5H), 7.17 (d, J=7.3 Hz, 1.5H), 7.10 (br. s., 1H), 6.98-6.88 (m, 3H), 6.57 (br. s., 1H), 5.00 (d, J=7.3 Hz, 0.6H), 4.92 (br. s., 0.4H), 4.26 (br. s., 0.6H), 4.04 (br. s., 0.4H), 3.84 (br. s., 1.5H), 3.66 (dd, J=6.0, 8.5 Hz, 0.5H), 2.41 (s, 2H), 2.17 (br. s., 0.5H), 1.98-1.73 (m, 7H), 1.52 (d, J=8.5 Hz, 1.5H), 1.25 (br. s., 1H)

Example 30

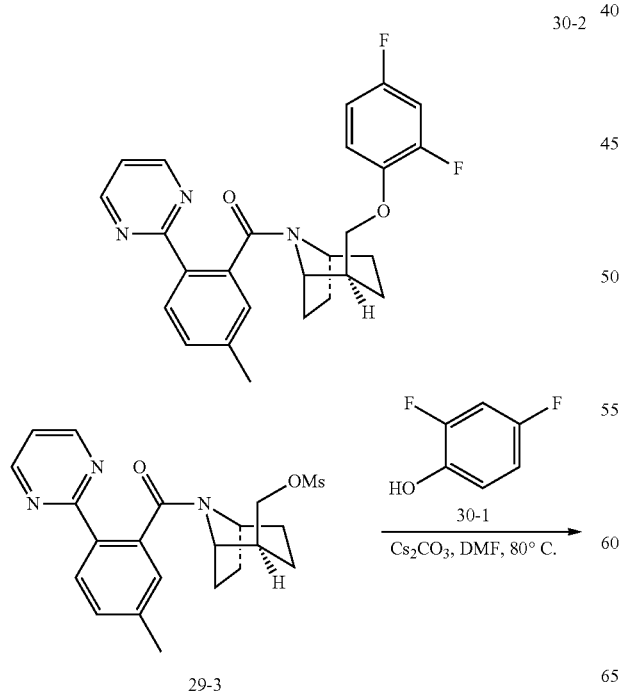

30-2

Step 30 (Synthesis of 30-2)

Compound 29-3 (98 mg, 0.237 mmol) and compound 30-1 (63 mg, 0.474 mmol) were dissolved in 5 mL DMF, and cesium carbonate (196 mg, 0.6 mmol) was added under room temperature. The reaction mixture was stirred under 80° C. for 16 hour, poured into saline solution and extracted with ethyl acetate (20 mL×3). The combined organic phase was washed with water (10 mL×2), saturated NaCl solution (10 mL×2) successively, and dried over anhydrous Na$_2$SO$_4$, filtered, and the filtrate was concentrated under reduced pressure, and purified with preparative HPLC to give product 30-2 (19.63 mg, white solid, yield: 18.4%).

$^1$H NMR (400 MHz, CHCl$_3$-d)=8.75 (d, J=3.8 Hz, 1H), 8.70 (br. s., 1H), 8.17 (d, J=8.0 Hz, 0.6H), 8.12 (d, J=7.8 Hz, 0.4H), 7.31 (d, J=7.8 Hz, 0.5H), 7.21 (d, J=8.0 Hz, 0.5H), 7.18-7.05 (m, 2.5H), 6.91-6.82 (m, 1H), 6.79 (br. s., 1.5H), 5.01 (d, J=6.5 Hz, 0.5H), 4.92 (br. s., 0.5H), 4.32 (br. s., 0.6H), 4.12 (br. s., 0.4H), 4.03-3.68 (m, 2H), 2.41 (s, 2H), 2.21 (br. s., 1H), 2.02 (d, J=11.5 Hz, 2H), 1.94-1.78 (m, 4H), 1.61-1.48 (m, 2H), 1.25 (br. s., 1H)

Example 31

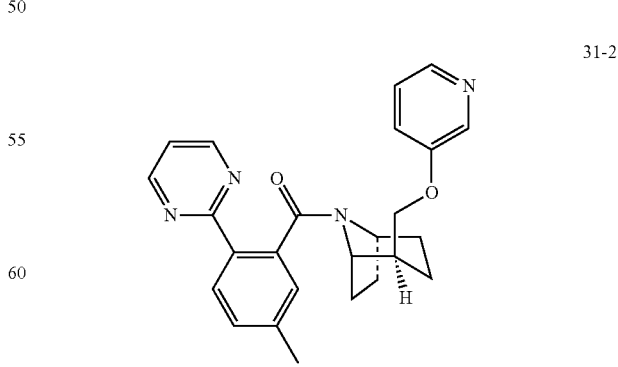

31-2

Example 31 followed the synthetic route of example 30, wherein the reagent 30-1 was replaced with 31-1:

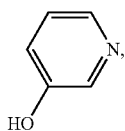

31-1 and the product 31-2 was obtained by preparative HPLC purification (5.79 mg, white solid, yield: 5.9%).

$^1$H NMR (400 MHz, CHCl$_3$-d)=8.84-8.61 (m, 2H), 8.47-8.26 (m, 1H), 8.18 (d, J=8.0 Hz, 1H), 8.12-8.06 (m, 0.5H), 8.02 (br. s., 0.5H), 7.37 (dd, J=1.5, 8.5 Hz, 0.5H), 7.33-7.27 (m, 1.5H), 7.22-7.04 (m, 3H), 5.02 (d, J=6.5 Hz, 1H), 4.40 (br. s., 0.5H), 4.17-4.06 (m, 0.5H), 3.92 (br. s., 1H), 3.80 (br. s., 0.5H), 3.74 (dd, J=5.5, 8.5 Hz, 0.5H), 2.41 (s, 1.5H), 2.26-2.21 (m, 0.5H), 1.99-1.73 (m, 6H), 1.67 (br. s., 1.5H), 1.51 (d, J=9.5 Hz, 1.5H), 0.98-0.79 (m, 1H)

Example 32

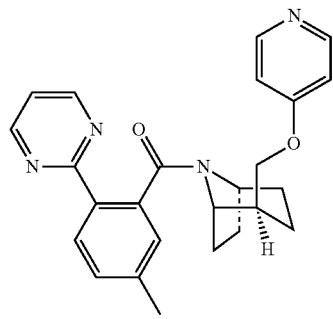

32-2

Example 31 followed the synthetic route of example 30, wherein the reagent 30-1 was replaced with 32-1:

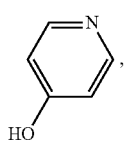

32-1 and the product 32-2 was obtained by preparative HPLC purification (7.32 mg, white solid, yield: 7.46%).

$^1$H NMR (400 MHz, CHCl$_3$-d)=8.75 (d, J=4.5 Hz, 2H), 8.26 (d, J=6.8 Hz, 1H), 7.87 (br. s., 2H), 7.36 (d, J=8.0 Hz, 1H), 7.20 (br. s., 2H), 6.60 (br. s., 2H), 4.75 (d, J=5.5 Hz, 1H), 4.29 (br. s., 1H), 3.90 (br. s., 2H), 2.45 (s, 3.5H), 2.07 (br. s., 3.5H), 1.77 (br. s., 1H), 1.63 (br. s., 2H), 1.52 (d, J=12.8 Hz, 1H), 1.34 (br. s., 1H)

Example 33

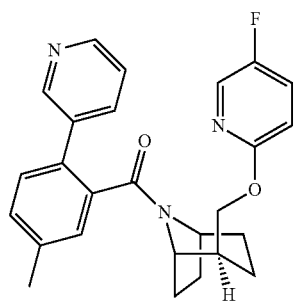

33-2

Example 33 followed the synthetic route of example 10, wherein the reagent 10-1 was replaced with 33-1:

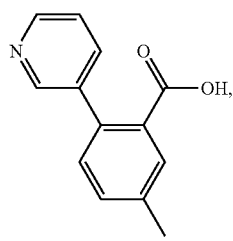

33-1 and the product 33-2 was obtained by preparative HPLC purification (25 mg, pale yellow solid, yield: 29%).

$^1$H NMR (400 MHz, CHCl$_3$-d)=8.87-8.68 (m, 1H), 8.68-8.48 (m, 1H), 8.30-7.89 (m, 2H), 7.58-7.40 (m, 1H), 7.34 (s, 1H), 7.33-7.22 (m, 2H), 7.18 (d, J=7.8 Hz, 1H), 6.77 (dd, J=3.0, 8.8 Hz, 0.4H), 6.30 (dd, J=3.1, 8.9 Hz, 0.6H), 4.95-4.71 (m, 1H), 4.07-3.92 (m, 1H), 3.71-3.49 (m, 1H), 3.38 (br. s., 1H), 2.44 (s, 1H), 2.29-2.04 (m, 1H), 2.04-1.93 (m, 2H), 1.93-1.70 (m, 2H), 1.66-1.52 (m, 1H), 1.59-1.20 (m, 5H)

Example 34

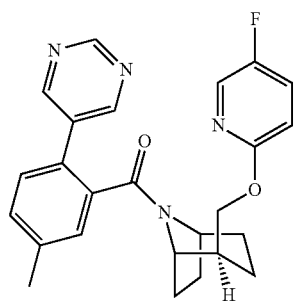

34-2

Example 34 followed the synthetic route of example 10, wherein the reagent 10-1 was replaced with 34-1:

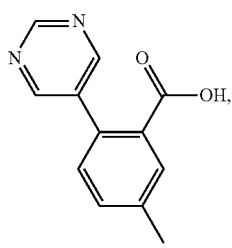

34-1 and the product 34-2 was obtained by preparative HPLC purification (30 mg, pale yellow solid, yield: 34.5%).

$^1$H NMR (400 MHz, CHCl$_3$-d)=9.31-9.12 (m, 1H), 9.06-8.74 (m, 2H), 8.07-7.88 (m, 1H), 7.43-7.10 (m, 4H), 6.78 (dd, J=3.4, 8.9 Hz, 0.4H), 6.28 (dd, J=3.4, 8.9 Hz, 0.6H), 4.98-4.73 (m, 1H), 4.41 (br. s., 1H), 4.13-3.85 (m, 1H), 3.69-3.44 (m, 1H), 2.45 (s, 1H), 2.33-2.06 (m, 1H), 2.04-1.93 (m, 3H), 1.93-1.73 (m, 2H), 1.68 (br. s., 1H), 1.60-1.51 (m, 1H), 1.50-1.23 (m, 3H)

Example 35

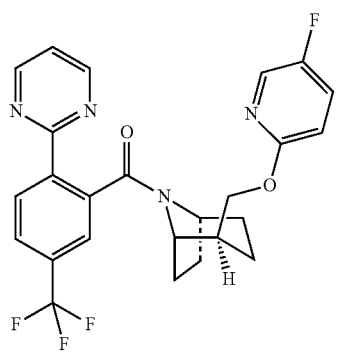

35-2

Example 35 followed the synthetic route of example 10, wherein the reagent 10-1 was replaced with 35-1:

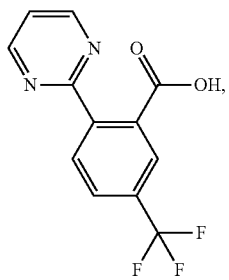

35-1 and the product 35-2 was obtained by preparative HPLC purification (4.47 mg, white solid, yield: 4.6%).

$^1$H NMR (400 MHz, CHCl$_3$-d)=8.80 (br. s., 2H), 8.52-8.25 (m, 1H), 7.86-7.63 (m, 2H), 7.31 (t, J=8.2 Hz, 1H), 7.26-7.18 (m, 2H), 6.75 (dd, J=3.5, 9.0 Hz, 0.5H), 6.26 (br. s., 0.5H), 5.02 (br. s., 1H), 4.65-4.38 (m, 1H), 4.28-3.98 (m, 1H), 3.78 (br. s., 1H), 2.27-2.10 (m, 1H), 2.06-1.79 (m, 3H), 1.59-1.56 (m, 4H), 1.25 (br. s., 1H)

Example 36

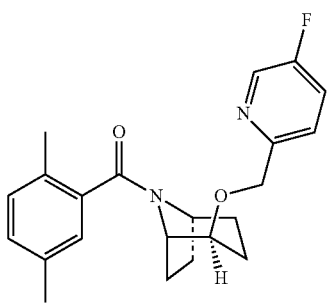

36-2

Example 36 followed the synthetic route of example 10, wherein the reagent 10-1 was replaced with 36-1:

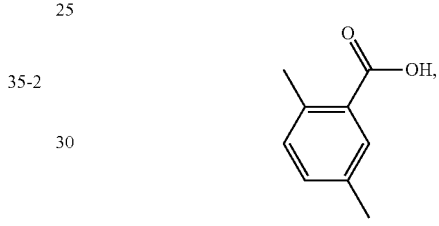

36-1 and the product 36-2 was obtained by preparative HPLC purification (25.32 mg, white solid, yield: 34.4%).

$^1$H NMR (400 MHz, CHCl$_3$-d)=8.06-7.79 (m, 1H), 7.38-7.27 (m, 1H), 7.12-7.02 (m, 1H), 6.95-6.77 (m, 2H), 6.29 (br. s., 1H), 5.09-4.93 (m, 1H), 4.54 (dd, J=7.8, 10.5 Hz, 0.5H), 4.34 (dd, J=7.7, 10.4 Hz, 0.5H), 4.22-4.14 (m, 0.5H), 4.06 (br. s., 1H), 3.73 (br. s., 0.5H), 2.44-2.19 (m, 3H), 2.19-2.05 (m, 3H), 2.04-1.87 (m, 3H), 1.87-1.60 (m, 3H), 1.60-0.90 (m, 3H)

Example 37

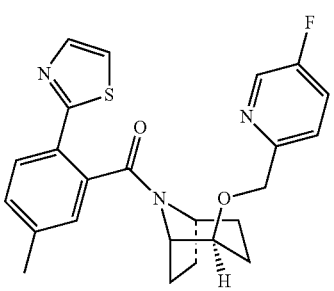

37-2

Example 37 followed the synthetic route of example 10, wherein the reagent 10-1 was replaced with 37-1:

37-1

[Structure: 2-(thiazol-2-yl)-5-methylbenzoic acid derivative]

and the product 37-2 was obtained by preparative HPLC purification (29.63 mg, beige solid, yield: 33.9%).

$^1$H NMR (400 MHz, CHCl$_3$-d)=8.30-7.93 (m, 1H), 7.92-7.78 (m, 1H), 7.77-7.54 (m, 1H), 7.46-6.95 (m, 4H), 6.79 (dd, J=3.5, 9.0 Hz, 0.5H), 6.33 (d, J=6.3 Hz, 0.5H), 5.11-4.76 (m, 1H), 4.69-4.24 (m, 1H), 4.16-3.97 (m, 1H), 3.89-3.55 (m, 1H), 2.42 (s, 1H), 2.27-1.94 (m, 3H), 1.92-1.70 (m, 3H), 1.63 (br. s., 1H), 1.56-1.39 (m, 2H), 1.27-0.80 (m, 2H)

Experimental Example 1: In Vitro Test of OX1/2R

Experimental Purpose:
The inhibitive effect of a compound on OX1 and OX2 GPCR receptor was evaluated by detecting calcium signal change in cells with FLIPR, and IC$_{50}$ value of compound was used as an indication.

Experimental Materials:
Cell line: HEK293-OX1 and OX2 stable cell strain
HEK293-OX1 cell culture media (DMEM, Invitrogen#11960-044, 10% serum Gibco#10099141, L-Glutamine 1×, Gibco#25030, sodium pyruvate 1×, Gibco #11360, Geneticin 300 μg/ml, Gibco #10131).
HEK293-OX2 cell culture media (DMEM, Invitrogen#11960-044, 10% serum Gibco#10099141, L-Glutamine 1×, Gibco#25030, sodium pyruvate 1×, Gibco #11360, Geneticin 300 μg/ml, Gibco #10131, Blasticin 2 μg/ml, Invitrogen # R21001).
Pancreatic enzyme (Invitrogen, #25200-072)
DPBS (Hyclone, #SH30028.01B)
Fluo-4 AM, Invitrogen# F14202
F-127, Invitrogen # P3000MP
Probenecid, Sigma # P8761
384-well cell plate, Greiner #781946
384-well compound plate, Greiner #781280
CO$_2$ incubator, Thermo#371
Centrifuge, Eppendorf #5810R
Vi-cell cytometry, Beckman Coulter
POD 810 Plate Assembler Automatic microplate pretreatment system
Labcyte FLIPR, Molecular Device.

Experimental Procedures and Methods:
a) cell inoculation (HEK293-OX1 and HEK293-OX2 cells)
1) The medium trypsin, and DPBS were preheated at 37° C. under water bath. Culture medium of cells was sucked and cells were washed with 10 mL DPBS.
2) The preheated trypsin was added into the culture bottle which was rotated so that trypsin uniformly covered the bottle. It was placed in an incubator (37° C., 5% CO$_2$) to digest for 1-2 minutes;
3) Each T150 was suspended with 10-15 mL of culture medium, and centrifuged at 800 rpm for 5 minutes. Cells were resuspended with 10 mL medium, and 1 mL of the cell re-suspension was sucked out and counted with Vi-cell cytometry.
4) The OX1 cells were diluted with culture medium to 5×10$^5$ cells/mL, and OX2 cells were diluted to 4×10$^5$ cells/mL. The diluted cells were added into 384 plate (Greiner. 781946) with multichannel pipettes (50 μL/hole, OX1 cells: 25000 cells/hole; and OX2 cells: 20000 cells/hole). The cell plate was placed in an incubator (37° C., 5% CO$_2$) overnight.

b) loading of the compound:
1) DMSO was used to dilute the compound into 20 mM by using 3-fold dilution. 8 gradients in duplicate wells were used. Echo liquid handler was used to add the compound into a compound plate. Then 20 μL buffer was added to ensure that the final DMSO concentration was 0.1%.

c) FLIPR Experiment:
1) The cell culture medium in 384-well plate was washed away with a vacuum pump. 30 μL fluorescent dye Fluo4AM was added. The cell was incubated at 37° C., 5% CO$_2$ in an incubator for 1 hr and then re-equilibrated under room temperature for 10 minutes.
2) EC50 Test: Orexin A was diluted manually on ice by using 3-fold diluted. 8 gradients in duplicate wells were used. Then the DMSO plate was prepared and the DMSO concentration was 0.5%. The cell plate, Orexin A plate, and DMSO plate were placed into FLIPR respectively, and the fluorescence values were read.
3) EC70 value was calculated based on EC50 value of Orexin A. 5×EC70 solution was prepared and added into a 384-well compound plate with multichannel pipettes. The plate was placed on ice for preservation.
4) In the FLIPR, the compound plate, 5×EC70 plate, cell plate and FLIPR tips were placed respectively. The program was run and the fluorescence values were read.

d) Data Analysis: Prism5.0 was used to analysis the data, and the IC$_{50}$ value of the compound was calculated.
The experimental results are shown in table 1:

TABLE 1

IC$_{50}$ experimental results detected in FLIPR

| Test sample (title compound) | hOX1R (nM) | hOX2R (nM) |
|---|---|---|
| MK6096 | 36 | 29 |
| Example 1 (1-16) | 10 | 24 |
| Example 2 (2-1) | 2296 | 2508 |
| Example 3 (3-3) | 2072 | 1425 |
| Example 4 (4-1) | 217 | 195 |
| Example 5 (5-3) | 20 | 36 |
| Example 6 (6-1) | 2552 | 4189 |
| Example 7 (7-3) | 1270 | 291 |
| Example 8 (8-1) | 4255 | 4609 |
| Example 9 (9-4) | 24 | 15 |
| Example 10 (10-2) | 29 | 73 |
| Example 11 (11-2) | 321 | 363 |
| Example 12 (12-2) | 219 | 206 |
| Example 13 (13-2) | 47 | 663 |
| Example 14 (14-2) | 16 | 20 |
| Example 15 (15-2) | 37 | 55 |
| Example 16 (16-2) | 56 | 440 |
| Example 17 (17-2) | 43 | 47 |
| Example 18 (18-2) | 127 | 904 |
| Example 19 (19-2) | 41 | 372 |
| Example 20 (20-2) | 7 | 26 |
| Example 21 (21-2) | 567 | 741 |
| Example 22 (22-2) | 2418 | 1371 |
| Example 23 (23-8) | 45 | 97 |
| Example 24 (24-2) | 56 | 87 |
| Example 25 (25-2) | 113 | 124 |
| Example 26 (26-5) | 48 | 37 |
| Example 27 (27-3) | 3000 | 3000 |
| Example 28 (28-1) | 34 | 23 |

TABLE 1-continued

IC$_{50}$ experimental results detected in FLIPR

| Test sample (title compound) | hOX1R (nM) | hOX2R (nM) |
|---|---|---|
| Example 29 (29-5) | 68 | 121 |
| Example 30 (30-2) | 489 | 262 |
| Example 31 (31-2) | 305 | 221 |
| Example 32 (32-2) | 7 | 6 |
| Example 33 (33-2) | 10 | 24 |
| Example 34 (34-2) | 2296 | 2508 |
| Example 35 (35-2) | 2072 | 1425 |
| Example 36 (36-2) | 217 | 195 |
| Example 37 (37-2) | 20 | 36 |

CONCLUSION

It can be seen from Table 1 that the exemplary compounds of invention significantly inhibit OX1 and OX2 GPCR receptors, and some of the compounds have more excellent activity when compared with the positive control. It has also found that for some exemplary compounds, the different spatial configuration may greatly impact the inhibitive effects on OX1 and OX2 GPCR receptors.

The invention claimed is:

1. A compound of formula (I), or a pharmaceutically acceptable salt thereof,

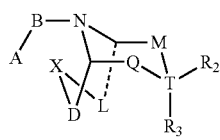
(I)

wherein:
A is selected from an optionally substituted 3-12 membered cyclohydrocarbyl or heterocyclohydrocarbyl or cyclic heterohydrocarbyl;
B is selected from C(=O);
X is a single bond of linkage;
D and L are independently selected from CH$_2$,
T is C;
M is selected from C(Y)(R$_{1a}$) when Q is selected from C(R$_{1b}$)(R$_{1c}$), or M is selected from C(R$_{1b}$)(R$_{1c}$) when Q is selected from C(Y)(R$_{1a}$);
Y is selected from —(CH$_2$)$_{r4}$(G)$_{r5}$(CH$_2$)$_{r6}$—Y$_1$, wherein Y$_1$ is selected from —O-E or a structure of formula Y$_{22}$ which is optionally substituted,

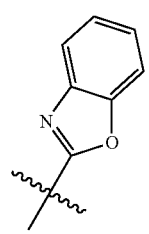
(Y$_{22}$)

wherein the substituent is selected from F, Cl, Br, halogen-substituted or unsubstituted C$_{1-6}$ alkyl;

G is unsubstituted CH$_2$;
r$_4$ and r$_6$ are independently selected from 0, r$_5$ is selected from 0 or 1, and when r$_4$, r$_5$ and r$_6$ are all 0, it means the corresponding structure is a single bond of linkage;
E is selected from a structure unit of formula (Ea):

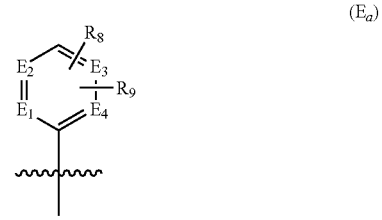
(E$_a$)

wherein:
the structure unit

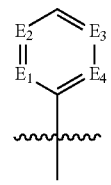

is defined as phenyl or pyridyl;
R$_8$ and R$_9$ are independently selected from H, F, Cl, Br, halogen-substituted or unsubstituted C$_{1-6}$ alkyl;
each of R$_{1a}$, R$_{1b}$, R$_{1c}$, R$_2$, and R$_3$ is independently selected from H, F, Cl, halogen-substituted and
the compound or the pharmaceutically acceptable salt thereof comprises one or more chiral center;
wherein A is selected from a structure unit as shown in formula (A$_1$) or (A$_2$):

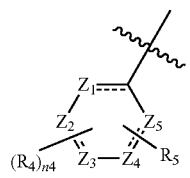
(A$_1$)

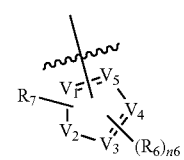
(A$_2$)

wherein:
the structure unit

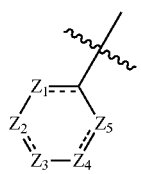

is phenyl;

formula (A$_2$) is of formula (A$_{22}$):

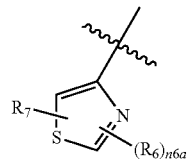
(A$_{22}$)

n$_{6a}$ is selected from 0 or 1;
R$_4$ and R$_6$ are independently selected from H, F, Cl, Br, halogen-substituted, or unsubstituted C$_{1-6}$ alkyl;
R$_5$ and R$_7$ are independently selected from optionally substituted 5-6 membered cyclohydrocarbyl or heterocyclic group, while the substituent is selected from F, Cl, Br, CN, halogen-substituted or unsubstituted C$_{1-6}$ alkyl wherein the 5-6 membered cyclohydrocarbyl or heterocyclic group are each independently selected from phenyl, pyridyl, furyl, thienyl, thiazolyl, pyrimidinyl, pyrazolyl, 1,2,3-triazolyl or 1,2,5-triazolyl;
n$_4$ is selected from 0, 1, 2, 3, 4; and
C$_{1-6}$ alkyl is selected from methyl, ethyl, propyl, butyl, pentyl, or hexyl.

2. The compound of claim 1 or the pharmaceutically acceptable salt thereof, wherein A is selected from:

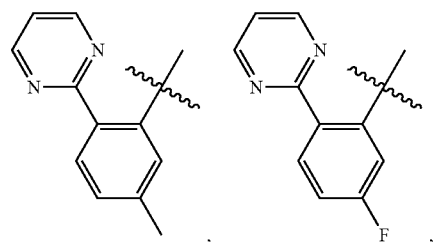

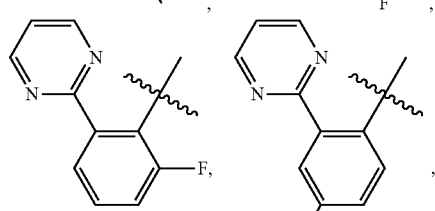

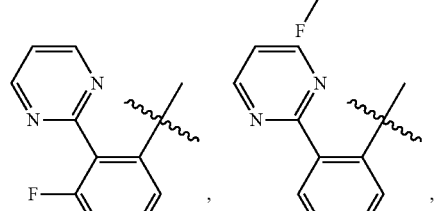

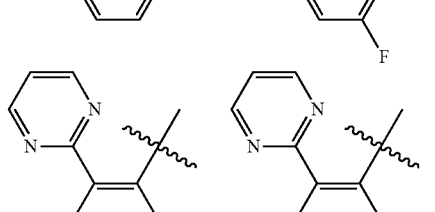

-continued

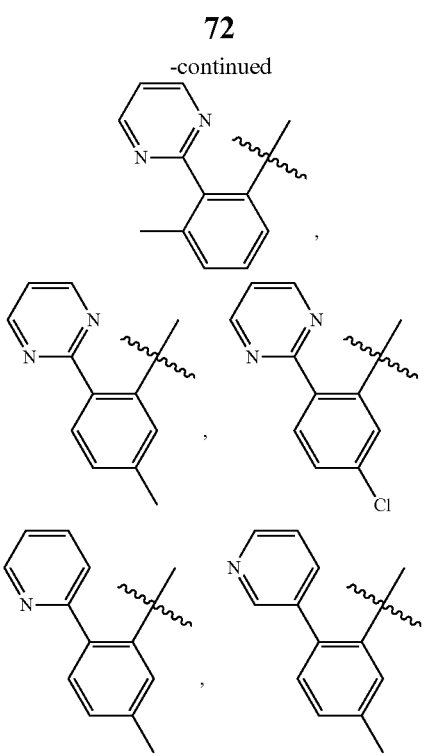

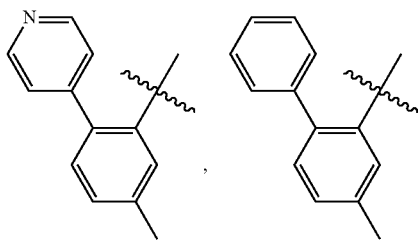

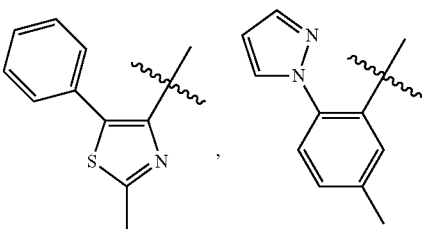

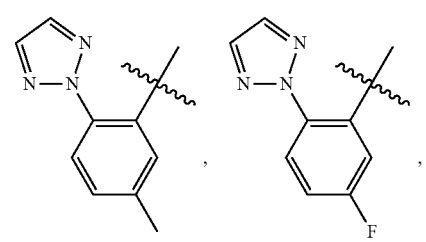

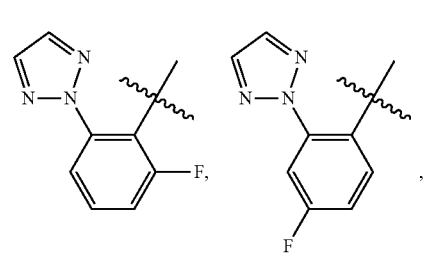

-continued

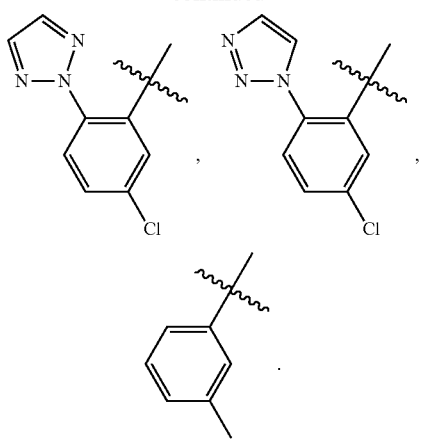

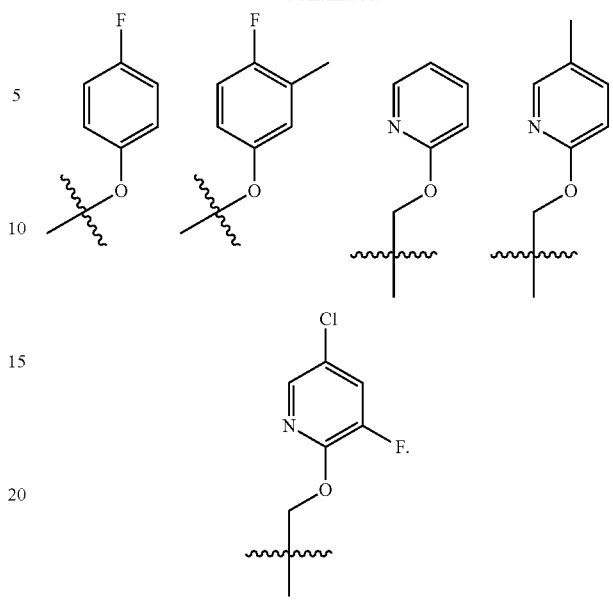

3. The compound of claim 1 or the pharmaceutically acceptable salt thereof, wherein Y is selected from —CH$_2$—O-E or —O-E, wherein E is defined as in claim 1.

4. The compound of claim 1 or the pharmaceutically acceptable salt thereof, wherein the structure unit

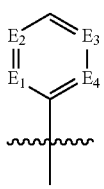

is defined as pyridyl.

5. The compound of claim 3 or the pharmaceutically acceptable salt thereof, wherein Y is selected from:

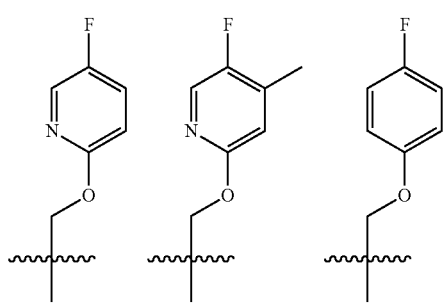

6. The compound of claim 1 or the pharmaceutically acceptable salt thereof, wherein $R_{1a}$, $R_{1b}$, and $R_{1c}$ are independently selected from H, methyl, or fluoro.

7. The compound of claim 1 or the pharmaceutically acceptable salt thereof, wherein $R_2$ and $R_3$ are independently selected from H, methyl or fluoro.

8. The compound of claim 1 or the pharmaceutically acceptable salt thereof, which has any of the following structures:

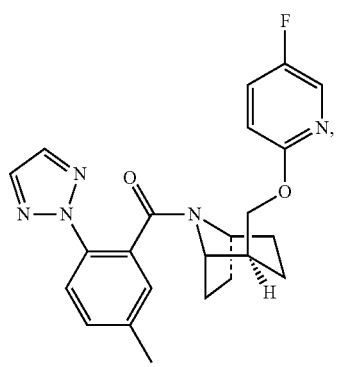

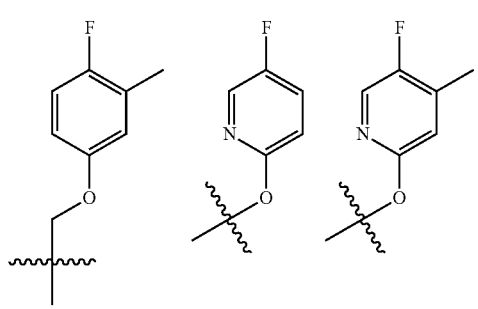

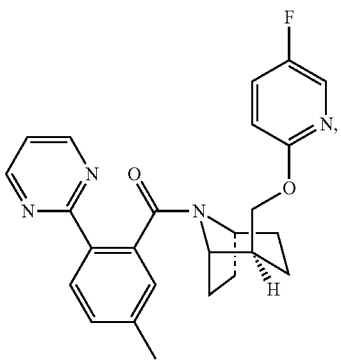

-continued
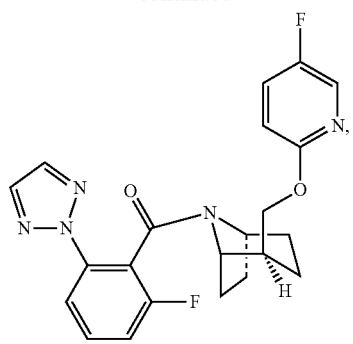
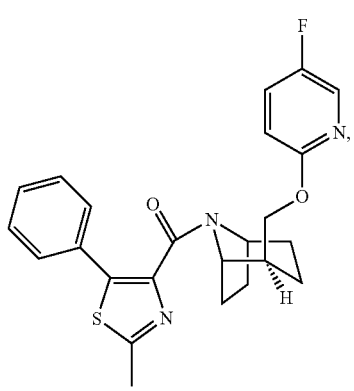
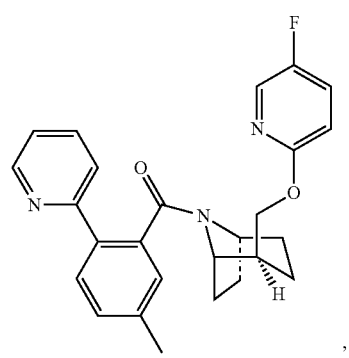
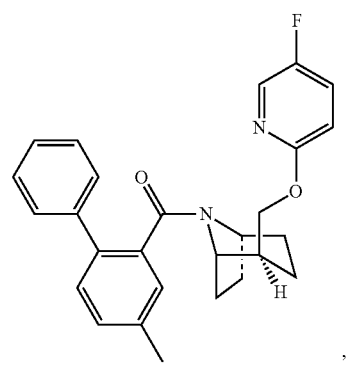
-continued
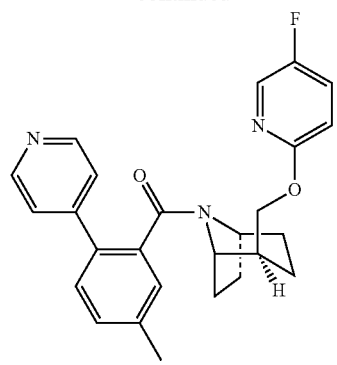
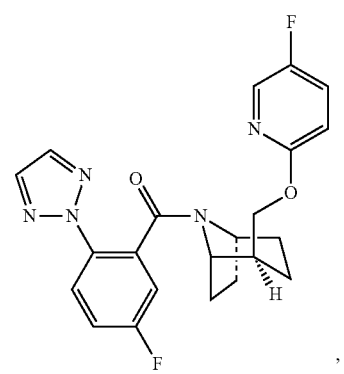
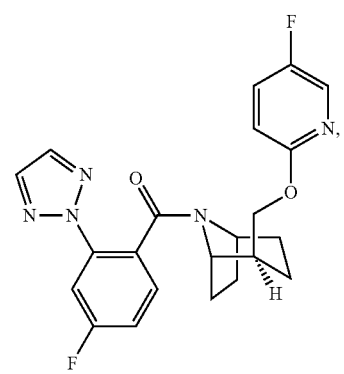
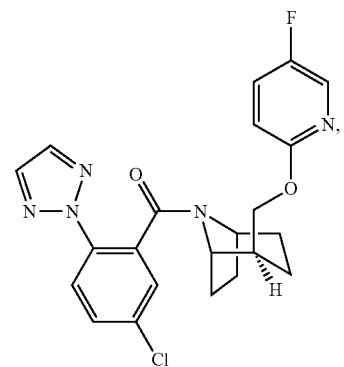

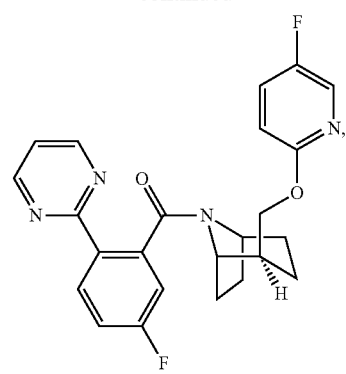
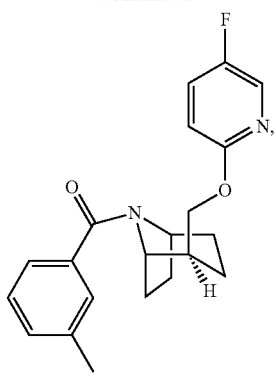
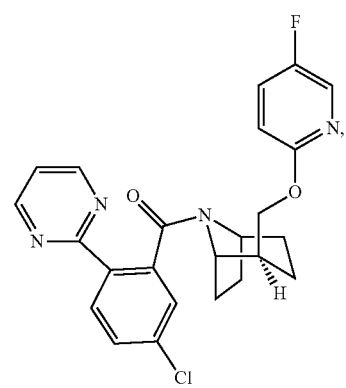
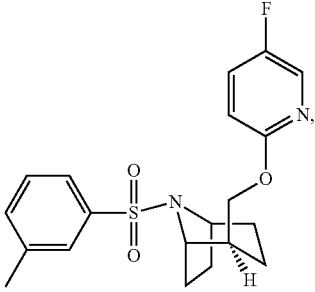
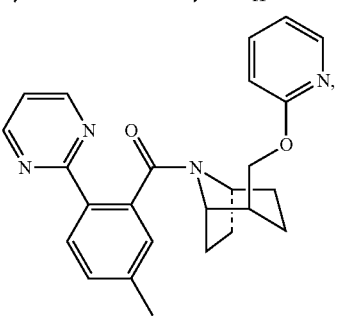
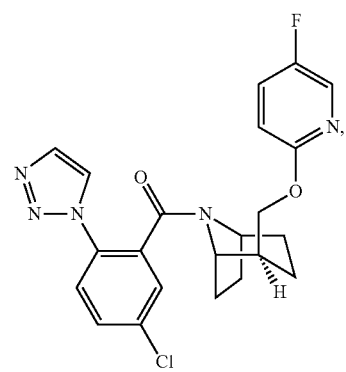
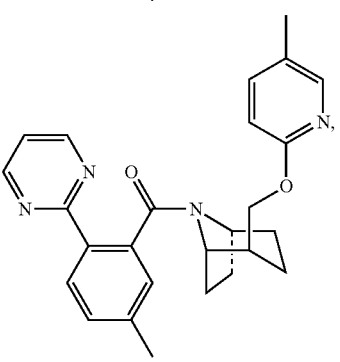
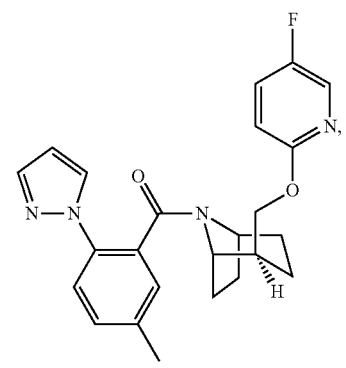
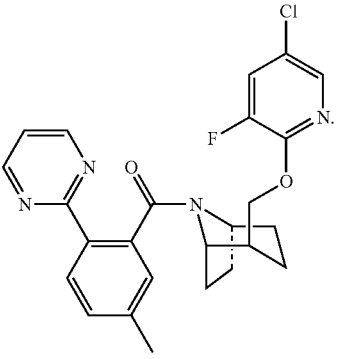

9. A pharmaceutical composition comprising a therapeutically effective amount of the compound of claim 1, or a pharmaceutically acceptable salt thereof, and a pharmaceutically acceptable carrier.

10. A method for treating insomnia, chronic obstructive pulmonary disease, obstructive sleep apnea, hypersomnia, anxiety, obsessive-compulsive disorder, panic attack, nicotine addiction, or binge eating disorder wherein comprises the following step: administrating treatment effective dose of a compound of claim 1 or a pharmaceutically acceptable salt thereof to the subjects in need.

* * * * *